United States Patent [19]
Nobori et al.

[11] Patent Number: 5,990,352
[45] Date of Patent: *Nov. 23, 1999

[54] PHOSPHAZENIUM SALT AND PREPARATION PROCESS THEREOF, AND PROCESS FOR PRODUCING POLY (ALKYLENE OXIDE)

[75] Inventors: Tadahito Nobori; Masahiro Kouno, both of Kanagawa-ken; Toshiaki Suzuki, Kyoto; Kazumi Mizutani, Kanagawa-ken; Shinji Kiyono, Kanagawa-ken; Yoshiho Sonobe, Kanagawa-ken; Usaji Takaki, Kanagawa-ken, all of Japan

[73] Assignee: Mitsui Chemicals, Inc., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/796,893

[22] Filed: Feb. 5, 1997

[30] Foreign Application Priority Data

| Feb. 20, 1996 | [JP] | Japan | 8-032018 |
| Feb. 27, 1996 | [JP] | Japan | 8-039342 |
| Mar. 14, 1996 | [JP] | Japan | 8-057181 |
| May 9, 1996 | [JP] | Japan | 8-114773 |
| May 14, 1996 | [JP] | Japan | 8-118851 |
| May 28, 1996 | [JP] | Japan | 8-133983 |

[51] Int. Cl.$^6$ .......... C07F 9/02; C07D 211/92; C07D 223/04; C07D 207/46

[52] U.S. Cl. .......... 564/12; 502/164; 540/542; 546/21; 546/184; 548/111; 548/579

[58] Field of Search ............... 564/12; 502/164; 546/21, 184; 540/542; 548/111, 5.79

[56] References Cited

U.S. PATENT DOCUMENTS

| 3,829,505 | 8/1974 | Herold | 260/611 B |
| 5,401,814 | 3/1995 | Schomaker et al. | 525/523 |
| 5,627,291 | 5/1997 | Fischer | 549/507 |

FOREIGN PATENT DOCUMENTS

| 50-159595 | 12/1975 | Japan . |
| 56-38323 | 4/1981 | Japan . |
| 57-12026 | 1/1982 | Japan . |
| 62-232433 | 10/1987 | Japan . |
| 2-276821 | 11/1990 | Japan . |
| 48-93697 | 12/1993 | Japan . |

OTHER PUBLICATIONS

Schwesinger et al., Chem Abst. 108:37964, 1988.

Esswein et al, "Anionic Polymerization of Oxirane in the Presence of the Polyiminophosphazene base t–Bu–P$_4$", Macronol, Rapid Commun, 17, pp. 143–148 (1996).

Esswein et al, "Polymerization of Ethylene Oxide with Alkyllithium Compounds and the Posphazene Base tBu–P$_4$", Angew, Chem. Int. Ed. Engl., 35, No. 6, pp. 623–625 (1996).

Esswein et al, "Use of Polyiminophosphazenen Bases for Ring–opening Polymerzations", Macromol Symp., 107, pp. 331–340 (1996).

Primary Examiner—Peter O'Sullivan
Attorney, Agent, or Firm—Burns, Doane, Swecker & Mathis, L.L.P.

[57] ABSTRACT

A salt useful as an active species in an organic reaction and represented by the following chemical formula (1):

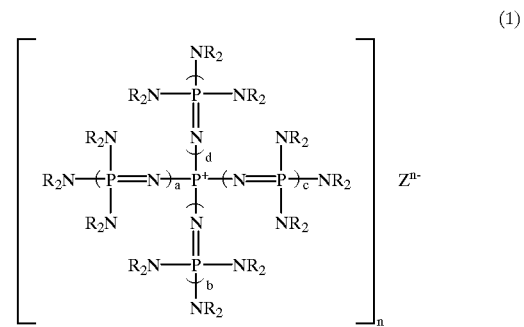

(1)

wherein n stands for an integer of from 1 to 8, $Z^{n-}$ represents an n-valent anion of an active hydrogen compound, a, b, c and d each stands for a positive integer, and Rs represent the same or different hydrocarbon groups. In addition, a simple and efficient process is provided for producing a poly (alkylene oxide) by polymerizing an alkylene oxide compound in the presence of the salt represented by the chemical formula (1).

11 Claims, 30 Drawing Sheets

PHOSPHAZENIUM SALT AND PREPARATION PROCESS THEREOF, AND PROCESS FOR PRODUCING POLY (ALKYLENE OXIDE)

BACKGROUND OF THE INVENTION

1. Field of the Invention

This invention relates to a salt of an anion of an active hydrogen compound in a form derived by elimination of protons from the active hydrogen compound, said salt being novel and extremely important for organic reactions. More specifically, the present invention is concerned with a novel salt of a phosphazenium cation and an anion of an active hydrogen compound or a novel phosphazenium hydroxide as an example of the salt and with its preparation process, and also with use of the salt or the hydroxide as an effective catalyst for the polymerization of an alkylene oxide compound.

A poly(alkylene oxide) is an important polymer useful as a raw material for the production of polyurethane foams and elastomers available through its reaction with organopolyisocyanate compounds and also as a surfactant.

2. Description of the Related Art

It has been well known for many years to convert an active hydrogen compound into an anion by taking a proton out of the active hydrogen compound and then to obtain its salt with a counter cation. Depending on the strength of acidity of the active hydrogen compound, various processes are used. For example, carboxylic acids, nitroalkanes, alcohols or phenols can be rather easily formed into salts through reactions with alkali metal hydroxides or in some instances, alkali metal carbonates or the like. For the formation of salts of ketones, alkylnitriles, cyclopentadienes, amines, amides or imides, it is a common practice to use alkali metals or compounds thereof such as alkali metals, alkali metal hydrides, alkali metal amides or alkyl alkali metals. The salts obtainable by these processes are however salts of anions derived from active hydrogen compounds and alkali metal cations. To make effective the reactivity of an anion of an active hydrogen compound, it is necessary to dissolve its salt in a solvent. However, solvents which can sufficiently dissolve a salt containing such an alkali metal cation are extremely limited. In some instances, the reactivity of an anion may be substantially affected by the size of its counter cation. If this cation is limited to an alkali metal cation, a limitation is imposed on the size of a cation.

Further, the hydroxides of alkali metals or alkaline earth metals are also extremely important compounds in the field of organic reactions for their basicity. To improve the effects of these hydroxides upon using them in organic reactions, it is important to dissolve them in an organic solvent. These hydroxide are soluble in water but are only sparingly soluble in general organic solvents. They hence have an unsuitable side effect for organic reactions which are apt to be easily impaired by water.

Industrial practice of an organic reaction by using a salt of an anion derived from an active hydrogen compound and an alkali metal cation or the hydroxide of an alkali metal or alkaline earth metal involves such problems as mentioned above.

Upon production of a poly(alkylene oxide) by polymerization of an alkylene oxide compound, it is most usual to use, as an initiator system, a combination of an active hydrogen compound such as a polyhydric alcohol and a basic alkali metal compound such as potassium hydroxide. Such initiator systems are also used in industry. Nonetheless, there is a desire for the development of an initiator system which is more efficient from the standpoint of polymerization activity and physical properties of a resulting polymer. Concerning initiator systems other than the combinations mentioned above, U.S. Pat. No. 3,829,505 discloses obtaining a polymer from propylene oxide by using an active hydrogen compound and, for example, a compound represented by $Zn_3[Fe(CN)_6]_2 \cdot H_2O \cdot$ dioxane. Japanese Patent Laid-Open No. 276821/1990 discloses obtaining a poly (alkylene oxide) by using zinc hexacyanocobaltate. Further, Japanese Patent Laid-Open No. 232433/1987 discloses obtaining a polymer by polymerizing ethylene oxide while using a reaction product which has been obtained by adding a solution of diethyl zinc in hexane to a dispersion formed by adding 1,4-butanediol and a nonionic surfactant to a slurry of fumed silica in hexane. These initiator systems all contain special metal components and, if these metal components remain in the resulting poly(alkylene oxide), they adversely affect reactions upon production of polyurethanes or physical properties of the polyurethanes so produced. A special process or complex steps are therefore needed for the full elimination of such metal components upon production of poly(alkylene oxide).

Concerning metal-free initiator systems, on the other hand, Japanese Patent Laid-Open No. 159595/1975 discloses preparation of a polymer from ethylene oxide by a combination of an alkane polyol, an active hydrogen compound, and an ether adduct of boron trifluoride. With respect to this initiator system, it is however also known that certain specific impurities in the polymer give deleterious effects on some physical properties of urethane. Cumbersome steps are thus required for their full elimination. Further, according to Japanese Patent Laid-Open No. 12026/1982, a polymer of an alkylene oxide is obtained using an alcohol and aminophenol. According to Japanese Patent Laid-Open No. 38323/1981, propylene oxide is polymerized using sorbitol and tetramethylammonium hydroxide. These initiator systems are however accompanied by problems such that their polymerization activities are not sufficient and moreover, an amine-like odor remains in the resulting polymers.

SUMMARY OF THE INVENTION

An object of the present invention is to provide a salt of an anion derived from an active hydrogen compound and a counter cation, said salt being of properties such that the cation is not an alkali metal cation and is changeable in size as needed and the salt is rather easily soluble, and also to provide a compound which is free of any metal component, has basicity similar to the hydroxide of an alkali metal or alkaline earth metal, and is readily soluble in an organic solvent. Another object of the present invention is to provide an effective process for the preparation of such a salt.

A further object of the present invention is to provide a simple and effective process for producing a poly(alkylene oxide) by polymerizing an alkylene oxide compound while using an initiator system which does not contain any unusual metal component or any metal component and does not allow an odor to remain To achieve the above-described objects, the present inventors have proceeded with an extensive investigation. As a result, it has been found that a novel phosphazenium salt of an active hydrogen compound and a novel phosphazenium hydroxide are extremely effective and further that they are extremely effective for the polymerization of an alkylene oxide compound, leading to the completion of the present invention.

The present invention therefore provides:

A phosphazenium salt of an active hydrogen compound represented by the following chemical formula (1):

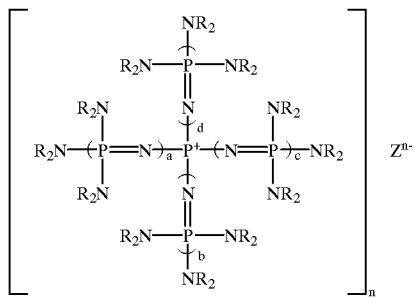
(1)

wherein:
n stands for an integer of from 1 to 8 and represents the number of phosphazenium cations, and
$Z^{n-}$ represents an n-valent anion of an active hydrogen compound in a form derived by elimination of n protons from an active hydrogen compound having at most eight active hydrogen atoms on oxygen atoms or nitrogen atoms, a, b, c and d each stands for a positive integer of 3 or smaller or 0 with the proviso that they are not all 0 at the same time, Rs represent the same or different hydrocarbon groups having 1 to 10 carbon atoms, and two Rs on each common nitrogen atom may be coupled together to form a ring structure;

A phosphazenium hydroxide represented by the following chemical formula (2):

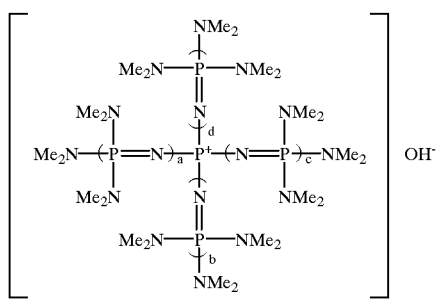
(2)

wherein each Me represents a methyl group, and a, b, c and d are each 0 or 1 with the proviso that they are not all 0 at the same time;

A process for the preparation of a phosphazenium salt of an active hydrogen compound represented by the following chemical formula (1):

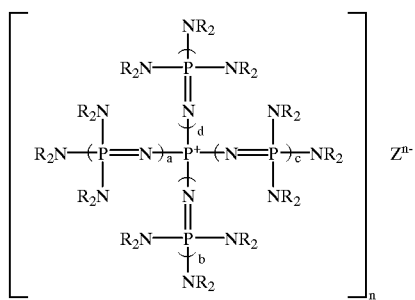
(1)

wherein:
n stands for an integer of from 1 to 8 and represents the number of phosphazenium cations, and
$Z^{n-}$ represents an n-valent anion of an active hydrogen compound in a form derived by elimination of n protons from an active hydrogen compound having at most eight active hydrogen atoms on oxygen atoms or nitrogen atoms, a, b, c and d each stands for a positive integer of 3 or smaller or 0 with the proviso that they are not all 0 at the same time, Rs represent the same or different hydrocarbon groups having 1 to 10 carbon atoms, and two Rs on each common nitrogen atom may be coupled together to form a ring structure, which comprises reacting a salt of a phosphazenium cation and an inorganic anion, said salt being represented by the following formula (3):

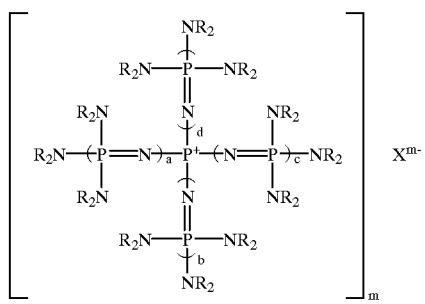
(3)

wherein m stands for an integer of from 1 to 3 and represents the number of said phosphazenium cation, $X^{m-}$ represents an m-valent inorganic anion, a, b, c, d and Rs have the same meanings as defined above, with an alkali metal salt of an active hydrogen compound, said alkali metal salt being represented by $M^+{}_n Z^{n-}$ wherein $M^+{}_n$ represents n alkali metal cations, and n and $Z^{n-}$ have the same meanings as defined above;

A process for the preparation of a phosphazenium hydroxide represented by the following chemical formula (2):

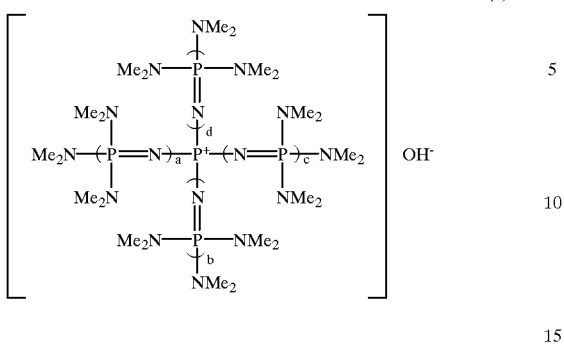

(2)

wherein each Me represents a methyl group, and a, b, c and d are each 0 or 1 with the proviso that they are not all 0 at the same time, which comprises bringing a solution of a salt of a phosphazenium cation and a monovalent inorganic anion, said salt being represented by the following formula (4):

(4)

wherein each Me, a, b, c and d have the same meanings as defined above and $Y^-$ represents said monovalent inorganic anion, in a mixed solvent of water and a water-miscible organic solvent into contact with a hydroxideform anion-exchange resin;

A process for producing a poly(alkylene oxide) by polymerization of an alkylene oxide compound, which comprises polymerizing said alkylene oxide compound in the presence of:

(I-i) (a) a salt of a phosphazenium cation and an inorganic anion, said salt being represented by the following chemical formula (5) or chemical formula (6):

(5)

(6)

wherein a, b, c and d in the chemical formula (5) or e, f and g in the chemical formula (6) each stands for a positive integer of 3 or smaller or 0 with the proviso that a, b, c and d or e, f and g are not all 0 at the same time, Rs represent the same or different hydrocarbon groups having 1 to 10 carbon atoms, two Rs on each common nitrogen atom may be coupled together to form a ring structure, r stands for an integer of from 1 to 3 and represents the number of phosphazenium cations, and $T^{r-}$ represents of an r-valent inorganic anion, and (b) an alkali metal or alkaline earth metal salt of an active hydrogen compound, or (I-ii) a phosphazenium salt of an active hydrogen compound, said phosphazenium salt having been derived from:

(a) a salt of a phosphazenium cation and an inorganic anion, said salt being represented by the chemical formula (5), and (b) an alkali metal or alkaline earth metal salt of an active hydrogen compound; or (II-i) (a) a phosphazenium compound represented by the following formula (7):

(7)

wherein a, b, c, d and Rs have the same meanings as defined above, and $Q^-$ represents a hydroxyl anion, alkoxyl anion, aryloxyl anion or carboxyl anion, and (b) an active hydrogen compound, or (II-ii) a phosphazenium salt of an active hydrogen compound, said phosphazenium salt having been derived from:

(a) a phosphazenium compound represented by the chemical formula (7), and (b) an active hydrogen compound; and A poly(alkylene oxide) obtained by the process described above.

DETAILED DESCRIPTION OF THE INVENTION

Figure 1:
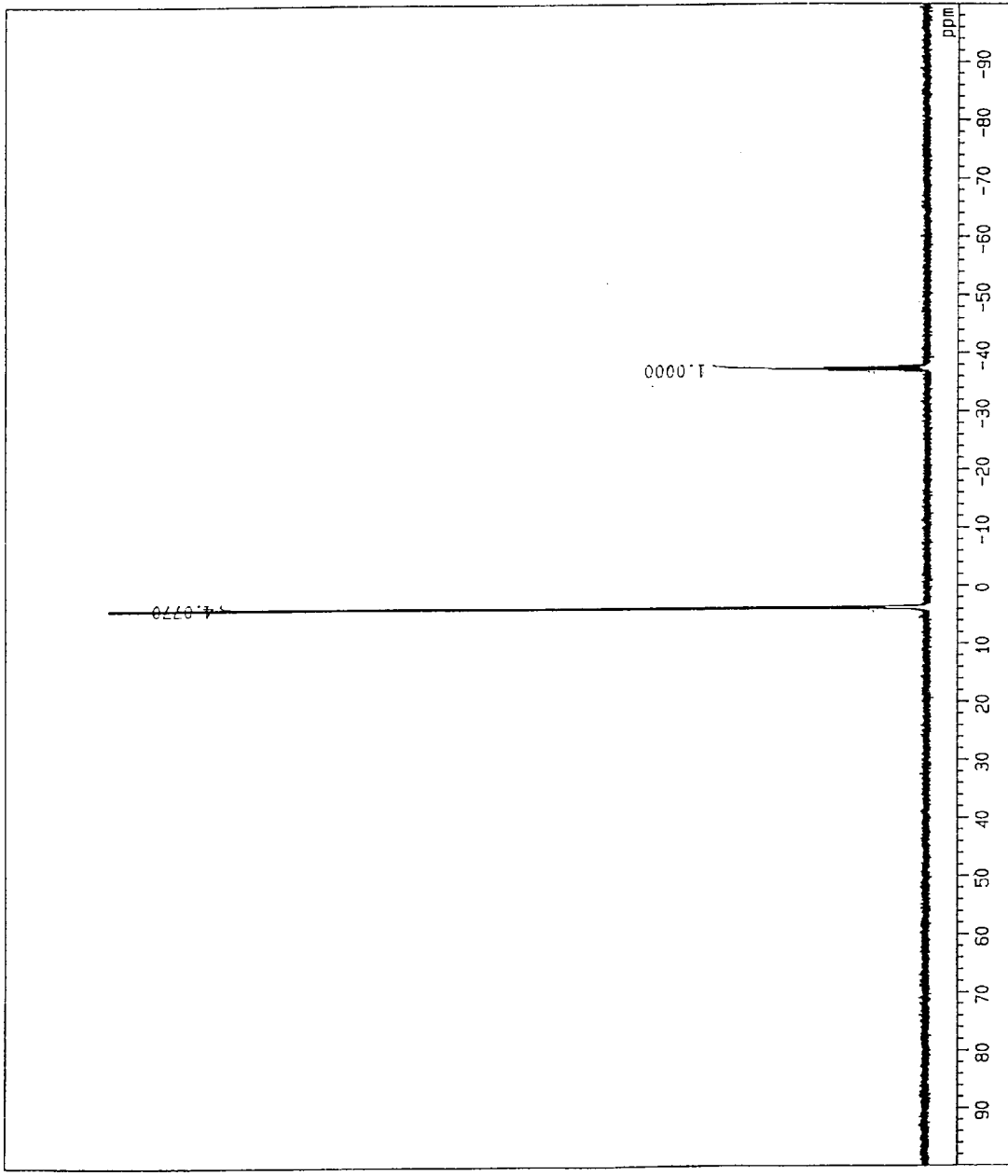
FIG. 1 is a $^{31}$P-NMR (solvent: DMSO-$d_6$) spectrum of the tetrakis[tris(dimethylamino)phosphoranilideneamino] phosphonium salt of methanol.

The phosphazenium cations in the phosphazenium compounds represented by the chemical formula (1), chemical formula (2), chemical formula (3), chemical formula (4), chemical formula (5), chemical formula (6) and chemical formula (7) in the present invention have been represented by the limiting structural formulas each in which the positive charge is localized on the central phosphorus atom. Besides this, a number of limiting structural formulas can be drawn. Actual positive charge is delocalized throughout the entire molecules, respectively.

In one aspect of the present invention, there are provided the phosphazenium salt of the active hydrogen compound represented by the chemical formula (1) and the process for the preparation thereof. Among examples of the active hydrogen compound from which the anion $Z^{r-}$ in the chemical formula (1) is derived, those having an active hydrogen atom on an oxygen atom include water; carboxylic acids having 1 to 20 carbon atoms, such as formic acid, acetic acid, propionic acid, butyric acid, isobutyric acid, lauric acid, stearic acid, oleic acid, phenylacetic acid, dihydrocinnamic acid, cyclohexanecarboxylic acid, benzoic acid, p-methylbenzoic acid and 2-carboxynaphthalene; polycarboxylic acids having 2 to 20 carbon atoms and 2 to 6 carboxyl groups, such as oxalic acid, malonic acid, succinic acid, maleic acid, fumaric acid, adipic acid, itaconic acid, butanetetracarboxylic acid, phthalic acid, isophthalic acid, terephthalic acid, trimellitic acid and pyromellitic acid; carbamic acids such as N,N-diethylcarbamic acid, N-carboxypyrrolidone, N-carboxyaniline and N,N'-dicarboxy-2,4-toluenediamine; alcohols having 1 to 20 carbon atoms, such as methanol, ethanol, n-propanol, isopropanol, n-butyl alcohol, sec-butyl alcohol, tert-butyl alcohol, isopentyl alcohol, tert-pentyl alcohol, n-octyl alcohol, lauryl alcohol, cetyl alcohol, cyclopentanol, cyclohexanol, allyl alcohol, crotyl alcohol, methylvinylcarbinol, benzyl alcohol, 1-phenylethyl alcohol, triphenylcarbinol and cinnamyl alcohol; polyhydric alcohols having 2 to 20 carbon atoms and 2 to 8 hydroxyl groups, such as ethylene glycol, propylene glycol, diethylene glycol, dipropylene glycol, 1,3-propanediol, 1,3-butanediol, 1,4-butanediol, 1,6-hexanediol, 1,4-cyclohexanediol, trimethylolpropane, glycerol, diglycerol, pentaerythritol and dipentaerythritol; saccharides and derivatives thereof, such as glucose, sorbitol, dextrose, fructose and sucrose; aromatic compounds containing 6 to 20 carbon atoms and 1 to 3 hydroxyl groups, such as phenol, 2-naphthol, 2,6-dihydroxynaphthalene and bisphenol A; and poly(alkylene oxide)s having 2 to 8 terminals and containing 1 to 8 hydroxyl groups at the terminals, such as poly(ethylene oxide), poly(propylene oxide), and copolymers thereof.

Among examples of the active hydrogen compound from which the anion $Z^{n-}$ is derived, those containing an active hydrogen atom on a nitrogen atom include aliphatic or aromatic primary amines having 1 to 20 carbon atoms, such as methylamine, ethylamine, n-propylamine, isopropylamine, n-butylamine, isobutylamine, sec-butylamine, tert-butylamine, cyclohexylamine, benzylamine, β-phenylethylamine, aniline, o-toluidine, m-toluidine and p-toluidine; aliphatic or aromatic secondary amines having 2 to 20 carbon atoms, such as dimethylamine, methylethylamine, diethylamine, di-n-propylamine, ethyl-n-butylamine, methyl-sec-butylamine, dipentylamine, dicyclohexylamine, N-methylaniline and diphenylamine; polyamines having 2 to 20 carbon atoms and 2 to 3 primary or secondary amino groups, such as ethylenediamine, di(2-aminoethyl)amine, hexamethylenediamine, 4,4'-diaminodiphenylmethane, tri(2-aminoethyl)amine, N,N'-dimethylethylenediamine, N,N'-diethylethylenediamine and di(2-methylaminoethyl)amine; saturated cyclic secondary amines having 4 to 20 carbon atoms, such as pyrrolidine, piperidine, morpholine and 1,2,3,4-tetrahydroquinoline; unsaturated cyclic secondary amines having 4 to 20 carbon atoms, such as 3-pyrroline, pyrrole, indole, carbazole, imidazole, pyrazole and purine; cyclic polyamines having 4 to 20 carbon atoms and 2 to 3 secondary amino groups, such as piperazine, pyrazine and 1,4,7-triazacyclononane; unsubstituted or N-mono-substituted acid amides having 2 to 20 carbon atoms, such as acetamide, propionamide, N-methylpropionamide, N-methylbenzoic amide and N-ethylstearic amide; cyclic amides of 5- to 7-membered rings, such as 2-pyrrolidone and ε-caprolactam; and imides of dicarboxylic acids having 4 to 10 carbon atoms, such as succinimide, maleimide and phthalimide.

The above-mentioned active hydrogen compounds include those containing plural active hydrogen atoms. These active hydrogen atoms can be eliminated either entirely or only in part to derive an anion. The integer n in the chemical formula (1) ranges from 1 to 8, with 1 to 3 being preferred.

Among these active hydrogen compounds, preferred examples are water; alcohols having 1 to 20 carbon atoms, such as methanol, ethanol, n-propanol, isopropanol, n-butyl alcohol, sec-butyl alcohol, tertbutyl alcohol, isopentyl alcohol, tert-pentyl alcohol, n-octyl alcohol, lauryl alcohol, cetyl alcohol, cyclopentanol, cyclohexanol, allyl alcohol, crotyl alcohol, methylvinylcarbinol, benzyl alcohol, 1-phenylethyl alcohol, triphenylcarbinol and cinnamyl alcohol; polyhydric alcohols having 2 to 20 carbon atoms and 2 to 8 hydroxyl groups, such as ethylene glycol, propylene glycol, diethylene glycol, dipropylene glycol, 1,3-propanediol, 1,3-butanediol, 1,4-butanediol, 1,6-hexanediol, 1,4-cyclohexanediol, trimethylolpropane, glycerol, diglycerol, pentaerythritol and dipentaerythritol; saccharides and derivatives thereof, such as glucose, sorbitol, dextrose, fructose and sucrose; poly(alkylene oxide)s having 2 to 8 terminals, containing 1 to 8 hydroxyl groups at the terminals and having a molecular weight of from 100 to 50,000, such as poly(ethylene oxide), poly(propylene oxide), and copolymers thereof; polyamines having 2 to 20 carbon atoms and 2 to 3 primary or secondary amino groups, such as ethylenediamine, di(2-aminoethyl)amine, hexamethylenediamine, 4,4'-diaminodiphenylmethane, tri(2-aminoethyl)amine, N,N'-dimethylethylenediamine, N,N'-diethylethylenediamine and di(2-methylaminoethyl)amine; saturated cyclic secondary amines having 4 to 20 carbon atoms, such as pyrrolidine, piperidine, morpholine and 1,2,3,4-tetrahydroquinoline; and cyclic polyamines having 4 to 20 carbon atoms and 2 to 3 secondary amino groups, such as piperazine, pyrazine and 1,4,7-triazacyclononane.

More preferred examples are water; alcohols having 1 to 10 carbon atoms, such as methanol, ethanol, n-propanol, isopropanol, n-butyl alcohol, sec-butyl alcohol, tert-butyl alcohol, isopentyl alcohol, tert-pentyl alcohol and n-octyl alcohol; polyhydric alcohols having 2 to 10 carbon atoms and 2 to 4 hydroxyl groups, such as ethylene glycol, propylene glycol, 1,4-butanediol, trimethylolpropane, glycerol and pentaerythritol; poly(alkylene oxide)s having 2 to 6 terminals, containing 2 to 6 hydroxyl groups at the terminals and having a molecular weight of from 100 to 10,000, such as poly(ethylene oxide), poly(propylene oxide), and copolymers thereof; polyamines having 2 to 10 carbon atoms and 2 to 3 secondary amino groups, such as N,N'-dimethylethylenediamine, N,N'-diethylethylenediamine and di(2-methylaminoethyl)amine; saturated cyclic secondary amines having 4 to 10 carbon atoms, such as pyrrolidine, piperidine, morpholine and 1,2,3,4-tetrahydroquinoline; and cyclic polyamines having 4 to 10 carbon atoms and 2 to 3 secondary amino groups, such as piperazine, pyrazine and 1,4,7-triazacyclononane.

a, b, c and d in the phosphazenium cations represented by the chemical formula (1) and chemical formula (3) in the present invention are each a positive integer of 3 or smaller or 0 with the proviso that they are not all 0 at the same time. Preferably, they are each a positive integer of 2 or smaller or 0. More preferably, a, b, c and d are, irrespective of the order thereof, values of a combination of (2,1,1,1), (1,1,1,1), (0,1,1,1), (0,0,1,1) or (0,0,0,1), still more preferably values of a combination of (1,1,1,1), (0,1,1,1), (0,0,1,1) or (0,0,0,1).

Rs in the phosphazenium cations of the salts, which are represented by the chemical formula (1) and chemical formula (3) in the present invention, are hydrocarbon groups having 1 to 10 carbon atoms, which may be the same or different. Specifically, R can be selected from aliphatic or aromatic hydrocarbon groups such as methyl, ethyl, n-propyl, isopropyl, allyl, n-butyl, sec-butyl, tert-butyl, 2-butenyl, 1-pentyl, 2-pentyl, 3-pentyl, 2-methyl-1-butyl, isopentyl, tert-pentyl, 3-methyl-2-butyl, neopentyl, n-hexyl, 4-methyl-2-pentyl, cyclopentyl, cyclohexyl, 1-heptyl, 3-heptyl, 1-octyl, 2-octyl, 2-ethyl-1-hexyl, 1,1-dimethyl-3,3-dimethylbutyl (generally called "tert-octyl"), nonyl, decyl, phenyl, 4-tolyl, benzyl, 1-phenylethyl and 2-phenylethyl. Among these, aliphatic hydrocarbon groups having 1 to 10 carbon atoms, such as methyl, ethyl, n-propyl, isopropyl, tert-butyl, tert-pentyl and 1,1-dimethyl-3,3-dimethylbutyl, are preferred, with methyl and ethyl being more preferred.

When two Rs on a common nitrogen atom in the phosphazenium cation are coupled together to form a ring structure, the resultant divalent substituent on the nitrogen atom is a divalent hydrocarbon group whose backbone has 4 to 6 carbon atoms (so that the ring is a 5- to 7-membered ring containing the nitrogen atom). Preferred examples of the divalent hydrocarbon group include tetramethylene, pentamethylene and hexamethylene. Also included are those obtained by substituting such backbones with one or more alkyl groups such as methyl or ethyl group. More preferred examples are tetramethylene and pentamethylene. Either all the available nitrogen atoms in the phosphazenium cation or only a part of the nitrogen atoms may take such a ring structure.

The phosphazenium salt of the active hydrogen compound represented by the chemical formula (1) in the present invention can be obtained by reacting the salt of the phosphazenium cation and the inorganic anion, said salt being represented by the chemical formula (3), with the alkali metal salt of the active hydrogen compound represented by $M^+{}_n Z^{n-}$. In this case, the range of the integer n and the anion $Z^{n-}$ of the active hydrogen compound are the same as those defined above with respect to the chemical formula (1). $M^+{}_n$ represents n alkali metal cations.

The alkali metal salt of the active hydrogen compound represented by $M^+{}_n Z^{n-}$, can be obtained by using a conventional process that reacts the above-mentioned active hydrogen compound with a metallic alkali metal or with a basic alkali metal compound. Examples of the metallic alkali metal include metallic lithium, metallic sodium, metallic potassium and metallic cesium. Illustrative of the basic alkali metal compound are alkali metal amides such as sodium amide and potassium amide; organic alkali metal compounds such as n-propyl lithium, n-butyl lithium, vinyl lithium, cyclopentadienyl lithium, α-naphthyl lithium, ethynyl sodium, n-butyl sodium, phenyl lithium, cyclopentadienyl sodium, fluorenyl sodium, tetraphenylethylene disodium, sodium naphthalenide, ethyl potassium, cyclopentadienyl potassium, phenyl potassium and benzylpotassium; alkali metal hydride compounds such as sodium hydride and potassium hydride; alkali metal hydroxides such as lithium hydroxide, sodium hydroxide, potassium hydroxide and cesium hydroxide; and alkali metal carbonates such as lithium carbonate, sodium carbonate and potassium carbonate. A suitable metallic alkali metal or basic alkali metal compound can be chosen depending on the strength of the acidity of the active hydrogen compound. In some instances, the alkali metal salt of the active hydrogen compound, said salt having been obtained as described above, may act as a basic alkali metal compound so that another active hydrogen compound can be converted into its alkali metal salt.

In the case of an active hydrogen compound having plural active hydrogen atoms, these active hydrogen atoms may all be liberated to convert the active hydrogen compound into an anion upon its reaction with the metallic alkali metal or basic alkali metal compound or as an alternative, only a part of the active hydrogen atoms may be liberated to form an anion.

As the alkali metal cation or cations of the alkali metal salt of the active hydrogen compound, said salt having been obtained as described above and being represented by $M^+{}_n Z^{n-}$, lithium, sodium or potassium cations are preferred.

In the present invention, $X^{m-}$ in the chemical formula (3) represents an inorganic anion whose valence is m. The valence m ranges from 1 to 3. Illustrative of the inorganic anion are anions of inorganic acids such as boric acid; tetrafluoroboric acid; hydrocyanic acid; thiocyanic acid; hydrohalogenic acids such as hydrofluoric acid, hydrochloric acid and hydrobromic acid; nitric acid; sulfuric acid; phosphoric acid; phosphorous acid; hexafluorophosphoric acid; carbonic acid, hexafluoroantimonic acid; hexafluorothallic acid; and perchloric acid. Further, $HSO_4^-$ and $HCO_3^-$ can also be mentioned as inorganic anions.

In some instances, these inorganic anions can be interchanged with each other. Among these inorganic anions, anions of boric acid, tetrafluoroboric acid, hydrohalogenic acids, phosphoric acid, hexafluoric acid, perchloric acid and the like are preferred, with a chloride anion being more preferred.

Concerning the process according to the present invention for the synthesis of the salt of the phosphazenium cation and the inorganic anion, said salt being represented by the chemical formula (3), the following procedures can be mentioned as a general example:

(i) One equivalent of phosphorus pentachloride and 3 equivalents of a di-substituted amine ($HNR_2$) are reacted. After reacted further with 1 equivalent of ammonia, the reaction product is treated with a base to synthesize a 2,2,2-tris(di-substituted amino)-$2\lambda^5$-phosphazene represented by the following chemical formula (8):

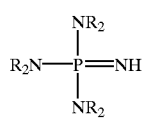

(8)

(ii) A bis(di-substituted amino)[tris(di-substituted amino)phosphoranilideneamino]phosphine oxide, which has been obtained by reacting the above phosphazene compound of the chemical formula (8) and a bis(di-substituted amino)phosphochloridate $\{(R_2N)_2\text{-P(O)Cl}\}$, is chlorinated with phosphorus oxychloride. After reacted with ammonia, the reaction product is treated with a base to obtain 2,2,4,4,4-pentakis-(di-substituted amino)-$2\lambda^5$, $4\lambda^5$-phosphazene represented by the following chemical formula (9):

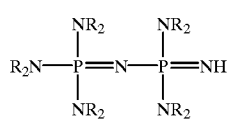

(9)

(iii) The above phosphazene compound of the chemical formula (9) is used instead of the phosphazene compound pound of the chemical formula (8) employed in the procedures (ii) and is reacted as in the procedures (ii), so that an oligophosphazene, which is represented by the following chemical formula (10):

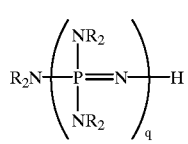

(10)

wherein q stands for 3, is obtained. The compound of the chemical formula (10) in which q stands for 0 or an integer of from 1 to 3, when q=0 represents a di-substituted amine, when q=1 represents the compound of the chemical formula (8), when q=2 represents the compound of chemical formula (9), and when q=3 represents the oligophosphazene obtained in the procedures (iii).

(iv) Compounds with different qs and/or Rs in the chemical formula (10) are successively reacted or a compound of the same q and R in the chemical formula (10) is reacted at once in an amount of totally 4 equivalents with one equivalent of phosphorus pentachloride, whereby a desired salt of a phosphazenium cation and a chloride anion, said salt having the chemical formula (3) in which m is 1 and $X^{m-}$ is $Cl^-$, is obtained. When desired to obtain a salt with an inorganic anion other than a chloride anion, ion exchange can be performed by a conventional method, for example, by conducting treatment with a salt of an alkali metal cation and the desired inorganic anion or by using an ion-exchange resin. A general salt of a phosphazenium cation and inorganic anion represented by the chemical formula (3) can be thus obtained.

The target phosphazenium salt of the active hydrogen compound represented by the chemical formula (1) is prepared by reacting the two salts with each other, namely, the salt of the phosphazenium cation and the inorganic anion, said salt having been obtained as described above and being represented by the chemical formula (3), with the alkali metal salt of the active hydrogen compound represented by $M^+{}_n Z^{n-}$. Here, a salt of the alkali metal cation and the inorganic anion is by-produced. Upon conducting this reaction, no particular limitation is imposed on the ratio of the two salts to be used as the raw materials. No particular problem or inconvenience would arise even if one of the salts is used in excess of the other. In general, however, per equivalent of the salt of the phosphazenium cation and the inorganic anion, the alkali metal salt of the active hydrogen compound can be used in a range of from 0.2 to 5 equivalents, preferably from 0.5 to 3 equivalents, more preferably from 0.7 to 1.5 equivalents. A solvent is usually employed to permit their effective contact. Any solvent can be used as such a reaction solvent insofar as it does not impair the reaction. Examples include water; alcohols such as methanol, ethanol and propanol; ketones such as acetone and methyl ethyl ketone; aliphatic or aromatic hydrocarbons such as n-pentane, n-hexane, cyclohexane, benzene, toluene and xylene; halogenated hydrocarbons such as dichloromethane, chloroform, bromoform, carbon tetrachloride, dichloroethane, chlorobenzene, o-dichlorobenzene, fluorobenzene and benzotrifluoride; esters such as ethyl acetate, methyl propionate and methyl benzoate; ethers such as diethyl ether, tetrahydrofuran, 1,4-dioxane, ethylene glycol dimethyl ether, triethylene glycol dimethyl ether; tertiary amines such as tributylamine, N,N-dimethylaniline, pyridine and quinoline, nitroalkanes such as nitromethane and nitroethane; nitriles such as acetonitrile and propionitrile; and polar aprotic solvents, for example, N,N-dimethylformamide, dimethylsulfoxide, sulfolane, hexamethylphosphoric triamide, and 1,3-dimethyl-2-imidazolidinone. From these solvents, a suitable one is chosen depending on the chemical stabilities of the salts employed as the raw materials in the reaction. These solvents can be used either singly or in combination. The salts as the raw materials can preferably be in the form of a solution, but no problem or inconvenience would arise even when they are in the form of a suspension. The temperature of the reaction varies depending on the kinds, amounts, concentrations and the like of the salts as the raw materials. However, the reaction temperature is generally 150° C. or lower, preferably in a range of from −78 to 80° C., more preferably in a range of from 0 to 50° C. Concerning the reaction pressure, the reaction can be performed under a reduced pressure, normal pressure or an elevated pressure. However the reaction pressure may preferably range from 0.1 to 10 kg/cm² (absolute pressure; this will hereinafter apply equally), with a range of from 1 to 3 kg/cm² being more preferred. The reaction time varies depending on the reaction time and the state of the reaction system, but may be in a range of from 1 minute to 24 hours, preferably from 1 minute to 10 hours, more preferably from 5 minutes to 6 hours.

To separate the target phosphazenium salt of the active hydrogen compound from the reaction mixture, conventional methods can be used. Depending on the kind of the target salt, the kinds of the two salts as raw materials, the excess rate of one of the salts over the other, the kind and amount of the solvent, etc., a suitable method can be chosen from the conventional methods. As the by-produced salt of the alkali metal cation and the inorganic anion usually precipitates as a solid, the reaction mixture is subjected to liquid-solid separation by filtration, centrifugation or the like either as is or after being somewhat concentrated to remove the by-produced salt. The filtrate is then concentrated to dryness, whereby the target salt can be obtained. If the by-produced salt is still dissolved even after the reaction mixture is concentrated, either the by-produced salt or the target salt can be caused to precipitate by adding a poor solvent to the thus-concentrated reaction mixture or after concentrating it further. Alternatively, the by-produced salt and the target salt can also be separated from each other by a method, for example, by extracting one of the salts after concentration to dryness. When one of the raw materials, which was used in excess, is contained at a high concentration in the target salt, they can be separated from each other by extracting the target salt, as is, with a solvent or by extracting the target salt with a solvent subsequent to its re-dissolution in a solvent different from the extracting solvent. The target salt can be purified further by recrystallization, column chromatography or the like as needed. The target salt, namely, the phosphazenium salt of the active hydrogen compound represented by the chemical formula (1) is generally obtained as a liquid of high viscosity or a solid.

The phosphazenium salt of the active hydrogen compound of the chemical formula (1), thus obtained, is extremely useful as an active species for an organic synthesis reaction in which the anion of the active hydrogen compound takes part.

In further aspects of the present invention, there are also provided the phosphazenium hydroxide represented by the chemical formula (2) and its preparation process. In the chemical formula (2) or chemical formula (4), a, b, c and d individually stands for 0 or 1 with the proviso that they are not all 0 at the same time. Preferably, a, b, c and d are, irrespective of the order thereof, values of a combination of (1,1,1,1), (0,1,1,1), (0,0,1,1) or (0,0,0,1).

The phosphazenium hydroxide represented by the chemical formula (2) is prepared from its precursor, that is, the salt of the phosphazenium cation and the monovalent inorganic anion, said salt being represented by the chemical formula (4), by the process which makes use of the ion-exchange resin. As a process for the synthesis of the precursor, the following process can be mentioned as a general example:

(i) One equivalent of phosphorus pentachloride and 3 equivalents of dimethylamine ($Me_3NH$) are reacted. After reacted further with 1 equivalent of ammonia, the reaction product is treated with a base to synthesize 2,2,2-tris(dimethylamino)-2λ$^5$-phosphazene represented by the following chemical formula (11):

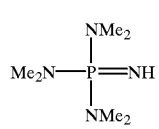

(11)

(ii) At such a molar ratio of dimethylamine to the phosphazene of the chemical formula (11) that corresponds to the values of a, b, c and d in the chemical formula (2), phosphorus pentachloride and dimethylamine are first reacted, followed by the reaction of the phosphazene to the remaining portion of the phosphorus pentachloride. Where a, b, c and d in the chemical formula (2) is, for example, the combination of (1,1,1,1), one equivalent of phosphorus pentachloride and 4 equivalents of the phosphazene of the chemical formula (11) are reacted. In the case of the combination of (0,0,1,1), one equivalent of phosphorus pentachloride and 2 equivalents of dimethylamine are first reacted with each other, followed by the reaction of 2 equivalents of the phosphazene of the chemical formula (11). To the phosphorus pentachloride, the dimethylamine and phosphazene are therefore reacted in a total amount of 4 equivalents. In this manner, phosphazenium chloride of the chemical formula (4) in which Y$^-$ is Cl$^-$ is obtained.

(iii) To replace the chloride anion of this phosphazenium chloride with another inorganic anion Y$^-$, a conventional method such as treatment with a salt of an alkali metal cation and the inorganic anion can be used. A general salt of a phosphazenium cation and inorganic anion, said salt being represented by the chemical formula (4), can generally be thus obtained as described above.

As the monovalent inorganic anion Y$^-$ in the chemical formula (4), an anion of a monovalent inorganic acid selected from the group consisting of hydrochloric acid, tetrafluoroboric acid, hexafluorophosphoric acid and perchloric acid can be mentioned.

The salt of the phosphazenium cation and the monovalent inorganic anion, said salt being represented by the chemical formula (4), is subjected to ion-exchange by an ion-exchange resin to convert it into the phosphazenium hydroxide represented by the chemical formula (2). Upon this ion-exchange, the salt of the phosphazenium cation and the monovalent inorganic anion(s) is dissolved in a mixed solvent of water and a water-miscible organic solvent.

Preferred examples of the water-miscible organic solvent include alcohols such as methanol, ethanol, propanol and butanol; ethers such as dioxane, tetrahydrofuran, 1,2-diethoxymethane, 1,2-diethoxyethane and diethylene glycol dimethyl ether; and nitriles such as acetonitrile and propionitrile. In addition, any other organic solvents can also be used insofar as they do not inhibit the ion-exchange to the phosphazenium hydroxide and they are miscible with water. In the mixed solvent of water and the water-miscible organic solvent, the proportion of the water-miscible organic solvent can range generally from 5 to 95 wt. %, preferably from 30 to 90 wt. %, more preferably from 50 to 85 wt. %.

The concentration of the salt of the phosphazenium cation and the monovalent inorganic anion, said salt being represented by the chemical formula (4), in the mixed solvent, may generally range from 0.01 to 5 M (M stands for mol/l; this will equally apply hereinafter), with a range of from 0.05 to 1 M being preferred.

The above-employed ion-exchange resin is a hydroxide-form anion-exchange resin and its cationic groups are usually of the tertiary amine type or quaternary ammonium type. The ion-exchange resin is usually employed in a form packed in a column, although it can be directly brought into contact with the salt of the phosphazenium cation and the monovalent inorganic anion in a solution of the salt. The ion-exchange resin is used in such an amount that the exchanging capacity of the resin ranges from 1 to 100 times, preferably from 1.5 to 20 times the equivalent of the monovalent anion to be exchanged.

When causing a solution of the salt of the chemical formula (4) to flow through the column, the flow rate is generally 0.02 to 200 l/hour, preferably 0.1 to 100 l/hour per liter of the hydroxide-form anion-exchange resin.

The temperature upon ion-exchange varies depending on the ion-exchange resin to be used. It is generally from 10 to 80° C., preferably from 20 to 40° C.

From a solution obtained after a separating operation such as filtration when the ion-exchange resin is directly brought into contact with the salt in its solution or from an effluent itself when the ion-exchange resin is used in the column, the target phosphazenium hydroxide is obtained by distilling off the solvent to dryness.

The phosphazenium hydroxide of the chemical formula (2) obtained as described above has high solubility in organic solvents as well as in water and also has strong basicity. (For example, 0.1 M and 0.01 M aqueous solutions of tetrakis[tris(dimethylamino)phosphoranilideneamino] phosphonium hydroxide, namely, a compound of the chemical formula (2) in which a, b, c and d are (1,1,1,1) exhibit pH values of 13.3 and 12.5, respectively, and 0.1 M and 0.01 M aqueous solutions of (dimethylamino)tris[tris (dimethylamino)phosphoranilideneamino]phosphonium hydroxide, namely, a compound of the formula (2) in which a, b, c and d are (0,1,1,1) exhibit pH values of 13.5 and 12.6, respectively.) Hence, the phosphazenium hydroxide of the chemical formula (2) effectively eliminates one or more protons from each of various active hydrogen compounds so that an anion of the active hydrogen compound is produced. And the anion thus formed possesses high nucleophilicity. As is readily understood from the foregoing, the phosphazenium hydroxide of the chemical formula (2) is extremely useful as a base in organic synthesis reactions.

In a still further aspect of the present invention, there is also provided the process for the production of the poly (alkylene oxide), which comprises polymerizing the alkylene oxide compound in the presence of:

(I-i) (a) the salt of the phosphazenium cation and the inorganic anion, said salt being represented by the chemical formula (5) or chemical formula (6), and
  (b) the alkali metal or alkaline earth metal salt of the active hydrogen compound, or
(I-ii) the phosphazenium salt of the active hydrogen compound, said phosphazenium salt having been derived from:
  (a) the salt of the phosphazenium cation and the inorganic anion, said salt being represented by the chemical formula (5), and
  (b) the alkali metal or alkaline earth metal salt of the active hydrogen compound; or
(II-i) (a) the phosphazenium compound represented by the formula (7), and
  (b) the active hydrogen compound, or
(II-ii) the phosphazenium salt of the active hydrogen compound, said phosphazenium salt having been derived from:

(a) the phosphazenium compound represented by the chemical formula (7), and (b) the active hydrogen compound.

Illustrative of the alkylene oxide compound in the process according to the present invention are epoxy compounds such as ethylene oxide, propylene oxide, 1,2-butylene oxide, 2,3-butylene oxide, styrene oxide, cyclohexene oxide, epichlorohydrin, epibromohydrin, methyl glycidyl ether, allyl glycidyl ether and phenyl glycidyl ether. These alkylene oxide compounds can be used in combination. When used in combination, plural alkylene oxide compounds can be simultaneously used in combination, can be successively used in combination, or successively and repeatedly used in combination.

Among these alkylene oxide compounds, ethylene oxide, propylene oxide, 1,2-butylene oxide and styrene oxide are preferred, with ethylene oxide and propylene oxide being more preferred.

a, b, c and d in the phosphazenium cations represented by the chemical formula (5) and chemical formula (7) in the present invention are each a positive integer of 3 or smaller or 0 with the proviso that they are not all 0 at the same time. Preferably, they are each a positive integer of 2 or smaller or 0. More preferably, a, b, c and d are, irrespective of the order thereof, values of a combination of (2,1,1,1), (1,1,1,1), (0,1,1,1), (0,0,1,1) or (0,0,0,1), still more preferably values of a combination of (1,1,1,1), (0,1,1,1), (0,0,1,1) or (0,0,0,1).

Further, e, f and g in the phosphazenium cation represented by the chemical formula (6) are each a positive integer of 3 or smaller or 0 with the proviso that they are not all 0 at the same time. Preferably, they are each a positive integer of 2 or smaller or 0. More preferably, e, f and g are, irrespective of the order thereof, values of a combination of (2,1,1), (1,1,1), (0,1,1), or (0,0,1).

Rs in the phosphazenium cations of the salts, which are represented by the chemical formula (5), chemical formula (6) and chemical formula (7), are hydrocarbon groups having 1 to 10 carbon atoms, which may be the same or different. Specifically, R can be selected from aliphatic or aromatic hydrocarbon groups such as methyl, ethyl, n-propyl, isopropyl, allyl, n-butyl, sec-butyl, tert-butyl, 2-butenyl, 1-pentyl, 2-pentyl, 3-pentyl, 2-methyl-1-butyl, isopentyl, tert-pentyl, 3-methyl-2-butyl, neopentyl, n-hexyl, 4-methyl-2-pentyl, cyclopentyl, cyclohexyl, 1-heptyl, 3-heptyl, 1-octyl, 2-octyl, 2-ethyl-1-hexyl, 1,1-dimethyl-3,3-dimethylbutyl (generally called "tert-octyl"), nonyl, decyl, phenyl, 4-tolyl, benzyl, 1-phenylethyl and 2-phenylethyl. Among these, aliphatic hydrocarbon groups having 1 to 10 carbon atoms, such as methyl, ethyl, n-propyl, isopropyl, tert-butyl, tert-pentyl, 1-octyl and 1,1-dimethyl-3,3-dimethylbutyl, are preferred.

When two Rs on a common nitrogen atom in the phosphazenium cation are coupled together to form a ring structure, the resultant divalent hydrocarbon group on the nitrogen atom is a divalent hydrocarbon group having a backbone composed of 4 to 6 carbon atoms (so that the ring is a 5- to 7-membered ring containing the nitrogen atom). Preferred examples of the divalent hydrocarbon groups include tetramethylene, pentamethylene and hexamethylene. Also included are those obtained by substituting such backbones with one or more alkyl groups such as methyl or ethyl group. More preferred examples are tetramethylene and pentamethylene. Either all the available nitrogen atoms in the phosphazenium cation or only a part of the nitrogen atoms may take such a ring structure.

A description will next be made about one of the processes according to the present invention for the production of a poly(alkylene oxide), namely, about the production of a poly(alkylene oxide) by polymerizing an alkylene oxide compound in the presence of the salt of the phosphazenium cation and the inorganic anion(s), said salt being represented by the chemical formula (5) or chemical formula (6), and the alkali metal or alkaline earth metal salt of the active hydrogen compound or in the presence of the phosphazenium salt of the active hydrogen compound derived from the phosphazenium cation and the inorganic anion, said salt being represented by the chemical formula (5), and the alkali metal or alkaline earth metal salt of the active hydrogen compound.

$T^{r-}$ in the chemical formula (5) or chemical formula (6) represents an inorganic anion whose valence is r. Here, r is an integer of from 1 to 3. Examples of such an inorganic anion include anions of inorganic acids, for example, boric acid; tetrafluoroboric acid; hydrocyanic acid; thiocyanic acid; hydrohalogenic acids such as hydrofluoric acid, hydrochloric acid and hydrobromic acid; nitric acid; sulfuric acid; phosphoric acid; phosphorous acid; hexafluorophosphoric acid; carbonic acid; hexafluoroantimonic acid; hexafluorothallic acid; and perchloric acid. Further, $HSO_4^-$ and $HCO_3^-$ can also be mentioned as inorganic anions.

In some instances, these inorganic anions can be interchanged with each other. Among these inorganic anions, anions of boric acid, tetrafluoroboric acid, hydrohalogenic acids, phosphoric acid, hexafluoric acid, perchloric acid and the like are preferred, with a chloride anion being more preferred.

A general process for the synthesis of the salt of the phosphazenium cation and the inorganic anion, said salt being represented by the chemical formula (5), is the same as the above-described process for the synthesis of the salt of the phosphazenium cation and the inorganic anion, said salt being represented by the chemical formula (3).

On the other hand, the salt of the phosphazenium cation and the inorganic anion(s), said salt being represented by the chemical formula (6), can generally be synthesized by the following process:

(i) Phosphorus pentachloride and a mono-substituted amine ($RNH_2$) are reacted to obtain a trichlorophosphazene represented by the following chemical formula (12):

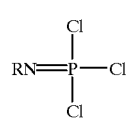

(12)

(ii) The above-described compounds represented by the chemical formula (10) with different qs and/or Rs are successively reacted or the compound represented by the chemical formula (10) of the same q and R is reacted at once in an amount of 3 equivalents with one equivalent of the trichlorophosphazene of the chemical formula (12), whereby a desired salt of a phosphazenium cation and a chloride anion, said salt having the chemical formula (6) in which r is 1 and $T^{r-}$ is $Cl^-$, is obtained.

When desired to obtain a salt with an inorganic anion other than a chloride anion, ion exchange can be performed by a conventional method, for example, by conducting treatment with a salt of an alkali metal cation and the desired inorganic anion or by using an ion-exchange resin. A general salt of a phosphazenium cation and inorganic anion represented by the chemical formula (6) can be thus obtained.

Further, some of salts represented by the chemical formula (6) can also be obtained by causing the above-mentioned inorganic acid to act on some commercially-available phosphazene compounds, for example, a compound represented by the following chemical formula (13):

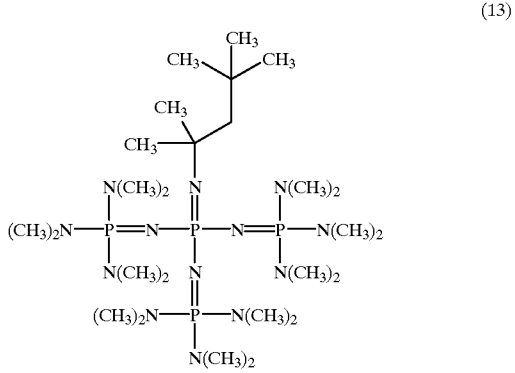

namely, 1-(1,1,3,3-tetramethylbutyl)-4,4,4-tris-(dimethylamino)-2,2-bis[tris(dimethylamino) phosphoranilideneamino]-2λ$^5$, 4λ$^5$-catenadi(phosphazene)

The alkali metal or alkaline earth metal salt of the active hydrogen compound, which is caused to exist together with the salt of the chemical formula (5) or chemical formula (6), means a salt in the form that one or more active hydrogen atoms of the active hydrogen compound have been eliminated and substituted by alkali metal or alkaline earth metal ions. Examples of the active hydrogen compound capable for yielding such a salt include water; carboxylic acids having 1 to 20 carbon atoms, such as formic acid, acetic acid, propionic acid, butyric acid, isobutyric acid, lauric acid, stearic acid, oleic acid, phenylacetic acid, dihydrocinnamic acid, cyclohexanecarboxylic acid, benzoic acid, p-methylbenzoic acid and 2-carboxynaphthalene; polycarboxylic acids having 2 to 20 carbon atoms and 2 to 6 carboxyl groups, such as oxalic acid, malonic acid, succinic acid, maleic acid, fumaric acid, adipic acid, itaconic acid, butanetetracarboxylic acid, phthalic acid, isophthalic acid, terephthalic acid, trimellitic acid and pyromellitic acid; carbamic acids such as N,N-diethylcarbamic acid, N-carboxypyrrolidone, N-carboxyaniline and N,N'-dicarboxy-2,4-toluenediamine; alcohols having 1 to 20 carbon atoms, such as methanol, ethanol, n-propanol, isopropanol, n-butyl alcohol, sec-butyl alcohol, tert-butyl alcohol, isopentyl alcohol, tert-pentyl alcohol, n-octyl alcohol, lauryl alcohol, cetyl alcohol, cyclopentanol, cyclohexanol, allyl alcohol, crotyl alcohol, methylvinylcarbinol, benzyl alcohol, 1-phenylethyl alcohol, triphenylcarbinol and cinnamyl alcohol; polyhydric alcohols having 2 to 20 carbon atoms and 2 to 8 hydroxyl groups, such as ethylene glycol, propylene glycol, diethylene glycol, dipropylene glycol, 1,3-propanediol, 1,3-butanediol, 1,4-butanediol, 1,6-hexanediol, 1,4-cyclohexanediol, trimethylolpropane, glycerol, diglycerol, pentaerythritol and dipentaerythritol; saccharides and derivatives thereof, such as glucose, sorbitol, dextrose, fructose and sucrose; aromatic compounds containing 6 to 20 carbon atoms and 1 to 3 hydroxyl groups, such as phenol, 2-naphthol, 2,6-dihydroxynaphthalene and bisphenol A; and poly(alkylene oxide)s having 2 to 8 terminals, containing 1 to 8 hydroxyl groups at the terminals, such as poly(ethylene oxide), poly (propylene oxide), and copolymers thereof.

Also included are aliphatic or aromatic primary amines having 1 to 20 carbon atoms, such as methylamine, ethylamine, n-propylamine, isopropylamine, n-butylamine, isobutylamine, sec-butylamine, tert-butylamine, cyclohexylamine, benzylamine, β-phenylethylamine, aniline, o-toluidine, m-toluidine and p-toluidine; aliphatic or aromatic secondary amines having 2 to 20 carbon atoms, such as dimethylamine, methylethylamine, diethylamine, di-n-propylamine, ethyl-n-butylamine, methyl-sec-butylamine, dipentylamine, dicyclohexylamine, N-methylaniline and diphenylamine; polyamines having 2 to 20 carbon atoms and 2 to 3 primary or secondary amino groups, such as ethylenediamine, di(2-aminoethyl)amine, hexamethylenediamine, 4,4'-diaminodiphenylmethane, tri (2-aminoethyl)amine, N,N'-dimethylethylenediamine and di(2-methylaminoethyl)amine; saturated cyclic secondary amines having 4 to 20 carbon atoms, such as pyrrolidine, piperidine, morpholine and 1,2,3,4-tetrahydroquinoline; unsaturated cyclic secondary amines having 4 to 20 carbon atoms, such as 3-pyrroline, pyrrole, indole, carbazole, imidazole, pyrazole and purine; cyclic polyamines having 4 to 20 carbon atoms and 2 to 3 secondary amino groups, such as piperazine, pyrazine and 1,4,7-triazacyclononane; unsubstituted or N-mono-substituted acid amides having 2 to 20 carbon atoms, such as acetamide, propionamide, N-methylpropionamide, N-methylbenzoic amide and N-ethylstearic amide; cyclic amides of 5- to 7-membered rings, such as 2-pyrrolidone and ε-caprolactam; and imides of dicarboxylic acids having 4 to 10 carbon atoms, such as succinimide, maleimide and phthalimides.

The above-mentioned active hydrogen compounds include those containing plural active hydrogen atoms. These active hydrogen atoms may be eliminated entirely as protons to derive an anion having a plural valence in some instances. In other instances, they may be eliminated only in part to derive an anion of a corresponding valence. In the process of the present invention, both instances are included.

Among these active hydrogen compounds, preferred examples are alcohols having 1 to 20 carbon atoms, such as methanol, ethanol, n-propanol, isopropanol, n-butyl alcohol, sec-butyl alcohol, tert-butyl alcohol, isopentyl alcohol, tert-pentyl alcohol, n-octyl alcohol, lauryl alcohol, cetyl alcohol, cyclopentanol, cyclohexanol, allyl alcohol, crotyl alcohol, methylvinylcarbinol, benzyl alcohol, 1-phenylethyl alcohol, triphenylcarbinol and cinnamyl alcohol; polyhydric alcohols having 2 to 20 carbon atoms and 2 to 8 hydroxyl groups, such as ethylene glycol, propylene glycol, diethylene glycol, dipropylene glycol, 1,3-propanediol, 1,3-butanediol, 1,4-butanediol, 1,6-hexanediol, 1,4-cyclohexanediol, trimethylolpropane, glycerol, diglycerol, pentaerythritol and dipentaerythritol; saccharides and derivatives thereof, such as glucose, sorbitol, dextrose, fructose and sucrose; poly (alkylene oxide)s having 2 to 8 terminals, containing 1 to 8 hydroxyl groups at the terminals and having a molecular weight of from 100 to 50,000, such as poly(ethylene oxide), poly(propylene oxide), and copolymers thereof; polyamines having 2 to 20 carbon atoms and 2 to 3 primary or secondary amino groups, such as ethylenediamine, di(2-aminoethyl) amine, hexamethylenediamine, 4,4'-diaminodiphenylmethane, tri(2-aminoethyl)amine, N,N'-dimethylethylenediamine and di(2-methylaminoethyl) amine; saturated cyclic secondary amines having 4 to 10 carbon atoms, such as pyrrolidine, piperidine, morpholine and 1,2,3,4-tetrahydroquinoline; and cyclic polyamines having 4 to 10 carbon atoms and 2 to 3 secondary amino groups, such as piperazine, pyrazine and 1,4,7-triazacyclononane.

More preferred examples include polyhydric alcohols having 2 to 20 carbon atoms and 2 to 8 hydroxyl groups, such as ethylene glycol, propylene glycol, 1,4-butanediol, glycerol, pentaerythritol and dipentaerythritol; saccharides and derivatives thereof, such as glucose, sorbitol, dextrose, fructose and sucrose; poly(alkylene oxide)s having 2 to 6 terminals, containing 2 to 6 hydroxyl groups at the terminals and having a molecular weight of from 100 to 10,000, such as poly(ethylene oxide), poly(propylene oxide), and copolymers thereof; polyamines having 2 to 20 carbon atoms and 2 to 3 primary or secondary amino groups, such as ethylenediamine, di(2-aminoethyl)amine, hexamethylenediamine, 4,4'-diaminodiphenylmethane, tri(2-aminoethyl)amine, N,N'-dimethylethylenediamine and di(2-methylaminoethyl)amine; and cyclic polyamines having 4 to 10 carbon atoms and 2 to 3 secondary amino groups, such as piperazine, pyrazine and 1,4,7-tri-azacyclononane.

To obtain the alkali metal or alkaline earth metal salt of such an active hydrocarbon compound, a conventional process is used, that is, the active hydrogen compound is reacted with a metallic alkali metal or alkaline earth metal or with a basic alkali metal or alkaline earth metal compound. Illustrative of the metallic alkali metal or alkaline earth metal are metallic lithium, metallic sodium, metallic potassium and metallic cesium, or metallic magnesium, metallic calcium, metallic strontium and metallic barium. Illustrative of the basic alkali metal or alkaline earth metal compound are alkali metal or alkaline earth metal amides such as sodium amide and potassium amide, or magnesium amide and barium amide; organic alkali metal or alkaline earth metal compounds such as n-propyl lithium, n-butyl lithium, vinyl lithium, cyclopentadienyl lithium, a-naphthyl lithium, ethynyl sodium, n-butyl sodium, phenyl sodium, cyclopentadienyl sodium, fluorenyl sodium, tetraphenylethylene disodium, sodium naphthalenide, ethyl potassium, cyclopentadienyl potassium, phenyl potassium and benzylpotassium, or diethyl magnesium, ethylisopropyl magnesium, di-n-butyl magnesium, di-tert-butyl magnesium, vinylmagnesium bromide, phenylmagnesium bromide, dicyclopentadienyl magnesium, dimethyl calcium, calcium acetylide, ethylstrontium bromide, phenylbarium iodide and dicycopentadienyl barium; alkali metal or alkaline earth metal hydride compounds such as sodium hydride and potassium hydride, or calcium hydride and barium hydride; alkali metal or alkaline earth metal hydroxides such as lithium hydroxide, sodium hydroxide, potassium hydroxide and cesium hydroxide, or magnesium hydroxide, calcium hydroxide, strontium hydroxide and barium hydroxide; and alkali metal or alkaline earth metal carbonates such as lithium carbonate, sodium carbonate and potassium carbonate, or magnesium carbonate, calcium carbonate and barium carbonate.

From these metallic alkali or alkaline earth metals and basic alkali metal or alkaline earth metal compounds, a suitable metallic alkali or alkaline earth metal or basic alkali metal or alkaline earth metal compound can be chosen depending on the strength of the acidity of the active hydrogen compound. In some instances, the alkali metal or alkaline earth metal salt of the active hydrogen compound, once formed, may act as a basic alkali metal or alkaline earth metal compound so that another active hydrogen compound can be converted into its alkali metal or alkaline earth salt.

In the case of an active hydrogen compound having plural active hydrogen atoms, these active hydrogen atoms may all be liberated to convert the active hydrogen compound into an anion upon its reaction with the metallic alkali or alkaline earth metal or basic alkali metal or alkaline earth metal compound or as an alternative, only a part of the active hydrogen atoms may be liberated to form an anion.

Among these alkali metal or alkaline earth metal salts of the active hydrogen compound, the alkali metal salts of the active hydrogen compound are preferred. As a cation of such an alkali metal salt of the active hydrogen compound, a cation of an alkali metal selected from lithium, sodium or potassium is preferred.

The alkylene oxide compound is polymerized in the presence of the above-mentioned two types of salts, that is, the salt of the phosphazenium cation and the inorganic anion, said salt being represented by the chemical formula (5) or chemical formula (6), and the alkali metal or alkaline earth metal salt of the active hydrogen compound. Here, a salt of the alkali metal cation and the inorganic anion is byproduced. If the presence of this by-produced salt is inconvenient for the polymerization reaction, the by-produced salt can be removed by a suitable method such as filtration prior to the polymerization reaction. As an alternative, it is also possible to isolate the phosphazenium salt of the active hydrogen compound, which has been derived from the salt represented by the chemical formula (5) and the alkali metal or alkaline earth metal salt of the active hydrogen compound, in advance and then to use for polymerization of the alkylene oxide compound in the presence of the phosphazenium salt of the active hydrogen compound.

As a process for obtaining this the phosphazenium salt of the active hydrogen compound in advance, the salt represented by the chemical formula (5) and the alkali metal or alkaline earth metal salt of the active hydrogen compound are reacted. No particular limitation is imposed on the ratio of the two salts to be used. No particular problem or inconvenience would arise even if one of the salts is used in excess of the other. In general, however, per equivalent of the salt of the phosphazenium cation and the inorganic anion, the alkali metal or alkaline earth metal salt of the active hydrogen compound can be used in a range of from 0.2 to 5 equivalents, preferably from 0.5 to 3 equivalents, more preferably from 0.7 to 1.5 equivalents.

A solvent is usually employed to permit their effective contact. Any solvent can be used as such a reaction solvent insofar as it does not impair the reaction. Examples include water; alcohols such as methanol, ethanol and propanol; ketones such as acetone and methyl ethyl ketone; aliphatic or aromatic hydrocarbons such as n-pentane, n-hexane, cyclohexane, benzene, toluene and xylene; halogenated hydrocarbons such as dichloromethane, chloroform, bromoform, carbon tetrachloride, dichloroethane, chlorobenzene, o-dichlorobenzene, fluorobenzene and benzotrifluoride; esters such as ethyl acetate, methyl propionate and methyl benzoate; ethers such as diethyl ether, tetrahydrofuran, 1,4-dioxane, ethylene glycol dimethyl ether, triethylene glycol dimethyl ether; tertiary amines such as tributylamine, N,N-dimethylaniline, pyridine and quinoline; nitrites such as acetonitrile and propionitrile; and aprotic polar solvents such as N,N-dimethylformamide, dimethylsulfoxide, sulfolane, hexamethylphosphoric triamide, and 1,3-dimethyl-2-imidazolidinone. From these solvents, a suitable one is chosen depending on the chemical stabilities of the salts employed as the raw materials in the reaction. Preferred examples include aromatic hydrocarbons such as benzene, toluene and xylene; ethers such as diethyl ether, tetrahydrofuran, 1,4-dioxane and ethylene glycol dimethyl ether; nitrites such as acetonitrile and propionitrile; and aprotic polar solvents such as N,N-dimethylformamide, dimethylsulfoxide, sulfolane, hexamethylphosphoric triamide, and 1,3-dimethyl- 2-imidazolidinone. These solvents can be used either singly or in combination. The salts as the raw materials can preferably be in the form of a solution, but no problem or inconvenience would arise even when they are in the form of a suspension. The temperature of the reaction varies depending on the kinds, amounts, concentrations and the like of the salts as the raw materials. However, the reaction temperature is generally 150° C. or lower, preferably in a range of from −78 to 80° C., more preferably in a range of from 0 to 50° C. Concerning the reaction pressure, the reaction can be performed under a reduced pressure, normal pressure or an elevated pressure. However the reaction pressure may preferably range from 0.1 to 10 kg/cm$^2$ (absolute pressure; this will hereinafter apply equally), with a range of from 1 to 3 kg/cm$^2$ being more preferred. The reaction time may be in a range of from 1 minute to 24 hours, preferably from 1 minute to 10 hours, more preferably from 5 minutes to 6 hours.

To separate the target phosphazenium salt of the active hydrogen compound from the reaction mixture, conventional methods making use of usual procedures in combination can be used. Depending on the kind of the target salt, the kinds of the two salts as raw materials, the excess rate of one of the salts over the other, the kind and amount of the solvent, etc., a suitable method can be chosen from the conventional methods. As the by-produced salt of the alkali metal or alkaline earth metal cation and the inorganic anion usually precipitates as a solid, the reaction mixture is subjected to liquid-solid separation by filtration, centrifugation or the like either as is or after being somewhat concentrated to remove the by-produced salt. The filtrate is then concentrated to dryness, whereby the target salt can be obtained. If the by-produced salt is still dissolved even after the reaction mixture is concentrated, either the by-produced salt or the target salt can be caused to precipitate by adding a poor solvent to the thus-concentrated reaction mixture or after concentrating it further. Alternatively, the by-produced salt and the target salt can also be separated from each other by a method, for example, by extracting one of the salts after concentration to dryness. When one of the raw materials which was used in excess is contained at a high concentration in the target salt, they can be separated from each other by extracting the target salt, as is, with a solvent or by extracting the target salt with a solvent subsequent to its re-dissolution in a solvent different from the extracting solvent. The target salt can be purified further by recrystallization, column chromatography or the like as needed. The target salt is generally obtained as a liquid of high viscosity or a solid.

In some instances, the polymerization of the alkylene oxide compound can also be conducted by reacting the active hydrogen compound with the metallic alkali metal or alkaline earth metal or with the basic alkali metal or alkaline earth metal compound to obtain the alkali metal or alkaline earth metal salt of the active hydrogen compound and then by adding the salt of the phosphazenium cation and inorganic anion to the reaction mixture without performing any particular isolating operation.

The alkylene oxide compound is polymerized in the presence of the salt of the phosphazenium cation and the inorganic anion, said salt being represented by the chemical formula (5) or chemical formula (6), and the alkali metal or alkaline earth metal salt of the active hydrogen compound or in the presence of the phosphazenium salt of the active hydrogen compound derived from the phosphazenium cation and the inorganic anion, said salt being represented by the chemical formula (5), and the alkali metal or alkaline earth metal salt of the active hydrogen compound. At this time, an active hydrogen compound, which is either the same as or different from the active hydrogen compound in the form of the above-mentioned alkali metal or alkaline earth metal salt or phosphazenium salt, may be allowed to exist additionally in the reaction system unless the polymerization reaction is inhibited. When allowed to exist, no particular limitation is imposed on the amount of the additional active hydrogen compound. However, it may range from $1\times10^{-15}$ to $5\times10^{-1}$ mole, preferably from $1\times10^{-7}$ to $1\times10^{-1}$ mole per mole of the alkylene oxide compound.

When these salts are supplied as solutions, their solvents may be eliminated beforehand by a suitable method such as by heating the solutions under reduced pressure if these solvents are inconvenient for the polymerization reaction.

When polymerizing the alkylene oxide compound in the presence of the salt of the phosphazenium cation and the inorganic anion, said salt being represented by the chemical formula (5) or chemical formula (6), and the alkali metal or alkaline earth metal salt of the active hydrogen compound, no particular limitation is imposed on the ratio of the two salts to be used. However, per equivalent of the salt of the phosphazenium cation and the inorganic anion, the alkali metal or alkaline earth metal salt of the active hydrogen compound can be used generally in a range of from 0.2 to 5 equivalents, with a range of from 0.5 to 3 equivalents being preferred and a range of from 0.7 to 1.5 equivalents being more preferred.

No particular limitation is imposed on the amount of the phosphazenium cation for use in the polymerization reaction of the alkylene oxide compound. No matter whether the phosphazenium cation is in the form of the salt with the inorganic anion(s) or in the form of the salt with the anion of the active hydrogen compound, the phosphazenium cation can be used generally in a range of from $1\times10^{-15}$ to $5\times10^{-1}$ mole, with a range of from $1\times10^{-7}$ to $1\times10^{-2}$ mole being more preferred, both per mole of the alkylene oxide.

No problem or inconvenience would arise even when the salt of the phosphazenium cation and the inorganic anion, said salt being represented by the chemical formula (5) or chemical formula (6), and the alkali metal or alkaline earth metal salt of the active hydrogen compound or the phosphazenium salt of the active hydrogen compound derived from the salt of the phosphazenium cation and the inorganic anion, said salt being represented by the chemical formula (5), and the alkali metal or alkaline earth metal salt of the active hydrogen compound are used in combination with a conventionally-known initiator system with a view to reducing a post-polymerization load such as elimination of the initiator.

A description will now be made about the other process according to the present invention for the production of a poly(alkylene oxide), namely, about the production of a poly(alkylene oxide) by polymerizing an alkylene oxide compound in the presence of the phosphazenium compound represented by the chemical formula (7) and the active hydrogen compound or in the presence of the phosphazenium salt of the active hydrogen compound derived from the phosphazenium compound represented by the formula (7) and the active hydrogen compound.

Q$^-$ in the phosphazenium compound represented by the chemical formula (7) is an anion selected from the group consisting of a hydroxyl anion, alkoxyl anions, aryloxyl anions and carboxyl anions.

Among these Q$^-$ anions, preferred examples include a hydroxyl anion; alkoxyl anions derived from alcohols having 1 to 8 carbon atoms, such as methanol, ethanol, n-propanol, isopropanol, allyl alcohol, n-butanol, sec-butanol, tert-butanol, cyclohexanol, 2-heptanol and 1-octanol; aryloxyl anions derived from aromatic hydroxy compounds having 6 to 18 carbon atoms, such as phenol, cresol, xylenol and naphthol; and carboxyl anions derived from carboxylic acids having 1 to 6 carbon atoms, such as formic acid, acetic acid, propionic acid, butyric acid, isobutyric acid and caproic acid.

Of these, more preferred are a hydroxyl anion; alkoxyl anions derived from saturated alkyl alcohols having 1 to 4 carbon atoms, such as methanol, ethanol, n-propanol, isopropanol, n-butanol, sec-butanol and tert-butanol; aryloxyl anions derived from aromatic hydroxy compounds having 6 to 8 carbon atoms, such as phenol and anisole; and carboxyl anions derived from carboxylic acids having 2 to 4 carbon atoms, such as acetic acid and propionic acid. Still more preferred are a hydroxyl anion, a methoxy anion, an ethoxy anion, and an acetate anion.

These phosphazenium compounds can be used either singly or in combination.

As a general process for the synthesis of the phosphazenium compound represented by the chemical for- mula (7), the phosphazenium chloride of the chemical formula (3) in which m=1 and $X^{m-}=Cl^-$ is synthesized in a similar manner as the above-mentioned synthesis of the salt represented by the chemical formula (3). The chloride anion can then be replaced by a desired anion $Q^-$ by a method that the phosphazenium chloride is treated, for example, with an alkali metal or alkaline earth metal hydroxide, alkoxide, aryloxide or carboxide, by a method making use of an ion-exchange resin, or by a like method. In this manner, the general phosphazenium compound represented by the chemical formula (7) can be obtained.

The active hydrogen compound, which is caused to exist together with the phosphazenium compound of the chemical formula (7), or the active hydrogen compound, which is converted together with the phosphazenium compound of the chemical formula (7) into the phosphazenium salt, is the same as the active hydrogen compound mentioned above in detail in connection with its alkali metal or alkaline earth metal salt.

These active hydrogen compounds include those containing plural active hydrogen atoms. In the process of the present invention, polymerization generally initiates at all anionic sites of such an active hydrogen compound.

In the process of the present invention that the alkylene oxide compound is polymerized in the presence of the phosphazenium compound represented by the chemical formula (7) and the active hydrogen compound or in the presence of the phosphazenium salt of the active hydrogen compound derived form the phosphazenium compound represented by the chemical formula (7) and the active hydrogen compound, an excess portion of the active hydrogen compound which is generally used in excess remains as is upon derivation of the phosphazenium salt of the active hydrogen compound, may remain as is in the polymerization system. In addition, water, an alcohol, an aromatic hydroxy compound or a carboxylic acid is also by-produced depending on the kind of the phosphazenium compound. If necessary, such by-products can be eliminated prior to the polymerization reaction of the alkylene oxide compound. As an elimination method, it is possible to use a method commonly employed in the art, for example, a method that they are distilled off under heat and/or reduced pressure, a method that an inert gas is bubbled through the reaction mixture, or a method making use of an adsorbent. By such an elimination method, the reaction between the phosphazenium compound and the active hydrogen compound may be promoted in some instances.

No problem or inconvenience would arise even when the phosphazenium compound represented by the chemical for- mula (7) and the active hydrogen compound or the phosphazenium salt of the active hydrogen compound derived from them are used in combination with a conventionally-known initiator system with a view to reducing a post-polymerization load such as elimination of the initiator.

No particular limitation is imposed on the amount of the phosphazenium compound of the chemical formula (7) for use in the polymerization reaction of the alkylene oxide compound. However its amount may generally be in a range of from $1 \times 10^{-5}$ to 1 mole, with a range of from $1 \times 10^{-4}$ to $5 \times 10^{-1}$ mole being preferred and a range of from $1 \times 10^{-3}$ to $1 \times 10^{-1}$ mole being more preferred, all per mole of the active hydrogen compound.

Relative to the alkylene oxide compound, no particular limitation is imposed on the amount of the phosphazenium compound, namely, on the amount of the phosphazenium cation. However, its amount can range generally from $1 \times 10^{-15}$ to $5 \times 10^{-1}$ mole, preferably from $1 \times 10^{-7}$ to $5 \times 10^{-2}$ mole, both per mole of the alkylene oxide compound.

Whichever process is employed for the production of the poly(alkylene oxide) in the present invention, no particular limitation is imposed on the manner of the polymerization reaction. In general, a required amount of the alkylene oxide compound is supplied either at once, intermittently or continuously to a reactor in which (I-i) the salt of the phosphazenium cation and the inorganic anion, said salt being represented by the chemical formula (5) or chemical formula (6) and the alkali metal or alkaline earth metal salt of the active hydrogen compound, or (I-ii) the phosphazenium salt of the active hydrogen compound, which has been derived from the salt of the phosphazenium cation and the inorganic anion, said salt being represented by the chemical formula (5), and the alkali metal or alkaline earth metal salt of the active hydrogen compound have been charged together with the additional active hydrogen compound, if allowed to exist, and/or the solvent, if used, or to a reactor in which (II-i) the phosphazenium compound represented by the chemical formula (7) and the active hydrogen compound, or (II-ii) the phosphazenium salt of the active hydrogen compound, which has been derived from the phosphazenium compound represented by the chemical formula (7) and the active hydrogen compound, and usually remaining the active hydrogen compound have been charged together with the solvent, if used, after resultant by-products are removed as needed.

According to the process of the present invention, it is also possible to use two or more alkylene oxide compounds in combination. When plural alkylene oxide compounds are simultaneously used and polymerized, a copolymer having relatively high randomness is obtained although the randomness varies depending on the difference in reactivity between the compounds. When two or more alkylene oxide compounds are polymerized successively, a block copolymer containing two or more poly(alkylene oxide) blocks is obtained. For example, when a second alkylene oxide compound is polymerized directly after completion of a polymerization reaction of a first alkylene oxide compound, a block copolymer containing two kinds of blocks is obtained. By further polymerizing again the first alkylene oxide compound after completion of the polymerization of the second alkylene oxide compound or by alternately repeating the polymerization of the first and second alkylene oxide compounds, an alternating block copolymer is obtained. When three or more alkylene oxide compounds are used in combination as described above, a more complex block copolymer is obtained. Among these copolymers, preferred is a block copolymer containing poly(propylene oxide) (also called "polyoxypropylene") and poly(ethylene oxide) (also called "polyoxyethylene") blocks, which is obtained by successively polymerizing propylene oxide and ethylene oxide as alkylene oxide compounds.

Although the reaction temperature of the polymerization reaction varies depending on the kinds and amounts of the alkylene oxide compound(s) and other components to be used, it is generally 150° C. or lower and may range preferably from 10 to 130° C., more preferably from 50 to 120° C. The pressure at the time of the reaction also varies depending on the kinds and amounts of the alkylene oxide compound(s) and other components to be used and the polymerization temperature. As the pressure at the time of the polymerization, it is generally 30 kg/cm$^2$ (absolute pressure, this will apply equally hereinafter) and may range preferably from 0.1 to 15 kg/cm$^2$, more preferably from 1 to 10 kg/cm$^2$. The reaction time varies depending on the kinds and amounts of the substances to be used, but is generally 70 hours or shorter and may range preferably from 0.1 to 30 hours, more preferably from 0.5 to 24 hours.

Upon polymerization reaction, a solvent can also be used as needed. Usable examples of the solvent include aliphatic hydrocarbons such as pentane, hexane, heptane and cyclohexane; aromatic hydrocarbons such as benzene and toluene; ethers such as diethyl ether, tetrahydrofuran, 1,3-dioxane and anisole; and aprotic polar solvents such as dimethylsulfoxide, N,N-dimethylformamide, hexamethylphosphoramide and N,N'-dimethylimidazolidinone. Any other solvents are also usable unless they inhibit the polymerization reaction in the process of the present invention. The polymerization reaction in the process of the present invention can be conducted in the presence of an inert gas such as nitrogen or argon if necessary.

The poly(alkylene oxide) obtained in accordance with the process of the present invention may be used as a raw material for a polyurethane foam or elastomer or as a surfactant either as is or after removal of a solvent when the solvent is used in the polymerization reaction. In general, however, the poly(alkylene oxide) is used after its treatment with a mineral acid such as hydrochloric acid, phosphoric acid or sulfuric acid; an organic carboxylic acid such as formic acid, acetic acid or propionic acid; an acid-form ion-exchange resin; or the like. It is also possible to conduct commonly-employed purification, for example, to wash the poly(alkylene oxide) with water, an organic solvent or a mixture thereof.

The present invention will next be described in further detail by the following examples. These examples should however be interpreted to be solely for the purpose of illustration but not limitation.

EXAMPLE 1

(Synthesis of the tetrakis[tris(dimethylamino) phosphoranilideneamino]phosphonium salt of methanol; $[(Me_2N)_3P=N]_4P^+(MeO)^-$ (Me represents a methyl group; this will hereinafter apply equally))

Figure 2:
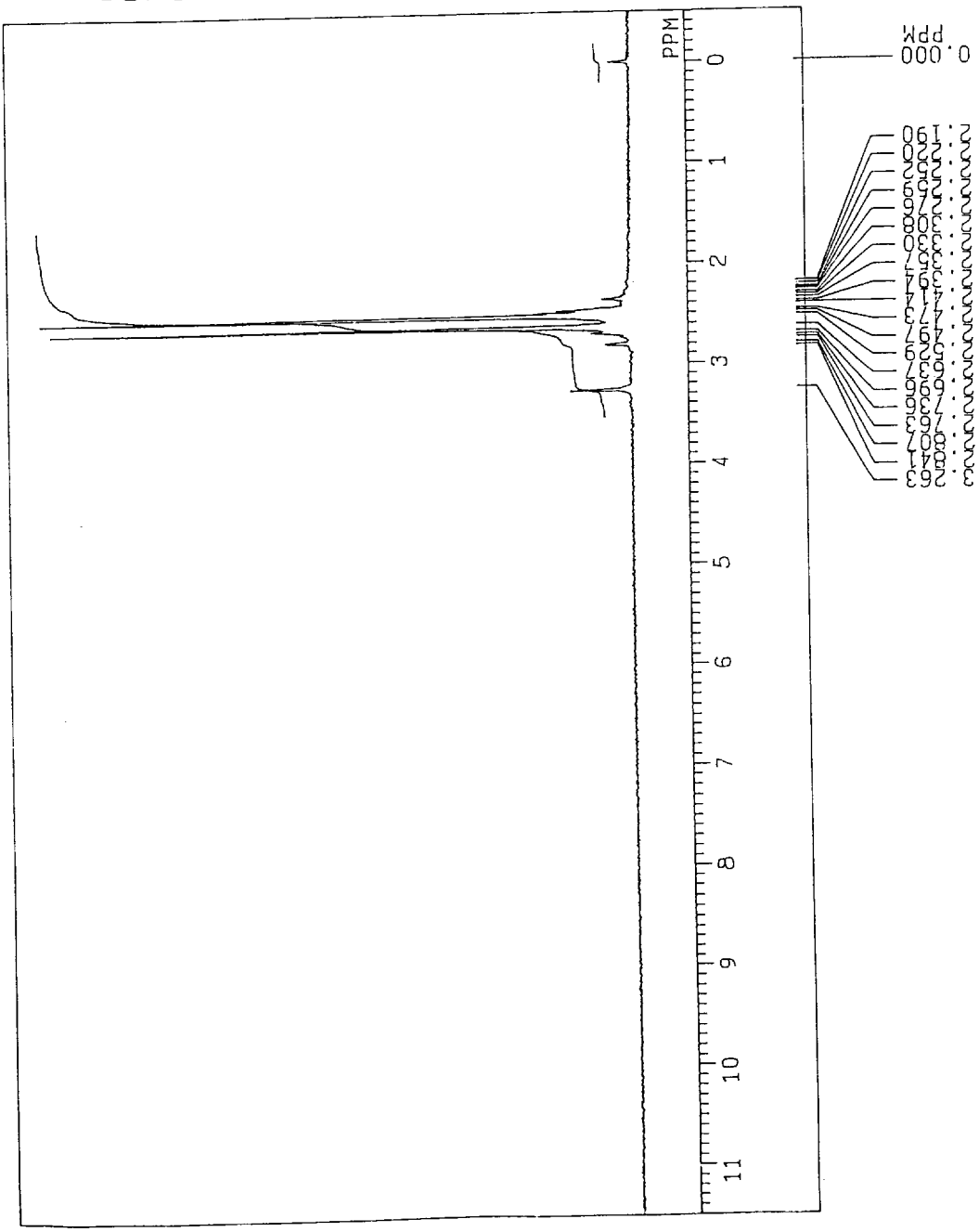
FIG. 2 is a ¹H-NMR (solvent: DMSO-d₆) spectrum of the tetrakis[tris(dimethylamino)phosphoranilideneamino] phosphonium salt of methanol.

Sodium hydride (240 mg, 10.0 mmol) was weighed in a 100-ml eggplant-type flask, to which 20 ml of DMSO (which stands for dimethyl sulfoxide; this will hereinafter apply equally) were added to form a suspension. The suspension was heated at 80° C. for 1 hour so that a homogeneous solution of a green color was obtained. Methanol (320 mg, 10.0 mmol) was added to this solution at 0° C. under a nitrogen gas atmosphere so that sodium methoxide was formed. The resultant mixture was stirred for 1 hour, followed by the addition of 7.8 g (10.0 mmol) of tetrakis[tris (dimethylamino)phosphoranilideneamino]phosphonium chloride $\{[(Me_2N)_3P=N]_4P^+Cl^-\}$ (product of Fluka Corp.) at room temperature. The thus-obtained mixture was then stirred for 2 hours and was concentrated under reduced pressure to dryness. Thirty milliliters of THF (which stands for tetrahydrofuran; this will hereinafter apply equally) were added to the residue. After the insoluble matter was filtered off, the filtrate was concentrated to dryness, whereby 7.6 g of the target phosphazenium salt of the active hydrogen compound, i.e., the tetrakis[tris(dimethylamino) phosphoranilideneamino]phosphonium salt of methanol were obtained as a colorless oily substance. Its yield was 98%. A $^{31}$P-NMR and $^1$H-NMR spectra of its DMSO-d$_6$ solution are shown in FIG. 1 and FIG. 2, respectively. Chemical shifts by the $^{31}$P-NMR, in which 85% phosphoric acid was used as an external reference, are observed at –37.4 and 3.6 ppm, which can be attributed respectively to the central phosphorus atom and to the surrounding four phosphorus atoms in the tetrakis[tris(dimethylamino) phosphoranilideneamino]phosphonium cation, $[(Me_2N)_3 P=N]_4P^+$. On the other hand, chemical shifts by the $^1$H-NMR, in which TMS (which stands for tetramethylsilane; this will hereinafter apply equally) was used as an internal reference, are observed at 2.6 and 3.2 ppm. The former chemical shift can be attributed to the methyl groups in the tetrakis[tris(dimethylamino)-phosphoranilideneamino]phosphonium cation and is observed as a doublet for their coupling with the phosphorus atom, whereas the latter can be attributed to the methyl group in the methoxy anion. Its elemental analysis data (wt. %; this will hereinafter apply equally) were: C, 38.55, H, 9.90, N, 29.51; P, 20.49; (calculated: C, 38.95; H, 9.81; N, 29.07; P, 20.09).

EXAMPLE 2

(Synthesis of dimethylaminotris[tris(dimethylamino) phosphoranilideneamino]phosphonium tetrafluoroborate; $(Me_2N)[(Me_2N)_3P=N]_3P^+BF_4^-$)

Figure 3:
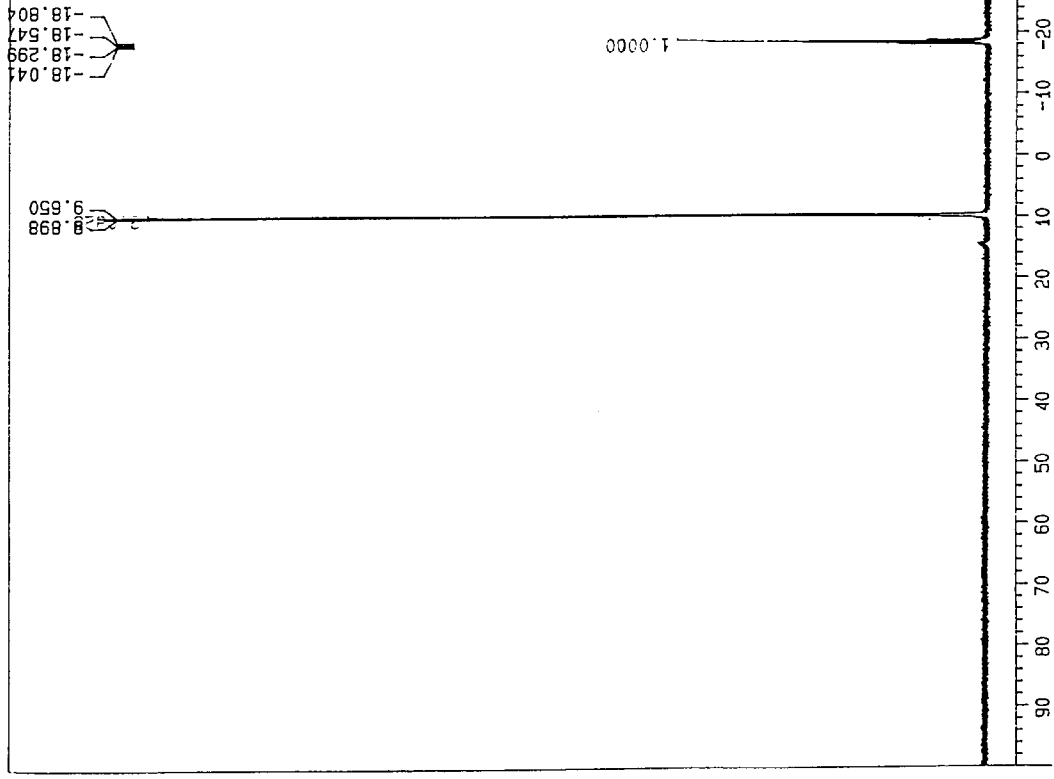
FIG. 3 is a ³¹P-NMR (solvent: CDCl₃) spectrum of dimethylaminotris[tris(dimethylamino) phosphoranilideneamino]phosphonium tetrafluoroborate.
Figure 4:
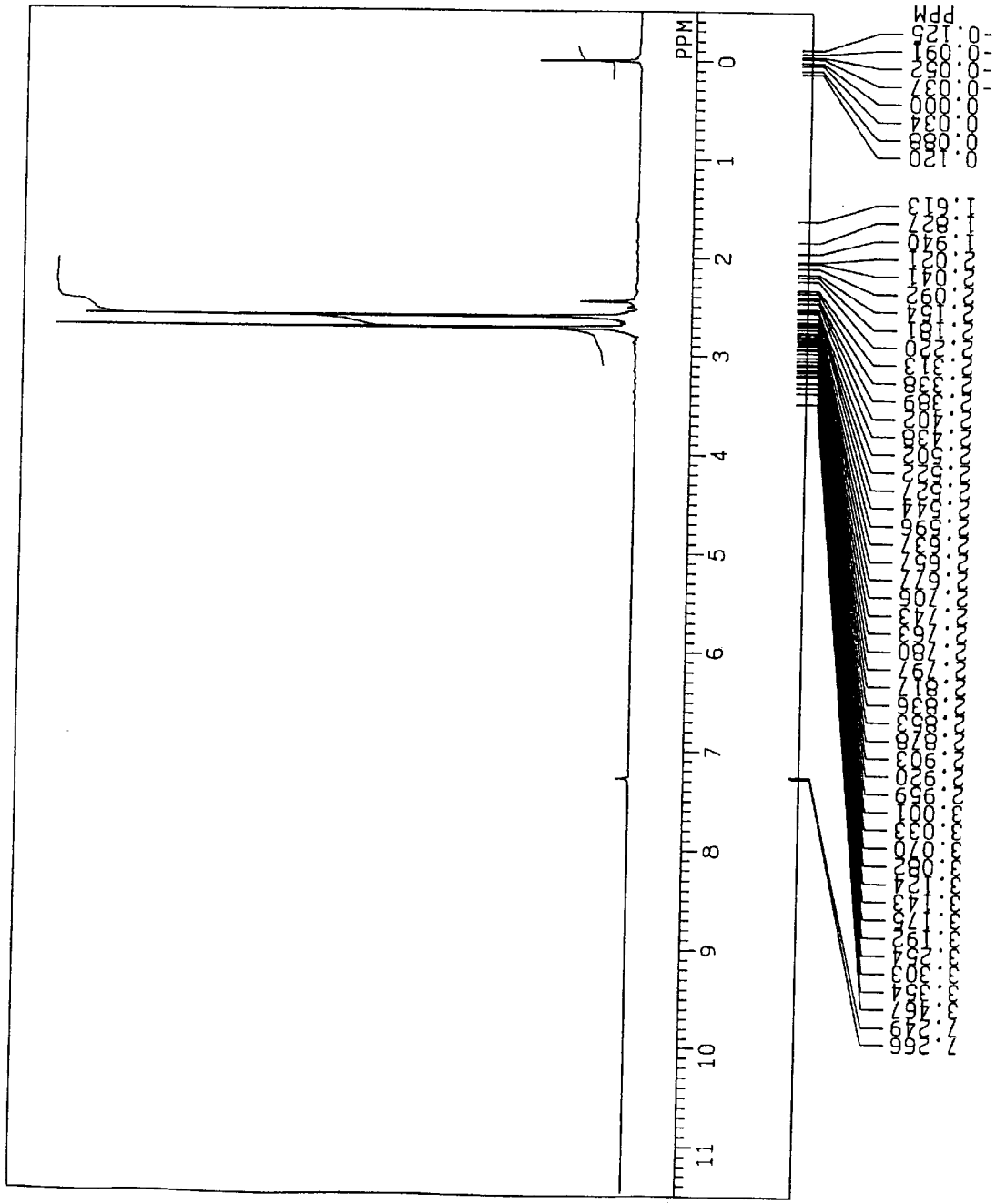
FIG. 4 is a ¹H-NMR (solvent: CDCl₃) spectrum of the dimethylaminotris[tris(dimethylamino) phosphoranilideneamino]phosphonium tetrafluoroborate.

In a 300-ml 3-necked flask fitted with a thermometer and a dropping funnel, 10.0 g (48.0 mmol) of phosphorus pentachloride were weighed, to which 50 ml of THF were added to form a suspension. The suspension was cooled to –70° C., to which a solution of 50.0 g (280.5 mmol) of tris(dimethylamino)phosphazene $\{(Me_2N)_3P=NH\}$, which had been synthesized by the process described on page 1362 of Reinhard Schwesinger, et al. Angew. Chem. Int. Ed. Engl., 32, 1361–1363 (1993), in 90 ml of THF was added dropwise over 1 hour. After the resultant mixture was stirred at the same temperature for 30 minutes, its temperature was allowed to rise back to room temperature over about 30 minutes, followed by stirring for 20 hours. The resultant insoluble matter was filtered off and the filtrate as charged in a 500-ml autoclave. After 46.0 g (1.0 mol) of dimethylamine were added at 0° C. to the filtrate, they were reacted at 80° C. for 20 hours. The reaction mixture was concentrated to dryness under reduced pressure, followed by the addition of 180 ml of a 70% aqueous solution of monoethylamine so that the residue was converted into a homogeneous solution. After an aqueous solution of 6.3 g (57.7 mmol) of sodium tetrafluoroborate in 20 ml of water was added, 400 ml of water were added and the resulting mixture was left over at room temperature for 24 hours. The resultant crystals were collected by filtration and then washed twice with 100 ml portions of a 25% aqueous solution of monoethylamine. They were recrystallized from a 5:1 mixed solvent of diethyl ether and methyl acetate, whereby 14.5 g of dimethylaminotris[tris(dimethylamino) phosphoranilideneamino]phosphonium tetrafluoroborate, a phosphazenium salt, were obtained. Its yield was 44%. Its melting point was 224–226° C. A $^{31}$P-NMR and $^1$H-NMR spectra of its CDCl$_3$ solution are shown in FIG. 3 and FIG. 4, respectively. Its elemental analysis data were: C, 34.53; H, 8.71, N, 26.10; P, 17.99; (calculated: C, 34.64; H, 8.72; N, 26.26; P, 17.87).

(Synthesis of the dimethylaminotris[tris (dimethylamino)phosphoranilideneamino] phosphonium salt of methanol; (Me$_2$N)[(Me$_2$N)$_3$P=N]$_3$P$^+$(MeO)$^-$)

Figure 5:
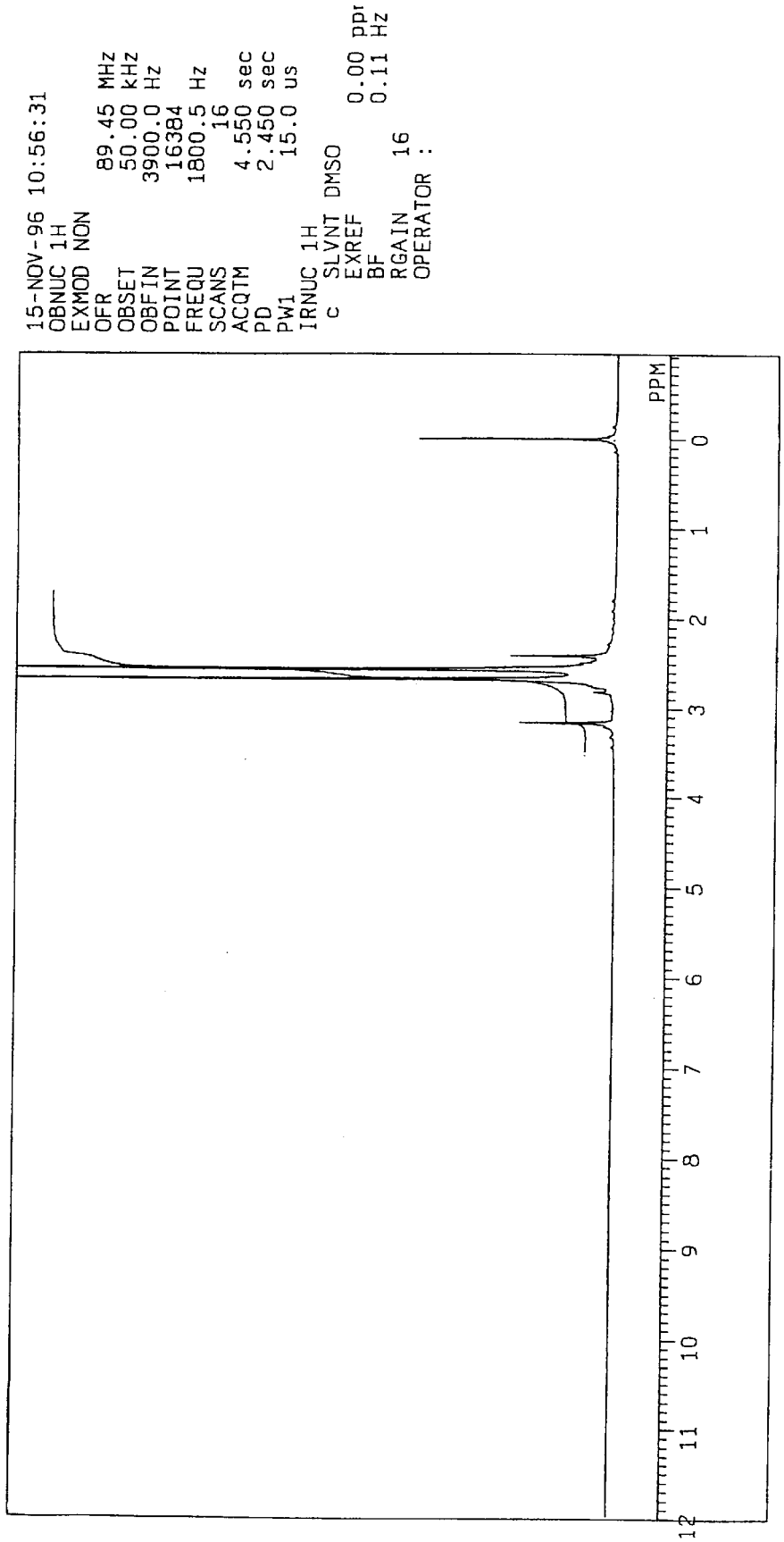
FIG. 5 is a ¹H-NMR (solvent: DMSO-d₆) spectrum of the dimethylaminotris[tris(dimethylamino) phosphoranilideneamino]phosphonium salt of methanol.

In exactly the same manner as in Example 1 except for the use of dimethylaminotris[tris(dimethylamino) phosphoranilideneamino]phosphonium tetrafluoroborate, which had been synthesized by the above-described procedures, instead of tetrakis[tris(dimethylamino) phosphoranilideneamino]phosphonium chloride, the target salt, i.e., the dimethylaminotris[tris(dimethylamino) phosphoranilideneamino]phosphonium salt of methanol was obtained. Its yield was 96%. A $^1$H-NMR spectrum of its DMSO-d$_6$ solution is shown in FIG. 5. Its elemental analysis data were: C, 39.69; H, 10.10; N, 28.11; P, 19.82; (calculated: C, 39.55; H 9.96; N, 28.55; P, 19.43).

EXAMPLE 3

(Synthesis of tetrakis[tri(pyrrolidin-1-yl) phosphoranilideneamino]phosphonium tetrafluoroborate; (Py$_3$P=N)$_4$P$^+$BF$_4$$^-$, (Py represents a pyrrolidin-1-yl group; this will hereinafter apply equally)

Figure 6:
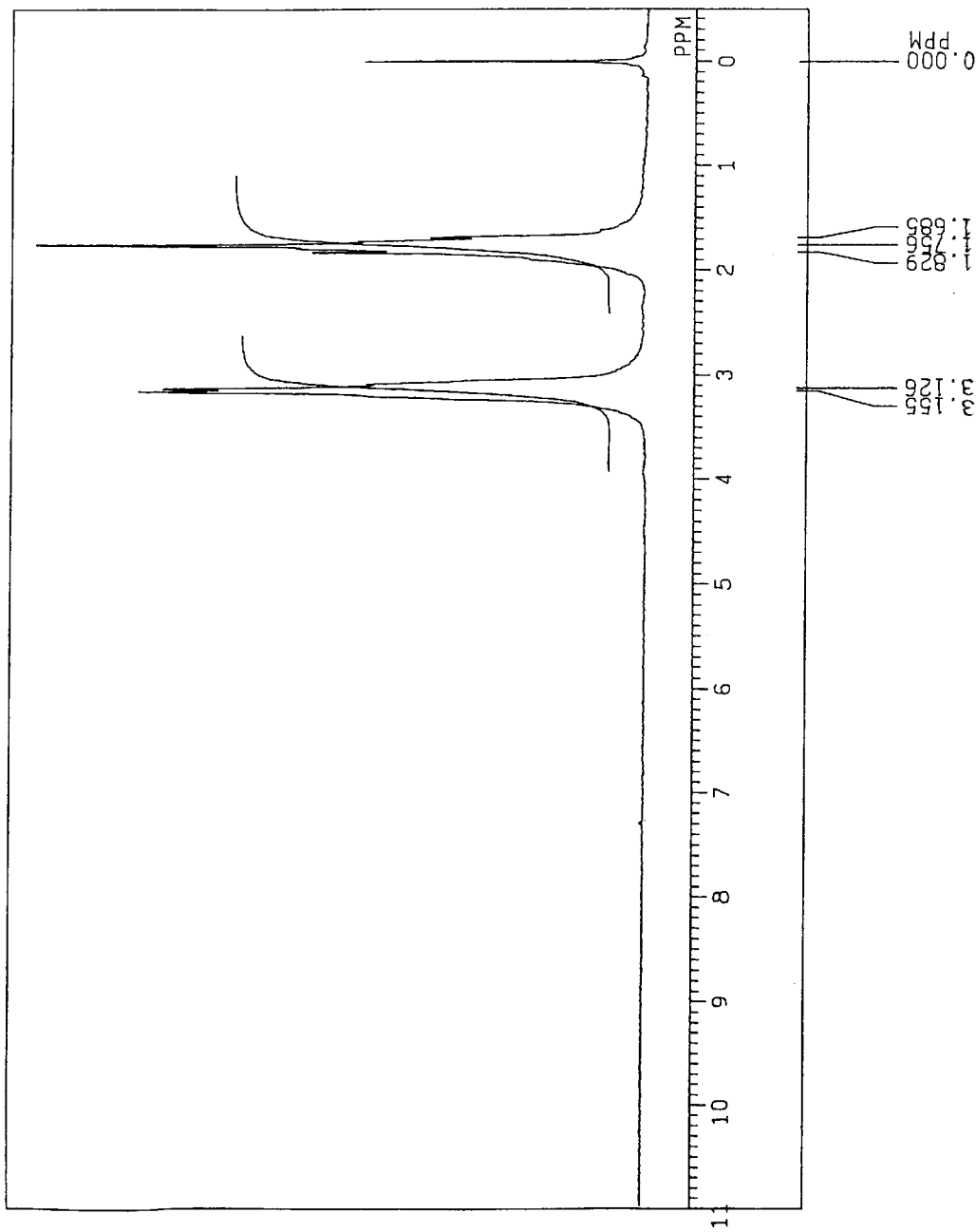
FIG. 6 is a ¹H-NMR (solvent: CDCl₃) spectrum of tetrakis[tri(pyrrolidin-1-yl)phosphoranilideneamino]- phosphonium tetrafluoroborate.

In a 200-ml 3-necked flask fitted with a thermometer and a dropping funnel, 1.6 g (7.8 mmol) of phosphorus pentachloride were weighed, to which 20 ml of THF were added to form a suspension. The suspension was cooled to –70° C., to which a solution of 20.0 g (78.0 mmol) of tri(pyrrolidin-1-yl)phosphazene {Py$_3$P=NH} in 20 ml of THF was added dropwise over 1 hour. After the resultant mixture was stirred at the same temperature for 30 minutes, its temperature was allowed to rise back to room temperature over about 30 minutes, followed by stirring for 12 hours. The THF was distilled off under reduced pressure, followed by a reaction at 110° C. for 41 hours. The reaction mixture was allowed to cool down to room temperature, to which 100 ml of a 70% aqueous solution of monoethylamine were added to form a homogeneous solution. An aqueous solution of 1.0 g (9.4 mmol) of sodium tetrafluoroborate in 5 ml of water was added to the homogeneous solution, and the resulting mixture was left over at 0° C. for 24 hours. The resultant crystals were collected by filtration. The crystals were washed twice with 10 ml portions of an ice-cooled 70% aqueous solution of monoethylamine. They were recrystallized from a 1:10 mixed solvent of methanol and ethyl acetate, whereby 5.2 g of tetrakis[tri(pyrrolidin-1-yl)phosphoranilideneamino] phosphonium tetrafluoroborate, a phosphazenium salt, were obtained. Its yield was 59%. Upon measurement of its melting point, it began to be colored from around 220° C., underwent gradual decomposition without melting, and presented a black color at 270° C. A $^1$H-NMR spectrum of its CDCl$_3$ solution is shown in FIG. 6. Its elemental analysis data were: C, 50.25; H, 8.84; N, 19.51; P, 14.01; (calculated: C, 50.61; H, 8.50; N, 19.67; P, 13.60).

(Synthesis of the tetrakis[tri(pyrrolidin-1-yl) phosphoranilideneamino]phosphonium salt of tert-butanol; (Py$_3$P=N)$_4$P$^+$(tert-C$_4$H$_9$O)$^-$)

Figure 7:
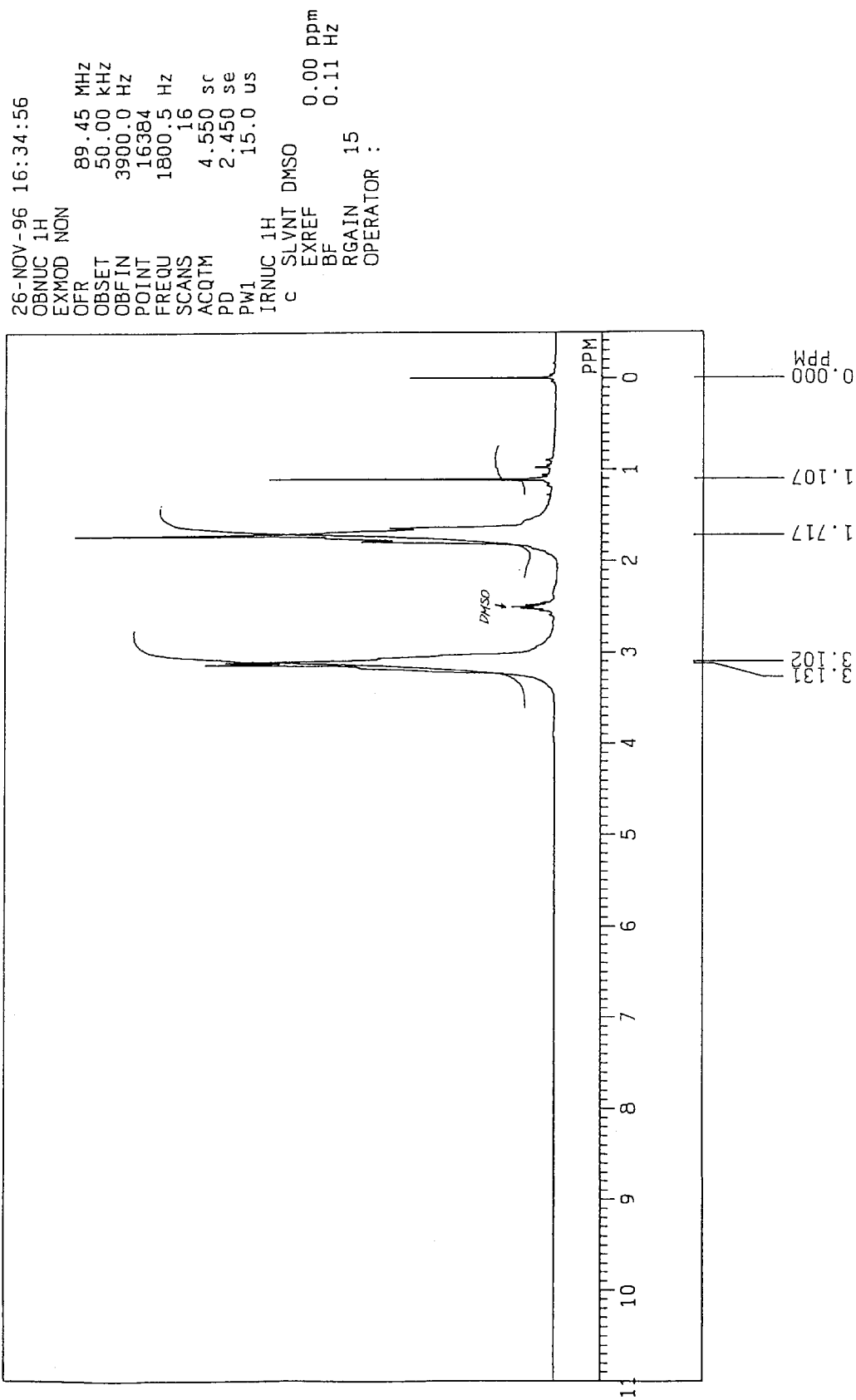
FIG. 7 is a ¹H-NMR (solvent: DMSO-d₆) spectrum of the tetrakis[tri(pyrrolidin-1-yl)phosphoranilideneamino] phosphonium salt of tert-butanol.

In exactly the same manner as in Example 1 except that tetrakis[tri(pyrrolidin-1-yl)phosphoranilideneamino] phosphonium tetrafluoroborate, which had been synthesized by the above-described procedures, was used instead of tetrakis[tris(dimethylamino)phosphoranilideneamino] phosphonium chloride, that tert-butanol was used in place of methanol and that the scale of the reaction was reduced to ⅓, the target salt, i.e., the tetrakis[tri(pyrrolidin-1-yl) phosphoranilideneamino]-phosphonium salt of tert-butanol was obtained. Its yield was 99%. A $^1$H-NMR spectrum of its DMSO-d$_6$ solution is shown in FIG. 7. Its elemental analysis data were: C, 55.19; H, 9.82; N, 20.33; P, 13.54; (calculated: C, 55.50; H, 9.40; N, 19.91; P, 13.76).

EXAMPLE 4

(Synthesis of the tetrakis[tris(dimethylamino) phosphoranilideneamino]phosphonium salt of phenol; [(Me$_2$N)$_3$P=N)$_4$P$^+$(C$_6$H$_5$O)$^-$]

Figure 8:
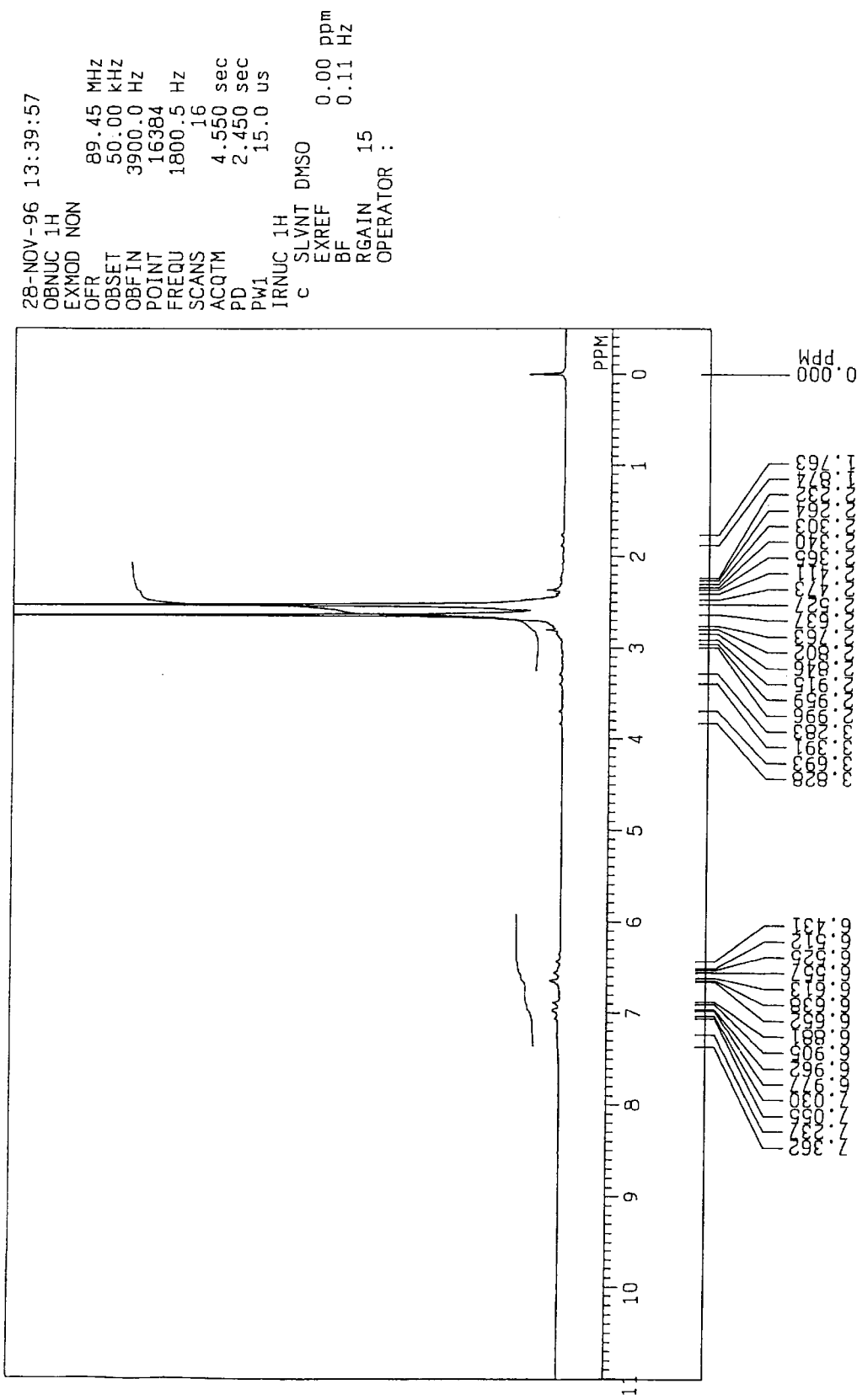
FIG. 8 is a ¹H-NMR (solvent: DMSO-d₆) spectrum of the tetrakis[tris(dimethylamino)phosphoranilideneamino] phosphonium salt of phenol.

In exactly the same manner as in Example 1 except for the use of phenol instead of methanol, the target salt, i.e., the tetrakis[tri(dimethylamino)phosphoranilideneamino] phosphonium salt of phenol was obtained. A $^1$-NMR spectrum of its DMSO-d$_6$ solution is shown in FIG. 8. Its elemental analysis data were: C, 43.15; H, 9.69; N, 27.19; P, 18.18; (calculated: C, 43.26; H, 9.32; N, 26.91; P, 18.59).

EXAMPLE 5

(Synthesis of the tetrakis[tris(dimethylamino) phosphoranilideneamino]phosphonium salt of acetic acid; [(Me$_2$N)$_3$P=N)$_4$P$^+$(CH$_3$COO)$^-$]

Figure 9:
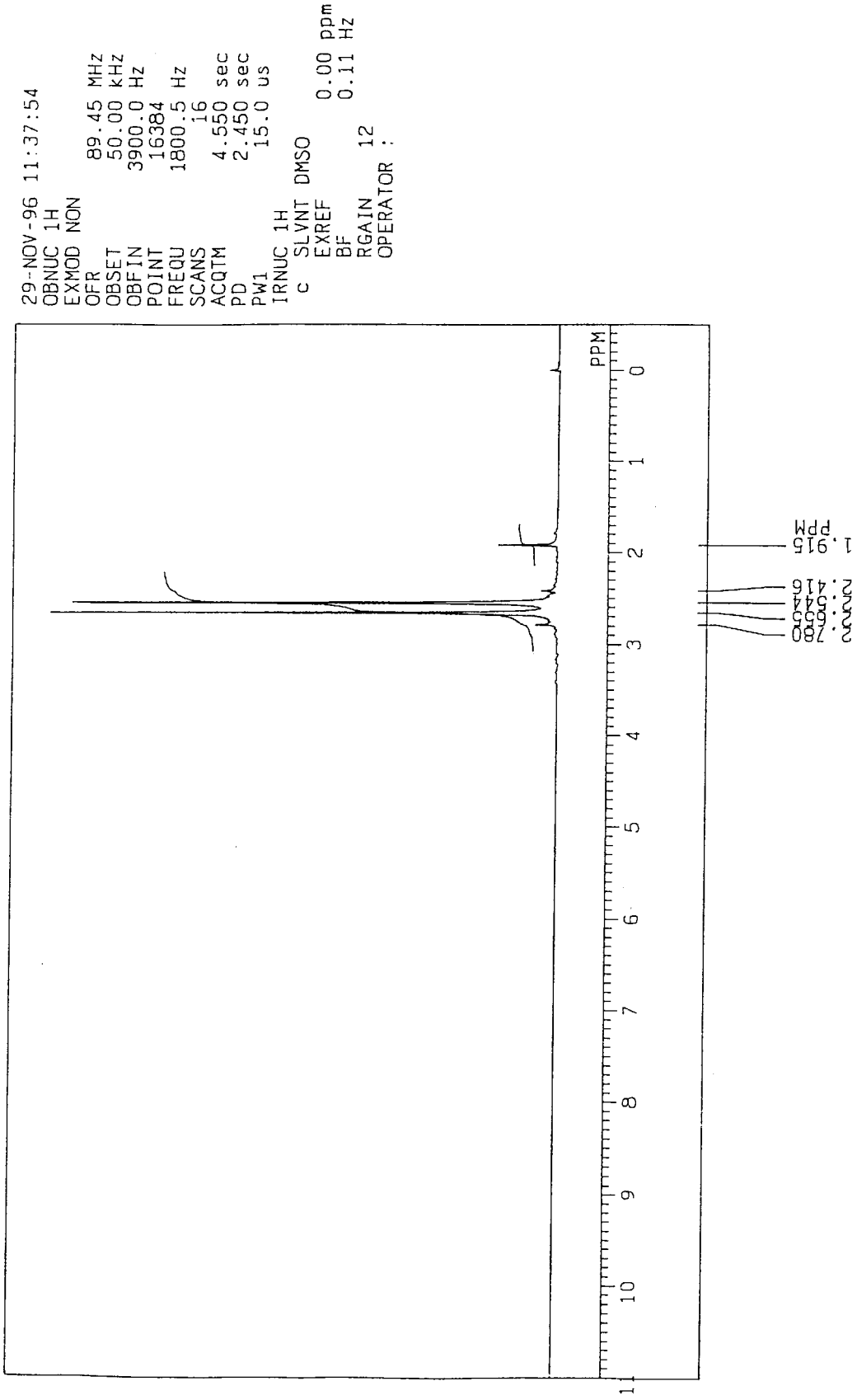
FIG. 9 is a ¹H-NMR (solvent: DMSO-d₆) spectrum of the tetrakis[tris(dimethylamino)phosphoranilideneamino] phosphonium salt of acetic acid.

Anhydrous sodium acetate (2.0 g, 24.0 mmol) was weighed in a 300-ml eggplant-type flask, followed by the addition of 100 ml of methanol to form a homogeneous solution. At room temperature, 18.9 g (24.4 mmol) of tetrakis[tris(dimethylamino)phosphoranilideneamino] phosphonium chloride was added to the homogeneous solution, followed by a reaction for 1 hour. The methanol was distilled off under reduced pressure. THF (100 ml) was added to the residue and the insoluble matter was filtered off. The filtrate was then concentrated to dryness, whereby a solid was obtained. The solid was washed with 50 ml of hexane and then dried under reduced pressure, whereby the target phosphazenium salt of the active hydrogen compound, i.e., the tetrakis[tris(dimethylamino) phosphoranilideneamino]phosphonium salt of acetic acid, was obtained. Its yield was 99%. A $^1$H-NMR spectrum of its DMSO-d$_6$ solution is shown in FIG. 9. Its elemental analysis data were: C, 38.56; H, 9.91; N, 28.19; P, 19.00; (calculated: C, 39.09; H, 9.46; N, 28.05; P, 19.39).

EXAMPLE 6

(Synthesis of the mono{tetrakis[tris(dimethylamino) phosphoranilideneamino]phosphonium} salt of N, N'-dimethylethylenediamine; [(Me$_2$N)$_3$P=N)$_4$P$^+$ (MeNHCH$_2$CH$_2$—NMe)$^-$]

Figure 10:
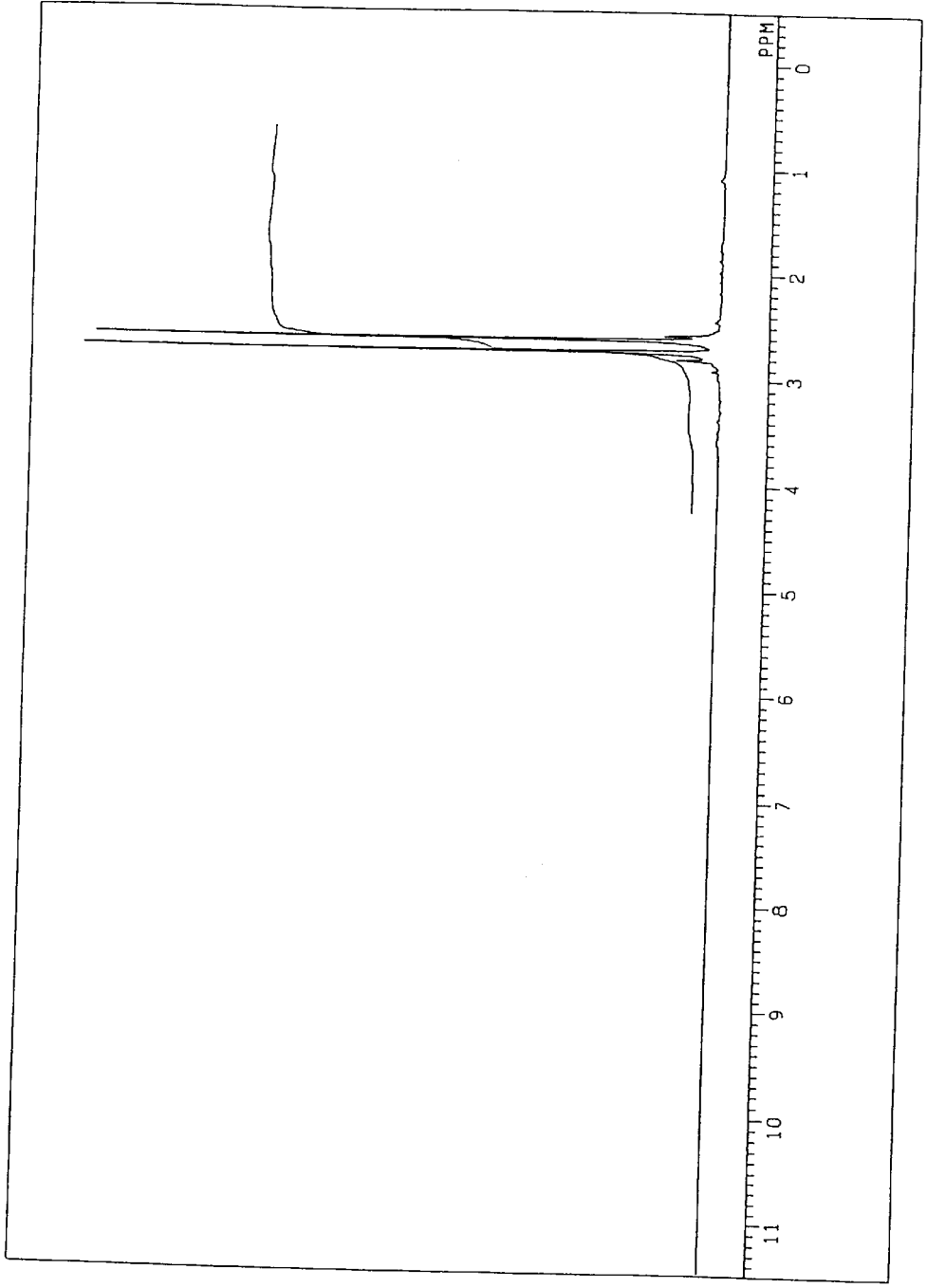
FIG. 10 is a ¹H-NMR (solvent: THF-d₈) spectrum of the mono{tetrakis[tris(dimethylamino) phosphoranilideneamino]phosphonium} salt of N,N'-dimethylethylenediamine.

N,N-Dimethylethylenediamine (0.4 g, 5.0 mmol) was weighed in a 100-ml Schlenk tube, to which 10 ml of THF were added. To the resultant mixture, 5.0 ml of a 1.0 M hexane solution of n-butyl lithium (5.0 mmol in terms of n-butyl lithium) were added at 0° C. The thus-obtained mixture was stirred at the same temperature for 10 minutes, followed by further stirring at room temperature for 30 minutes so that monolithium salt of N,N-dimethylethylenediamine was formed. The resultant mixture was cooled to –50° C., followed by the addition of a solution of tetrakis[tris(dimethylamino)phosphoranilideneamino] phosphonium chloride (3.9 g, 5.0 mmol) in 30 ml of THF. Subsequent to stirring at the temperature for 5 minutes, the temperature of the reaction mixture was allowed to rise back to room temperature over 30 minutes and was then concentrated under reduced pressure to dryness. Toluene (50 ml) was added to the residue, the insoluble matter was filtered off, and the filtrate was then concentrated to dryness, whereby the target phosphazenium salt of the active hydrogen compound, i.e., the mono{tetrakis[tris(dimethylamino) phosphoranilideneamino]phosphonium} salt of N,N'-dimethylethylenediamine was obtained as a solid. Its yield was 97%. A $^1$H-NMR spectrum of its THF-$d_8$ solution is shown in FIG. 10. Its elemental analysis data were: C, 40.79; H, 10.45; N, 30.41; P, 18.23; (calculated: C, 40.67; H, 10.12; N, 30.49; P, 18.73).

EXAMPLE 7

(Synthesis of mono{tetrakis[tris(dimethylamino) phosphoranilideneamino]phosphonium} salt of piperazine; [(Me$_2$N)$_3$P=N]$_4$P$^+$(C$_4$H$_9$N$_2$)$^-$)

Figure 11:
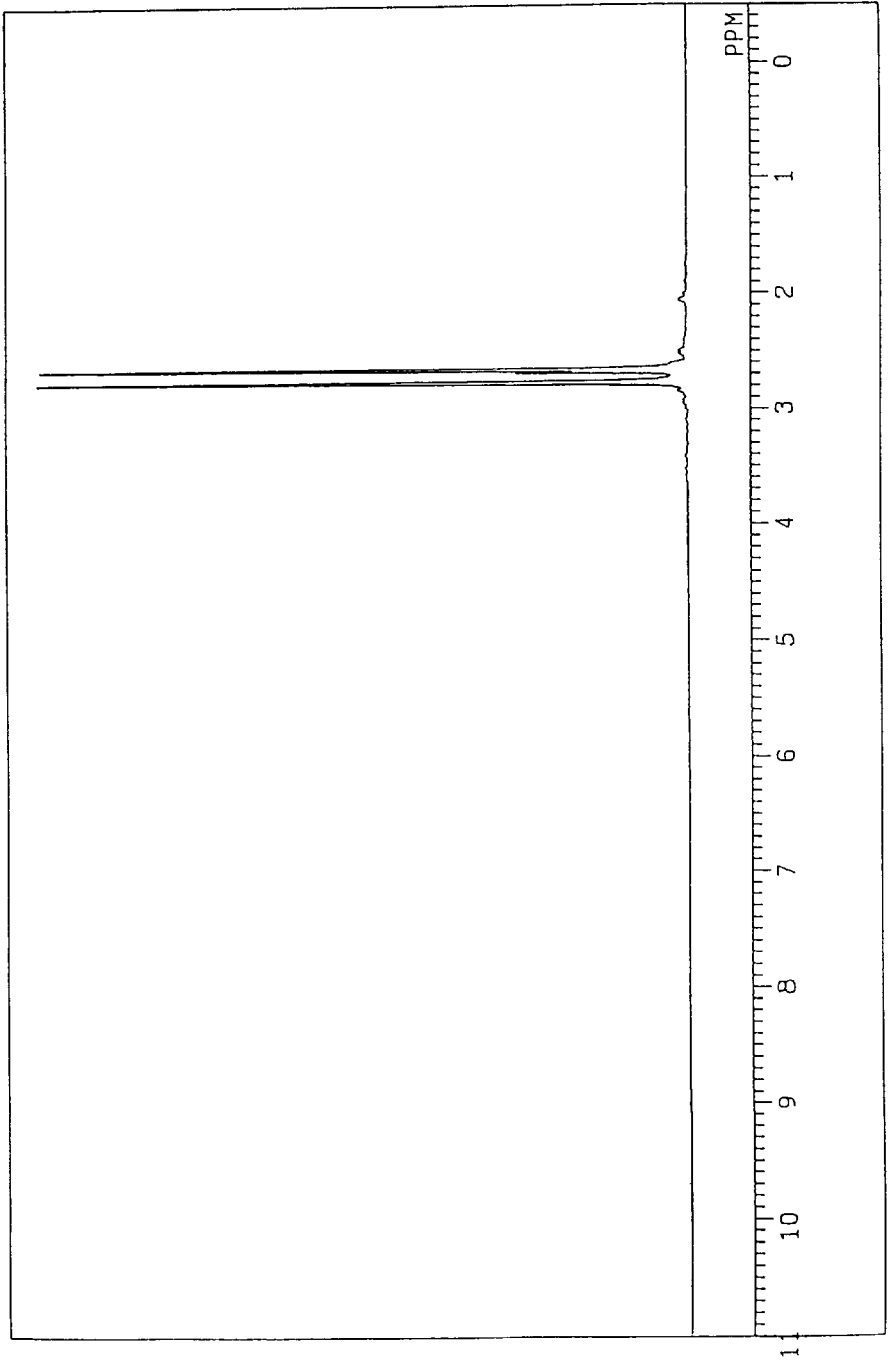
FIG. 11 is a ¹H-NMR (solvent: THF-d₈) spectrum of the mono{tetrakis[tris(dimethylamino) phosphoranilideneamino]phosphonium} salt of piperazine.
Figure 12:
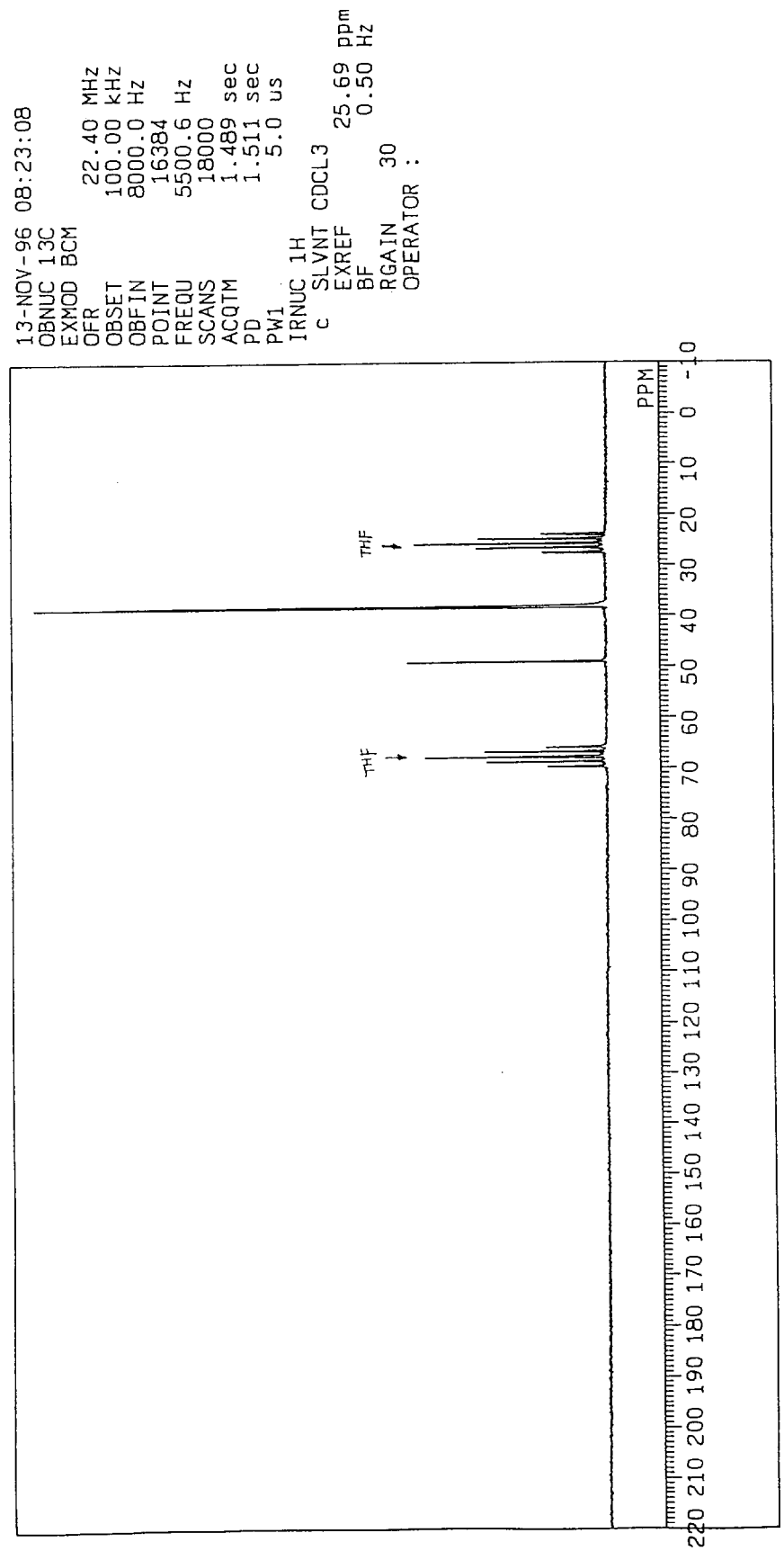
FIG. 12 is a ¹³C-NMR (solvent: THF-d₈) spectrum of the mono{tetrakis[tris(dimethylamino) phosphoranilideneamino]phosphonium} salt of piperazine.

In exactly the same manner as in Example 6 except for the use of piperazine instead of N,N'-dimethylethylenediamine, the target phosphazenium salt of the active hydrogen compound, i.e., the mono{tetrakis[tris(dimethylamino) phosphoranilideneamino]phosphonium} salt of piperazine was obtained. Its yield was 98%. A $^1$H-NMR and $^{13}$C-NMR spectra of its THF-$d_8$ solution are shown in FIG. 11 and FIG. 12, respectively. Its elemental analysis data were: C, 41.02; H, 9.56; N, 30.11; P, 18.97; (calculated: C, 40.77; H, 9.90; N, 30.56; P, 18.77).

EXAMPLE 8

(Synthesis of tetrakis[tris(dimethylamino) phosphoranilideneamino]phosphonium salt of piperidine; [(Me$_2$N)$_3$P=N]$_4$P$^+$(C$_5$H$_{10}$N)$^-$)

Figure 13:
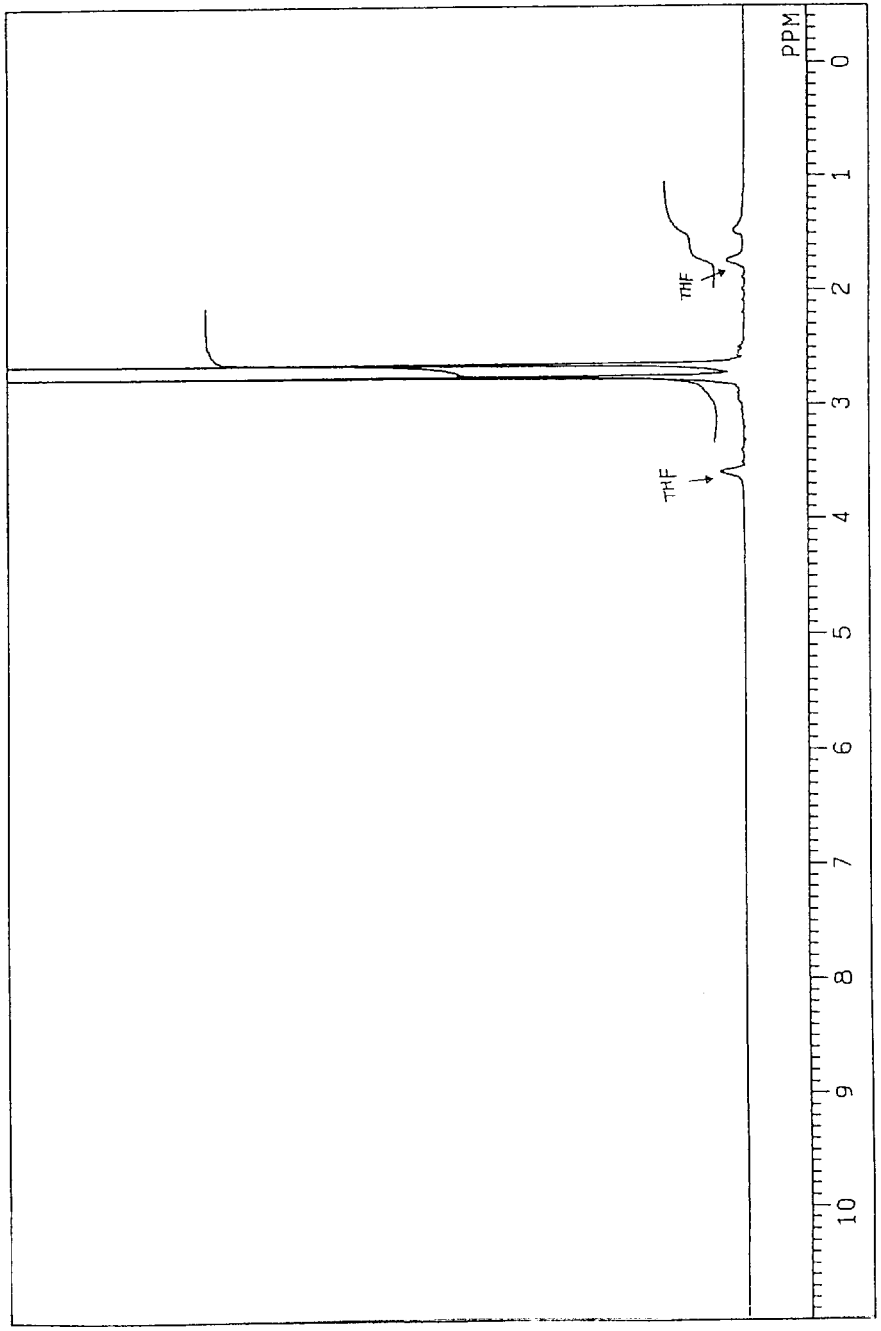
FIG. 13 is a ¹H-NMR (solvent: THF-d₈) spectrum of the tetrakis[tris(dimethylamino)phosphoranilideneamino] phosphonium salt of piperidine.

In exactly the same manner as in Example 6 except for the use of piperidine instead of N,N'-dimethylethylenediamine, the target phosphazenium salt of the active hydrogen compound, i.e., the tetrakis[tris(dimethylamino) phosphoranilideneamino]phosphonium salt of piperidine was obtained. Its yield was 97%. A $^1$H-NMR spectrum of its THF-$d_8$ solution is shown in FIG. 13. Its elemental analysis data were: C, 42.55; H, 10.01; N, 28.45; P, 19.21; (calculated: C, 42.27; H, 10.03; N, 28.90; P, 18.80).

EXAMPLE 9

Synthesis of diethylaminotris[tris(diethylamino) phosphoranilideneamino]phosphonium tetrafluoroborate; (Et$_2$N)[(Et$_2$N)$_3$P=N]$_3$P$^+$BF$_4$$^-$, (Et represents an ethyl group; this will hereinafter apply equally)

Figure 14:
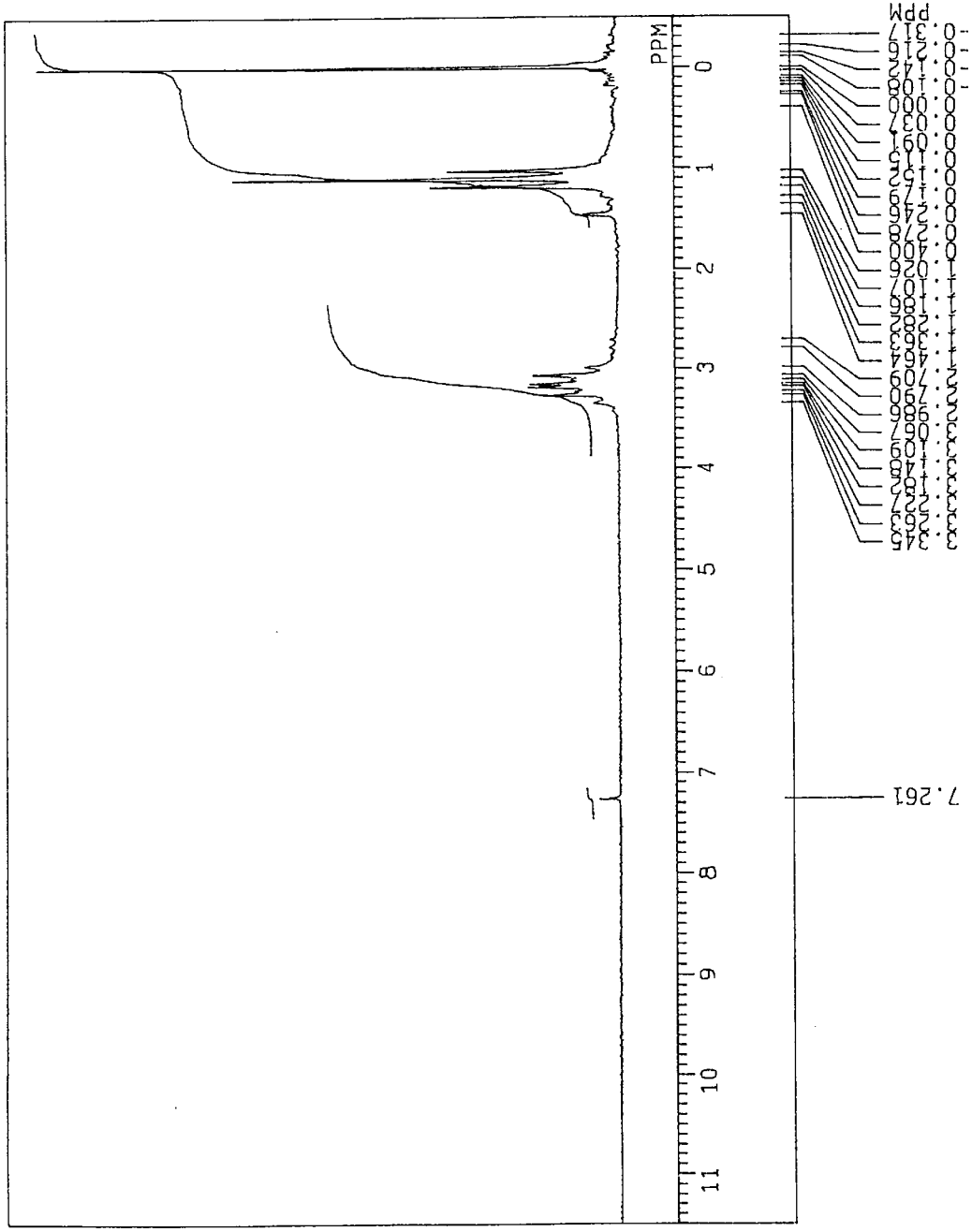
FIG. 14 is a ¹H-NMR (solvent: CDCl₃) spectrum of diethylaminotris[tris(diethylamino) phosphoranilideneamino]phosphonium tetrafluoroborate.

In a 300-ml 3-necked flask fitted with a thermometer and a dropping funnel, 3.2 g (15.1 mmol) of phosphorus pentachloride were weighed, to which 100 ml of methylene chloride were added to form a suspension. The suspension was cooled to −70° C., to which a solution of 1.1 g (15.1 mmol) of diethylamine and 1.8 g (18.2 mmol) of triethylamine in 20 ml of methylene chloride was added dropwise over 1 hour. After the resultant mixture was stirred at the same temperature for 30 minutes, 35.7 g (0.1 mol) of tris(diethylamino)-phosphazene {(Et$_2$N)$_3$P=NH} were added. The temperature of the resultant mixture was allowed to rise back to room temperature over about 30 minutes. The methylene chloride and triethylamine were distilled off under reduced pressure and 10 ml of acetonitrile were added to and mixed with the residue. The thus-obtained mixture was concentrated to dryness. After that operation was additionally repeated twice, the residue was heated and reacted at 110° C. for 24 hours. The reaction mixture was allowed to cool down to room temperature. THF (30 ml) was added and mixed with the reaction mixture. Trichloroethane (4.5 g, 33.7 mmol) was added at 0° C., followed by stirring for 2 hours. The reaction mixture was concentrated under reduced pressure to dryness and to the residue, 150 ml of a 70% aqueous solution of monoethylamine were added to form a homogeneous solution. An aqueous solution of 2.0 g (18.2 mmol) of sodium tetrafluoroborate in 5 ml of water was added to the homogeneous solution, followed by the addition of 150 ml of water. The resultant mixture was left over at room temperature for 24 hours. The resultant crystals were collected by filtration and were then washed twice with 20 ml portions of a 35% aqueous solution of monoethylamine. By drying under reduced pressure, 14.7 g of crystals were obtained. The crystals were suspended in 10 ml of THF, followed by filtration. The filtrate was concentrated to dryness, whereby 0.90 g of colorless crystals was obtained. The crystals were recrystallized from water-methanol, whereby 500 mg of diethylaminotris[tris(diethylamino) phosphoranilideneamino]phosphonium tetrafluoroborate, a phosphazenium salt, were obtained. Its yield was 4%. According to a $^1$H-NMR spectrum of its CDCl$_3$ solution, chemical shifts are observed at 0.9–1.5 (m,60H) and 2.8–3.6 (m,40H) (FIG. 14), and its elemental analysis data were: C, 58.81; H, 12.21; N, 21.85; P, 15.54; (calculated: C, 58.12; H, 12.19; N, 22.03; P, 14.99).

(Synthesis of the diethylaminotris[tris(diethylamino) phosphoranilideneamino]phosphonium salt of n-octanol; (Et$_2$N)[(Et$_2$N)$_3$P=N]$_3$P$^+$(n-C$_8$H$_{17}$O)$^-$)

Figure 15:
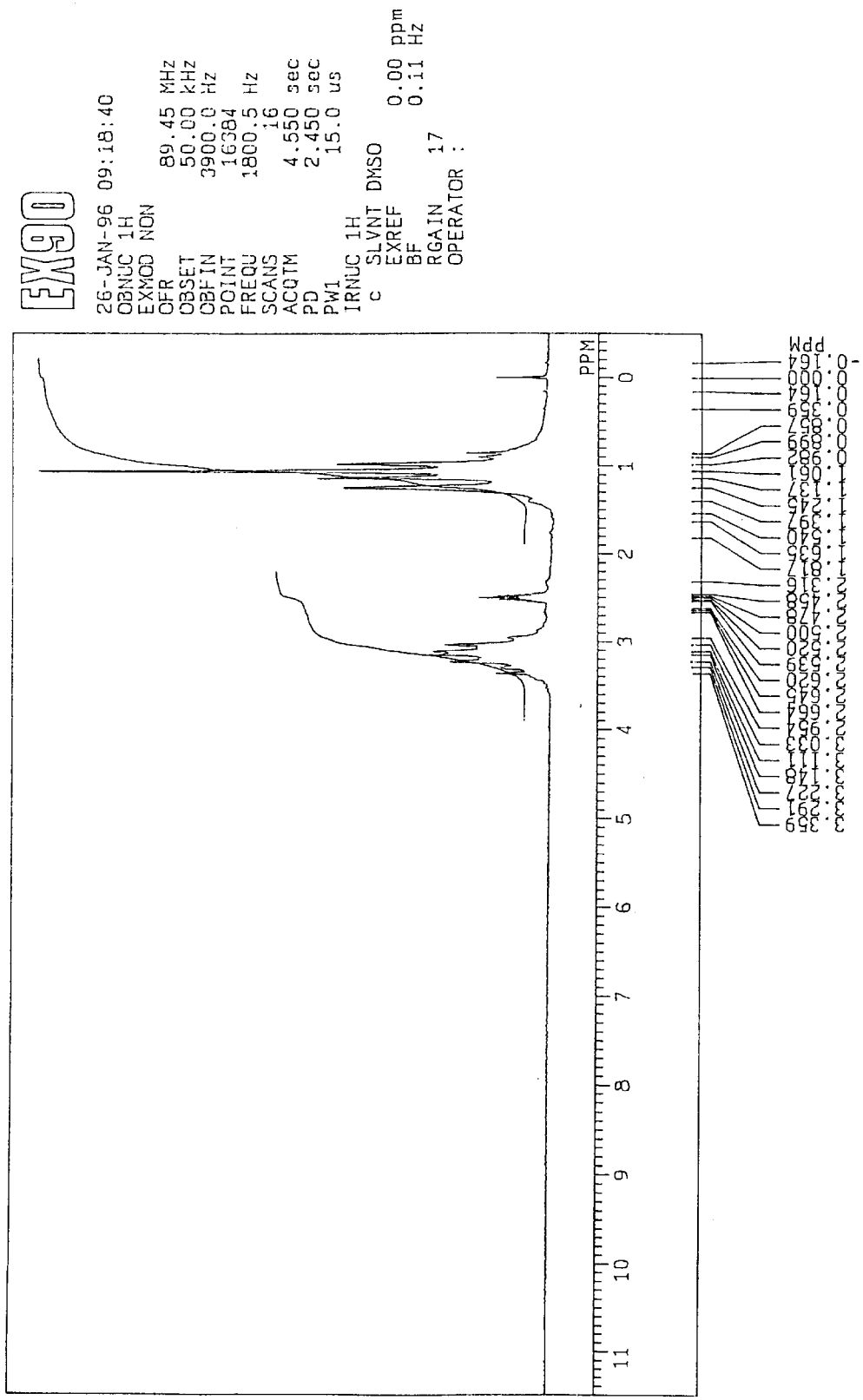
FIG. 15 is a ¹H-NMR (solvent: DMSO-d₆) spectrum of the diethylaminotris[tris(diethylamino) phosphoranilideneamino]phosphonium salt of n-octanol.

In a similar manner as in Example 1 except that diethylaminotris[tris(diethylamino) phosphoranilideneamino]phosphonium tetrafluoroborate, which had been synthesized by the above-described procedures, was used instead of tetrakis[tris(dimethylamino) phosphoranilideneamino]phosphonium chloride, that n-octanol was used in place of methanol and that the scale of the reaction was reduced to ¹⁄₁₀, the target phosphazenium salt of the active hydrogen compound, i.e., the diethylaminotris[tris(diethylamino) phosphoranilideneamino]phosphonium salt of n-octanol was obtained. Its yield was 92%. A $^1$H-NMR spectrum of its DMSO-$d_6$ solution is shown in FIG. 15. Its elemental analysis data were: C, 56.81; H, 11.98; N, 17.12; P, 12.61; (calculated: C, 56.71; H, 11.60; N, 17.91; P, 12.19).

EXAMPLE 10

(Synthesis of bis(diethylamino)bis[tris (diethylamino)phosphoranilideneamino] phosphonium tetrafluoroborate; (Et$_2$N)$_2$[(Et$_2$N)$_3$P=N]$_2$P$^+$BF$_4$$^-$)

Figure 16:
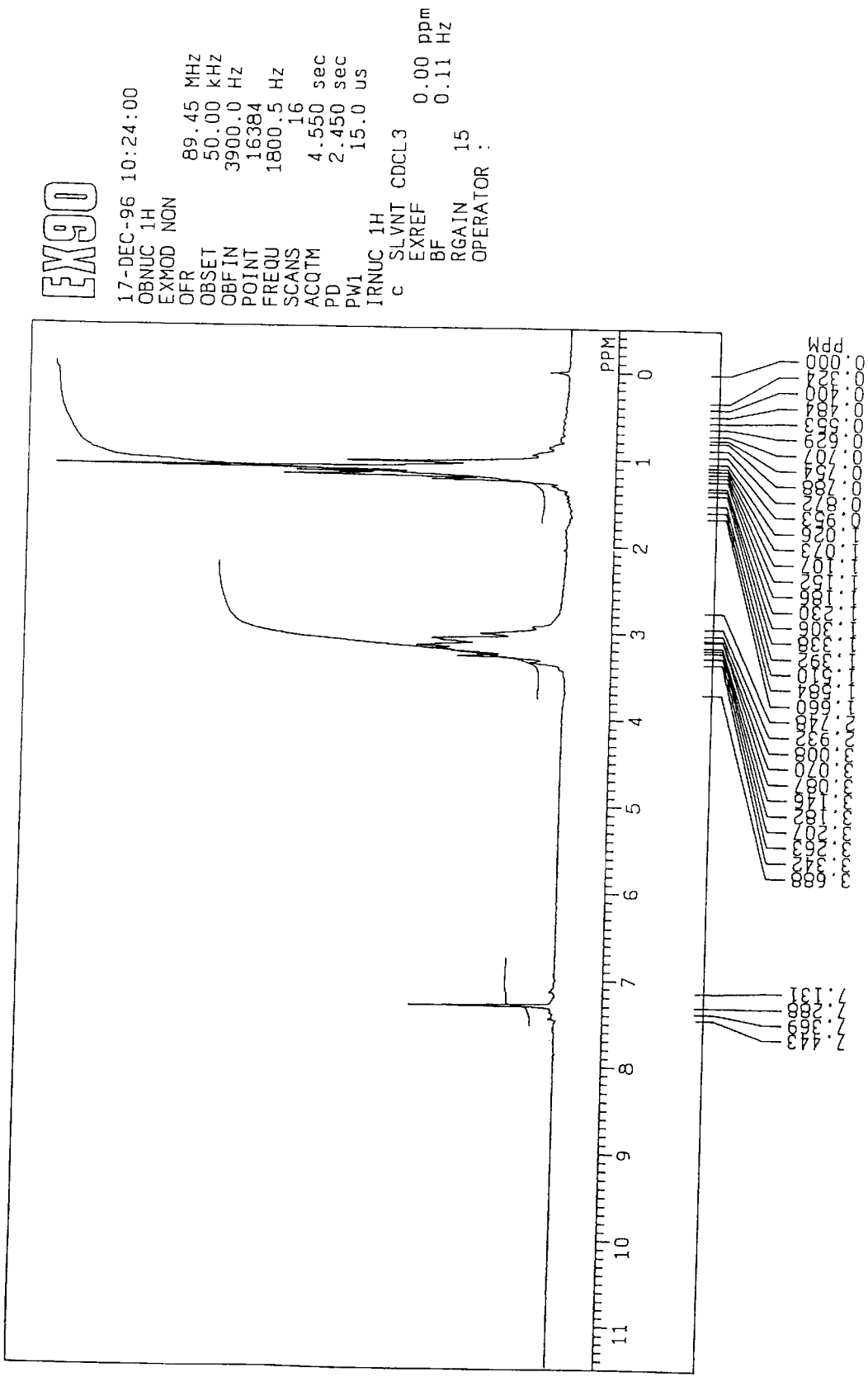
FIG. 16 is a ¹H-NMR (solvent: CDCl₃) spectrum of bis(diethylamino)bis[tris(diethylamino) phosphoranilideneamino]phosphonium tetrafluoroborate.

In a 300-ml 3-necked flask fitted with a thermometer and a dropping funnel, 3.4 g (16.6 mmol) of phosphorus pentachloride were weighed, to which 100 ml of methylene chloride were added to form a suspension. The suspension was cooled to −70° C., to which a solution of 2.4 g (33.1 mmol) of diethylamine and 4.0 g (40 mmol) of triethylamine in 20 ml of methylene chloride was added dropwise over 1 hour. After the resultant mixture was stirred at the same temperature for 30 minutes, 34.8 g (0.1 mol) of tris (diethylamino)-phosphazene were added. The temperature of the resultant mixture was allowed to rise back to room temperature over about 30 minutes. The methylene chloride and triethylamine were distilled off under reduced pressure and 10 ml of acetonitrile were added to and mixed with the residue. The thus-obtained mixture was concentrated to dryness. After that operation was additionally repeated twice, the residue was heated and reacted at 110° C. for 24 hours. The reaction mixture was allowed to cool down to room temperature. THF (30 ml) was added and mixed with the reaction mixture. Trichloroethane (4.5 g, 33.7 mmol) was added at 0° C., followed by stirring for 2 hours. The reaction mixture was concentrated under reduced pressure and to the residue, 150 ml of a 70% aqueous solution of monoethylamine were added to form a homogeneous solution. An aqueous solution of 2.2 g (20 mmol) of sodium tetrafluoroborate in 5 ml of water was added to the homogeneous solution, followed by the addition of 150 ml of water. The resultant mixture was left over at room temperature for 24 hours. The resultant crystals were collected by filtration and were then washed twice with 20 ml portions of a 35% aqueous solution of monoethylamine. By drying under reduced pressure, 12.5 g of crystals were obtained. The crystals were suspended in 10 ml of THF, followed by filtration. The filtrate was concentrated to dryness, whereby 1.2 g of colorless crystals were obtained. The crystals were recrystallized from water-methanol, whereby 650 mg of bis(diethylamino)bis[tris(diethylamino) phosphoranilideneamino]phosphonium tetrafluoroborate, a phosphazenium salt, were obtained. Its yield was 5%. According to a $^1$H-NMR spectrum of its CDCl$_3$ solution, chemical shifts are observed at 0.9–1.5 (m,48H) and 2.8–3.6 (m,32H) (FIG. 16), and its elemental analysis data were: C, 48.61; H, 11.02; N, 17.65; P, 11.53; (calculated: C, 48.98; H, 10.28; N, 17.85; P, 11.84).

(Synthesis of the mono{bis(diethylamino)bis[tris (diethylamino)phosphoranilideneamino] phosphonium} salt of propylene glycol; (Et$_2$N)$_2$ [(Et$_2$N)$_3$P=N]$_2$P$^+$-[HOCH$_2$CH(CH$_3$)O]$^-$)

Figure 17:
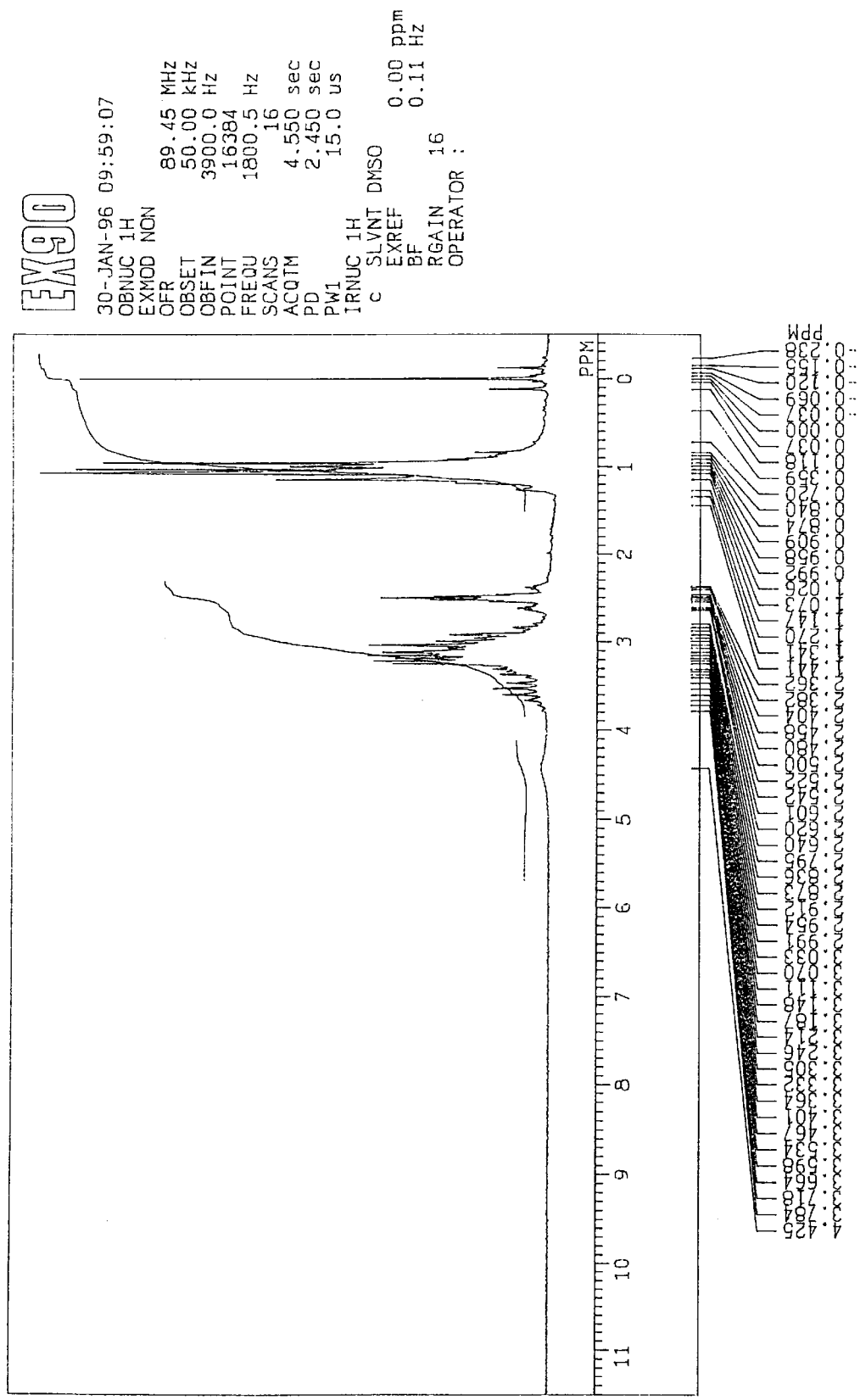
FIG. 17 is a ¹H-NMR (solvent: DMSO-d₆) spectrum of the mono{bis(diethylamino)bis[tris(diethylamino) phosphoranilideneamino]phosphonium} salt of propylene glycol.

In a similar manner as in Example 1 except that bis (diethylamino)bis[tris(diethylamino) phosphoranilideneamino]phosphonium tetrafluoroborate, which had been synthesized by the above-described procedures, was used instead of tetrakis[tris(dimethylamino) phosphoranilideneamino]phosphonium chloride, that propylene glycol was used in place of methanol and that the scale of the reaction was reduced to $^1/_{10}$, the target phosphazenium salt of the active hydrogen compound, i.e., the mono{bis (diethylamino)bis[tris(diethylamino) phosphoranilideneamino]phosphonium} salt of propylene glycol was obtained. Its yield was 87%. Chemical shifts by $^1$H-NMR of its DMSO-d$_6$ solution are shown in FIG. 17. Its elemental analysis data were: C, 54.78; H, 11.01; N, 17.59; P, 12.51; (calculated: C, 54.38; H, 11.34; N, 18.12; P, 12.02).

EXAMPLE 11

(Synthesis of the tris(dimethylamino)[tris (dimethylamino)phosphoranilideneamino] phosphonium salt of methanol; (Me$_2$N)$_3$[(Me$_2$) $_3$P=N]P$^+$(MeO)$^-$)

Figure 18:
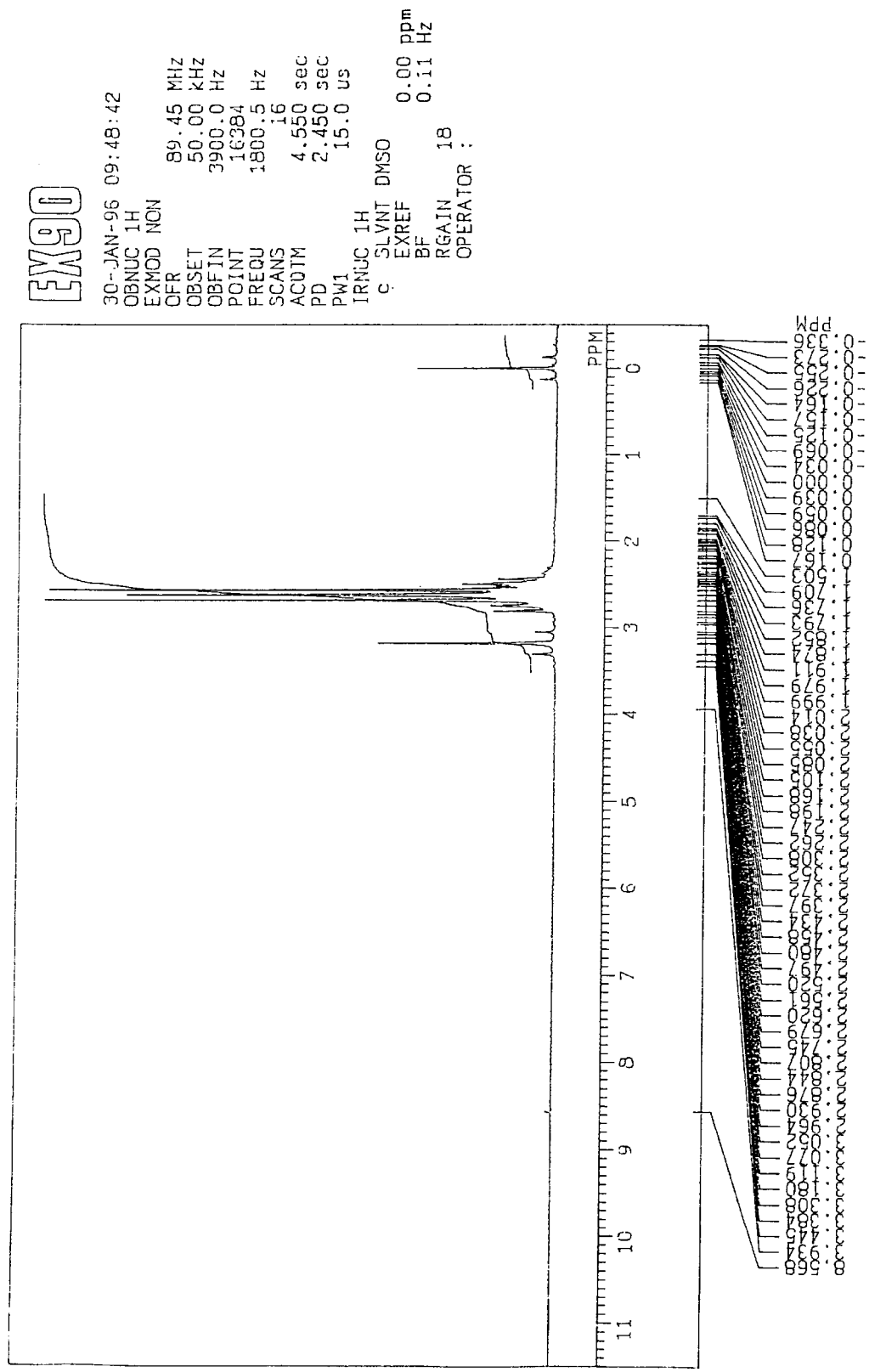
FIG. 18 is a ¹H-NMR (solvent: DMSO-d₆) spectrum of the tris(dimethylamino)[tris(dimethylamino) phosphoranilideneamino]phosphonium salt of methanol.

In a similar manner as in Example 1 except for the use of tris(dimethylamino)[tris(dimethylamino) phosphoranilideneamino]phosphonium tetrafluoroborate, {(Me$_2$N)$_3$[(Me$_2$)$_3$P=N]P$^+$BF$_4^-$—which had been synthesized by the process described in Reinhard Schwesinger, et al. Angew. Chem. Int. Ed. Engl., 31, 850 (1992)—instead of tetrakis[tris(dimethylamino)phosphoranilideneamino] phosphonium chloride, the target phosphazenium salt of the active hydrogen compound, i.e., the tris(dimethylamino)[tris (dimethylamino)phosphoranilideneamino]phosphonium salt of methanol was obtained as colorless crystals in an amount of 3.3 g. Its yield was 89%. Chemical shifts by $^1$H-NMR of its DMSO-d$_6$ solution were observed at 2.5–2.8 (m,36H) and 3.18 (s,3H) (FIG. 18). Its elemental analysis data were: C, 42.51; H, 10.21; N, 25.80; P, 16.12; (calculated: C, 42.03; H, 10.58; N, 26.40; P, 16.68).

EXAMPLES 12–17

(Synthesis of the tris(dimethylamino)[tris (dimethylamino)phosphoranilideneamino] phosphonium salts of various active hydrogen compounds)

The procedures of Example 1 were followed likewise except that tris(dimethylamino)[tris(dimethylamino) phosphoranilideneamino]phosphonium tetrafluoroborate was used instead of tetrakis[tris(dimethylamino) phosphoranilideneamino]phosphonium chloride and that various active hydrogen compounds shown in Table 1 were employed in lieu of methanol. In Example 16, however, sodium hydride and tris(dimethylamino)[tris (dimethylamino)phosphoranilideneamino]phosphonium tetraborate were both used twice as much as their corresponding amounts in Example 1. The results are presented in Table 1.

TABLE 1

Figure 19:
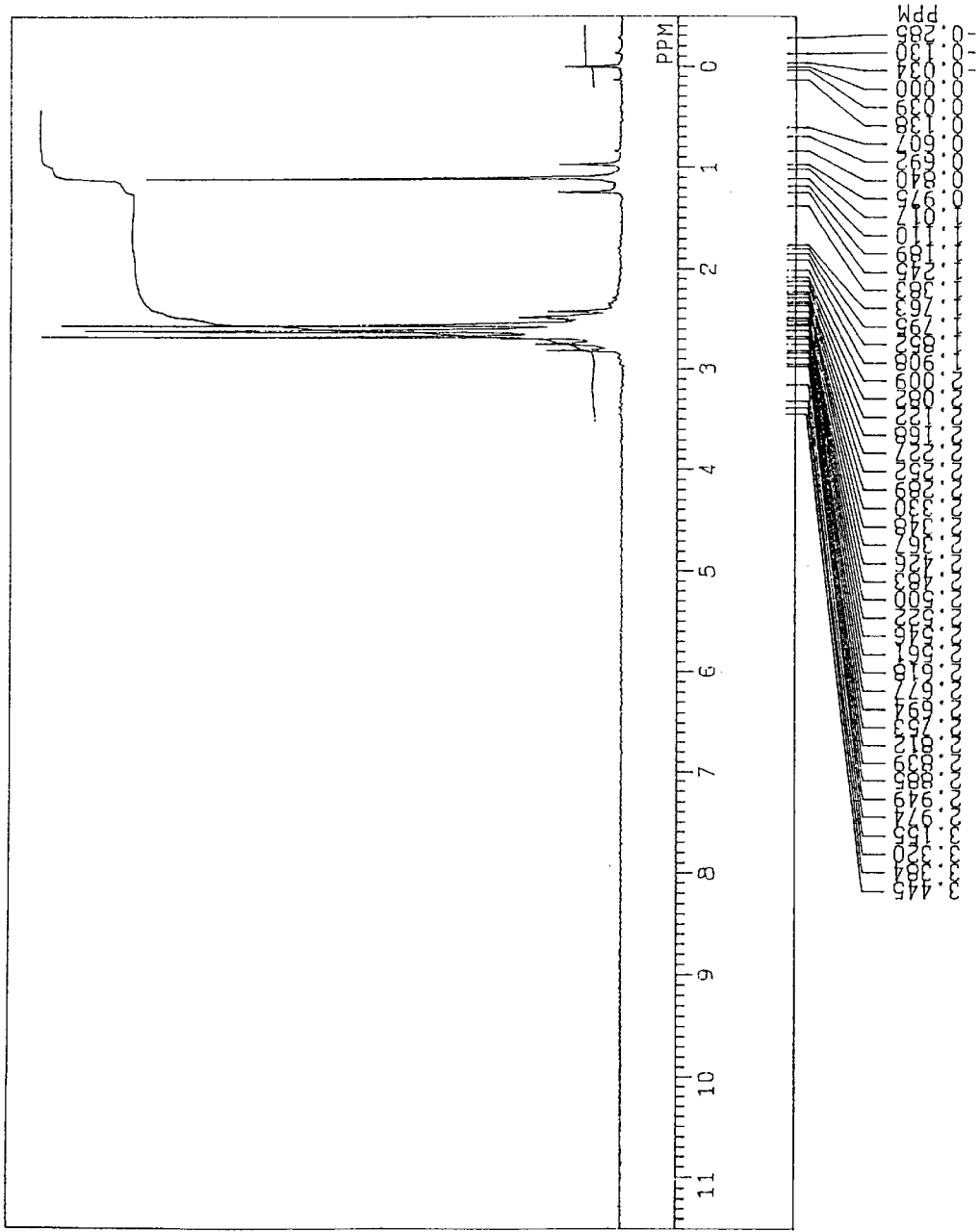
FIG. 19 is a ¹H-NMR (solvent: DMSO-d₆) spectrum of the tris(dimethylamino)[tris(dimethylamino) phosphoranilideneamino]phosphonium salt of tert-butanol.
Figure 20:
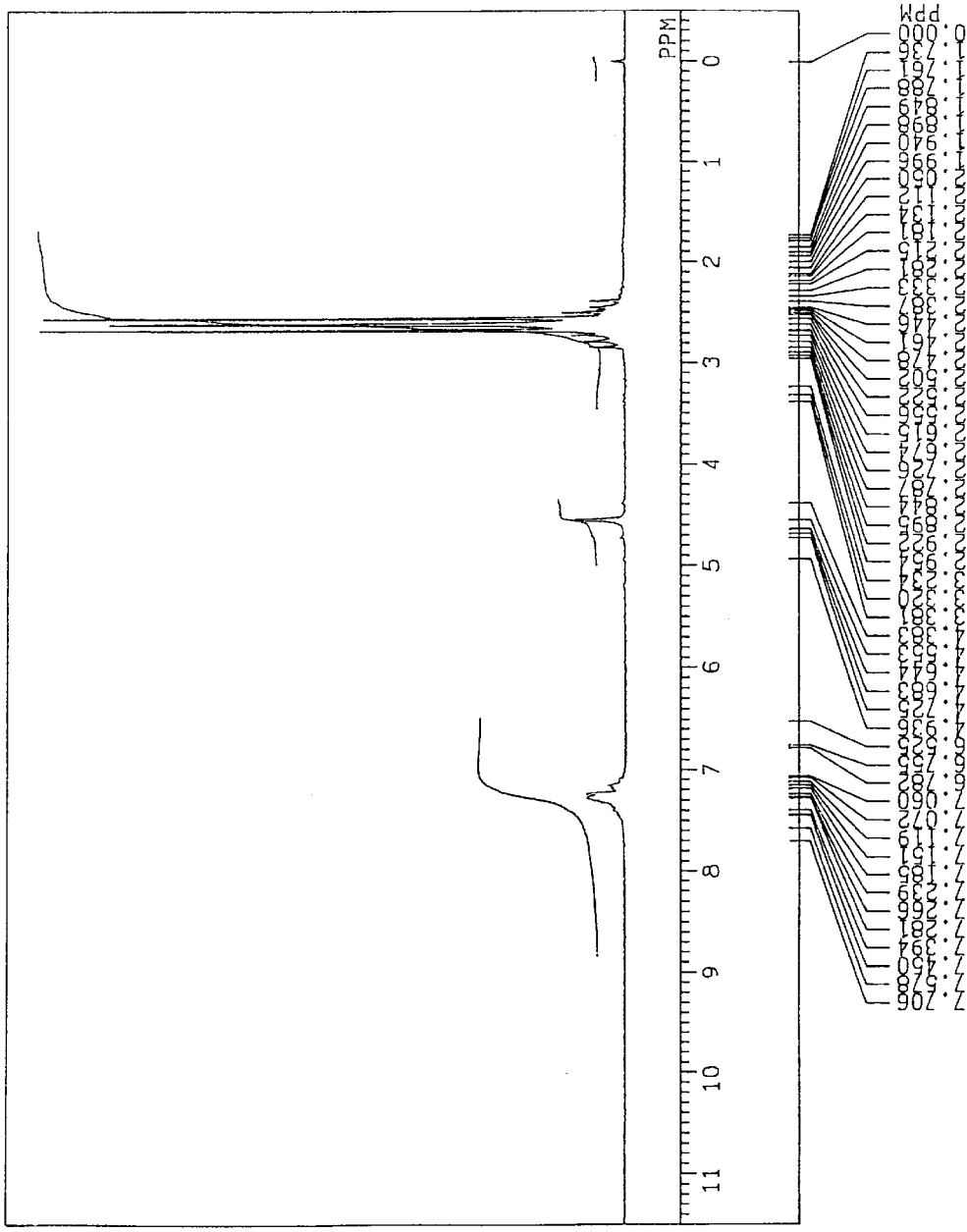
FIG. 20 is a ¹H-NMR (solvent: DMSO-d₆) spectrum of the tris(dimethylamino)[tris(dimethylamino) phosphoranilideneamino]phosphonium salt of benzyl alcohol.
Figure 21:
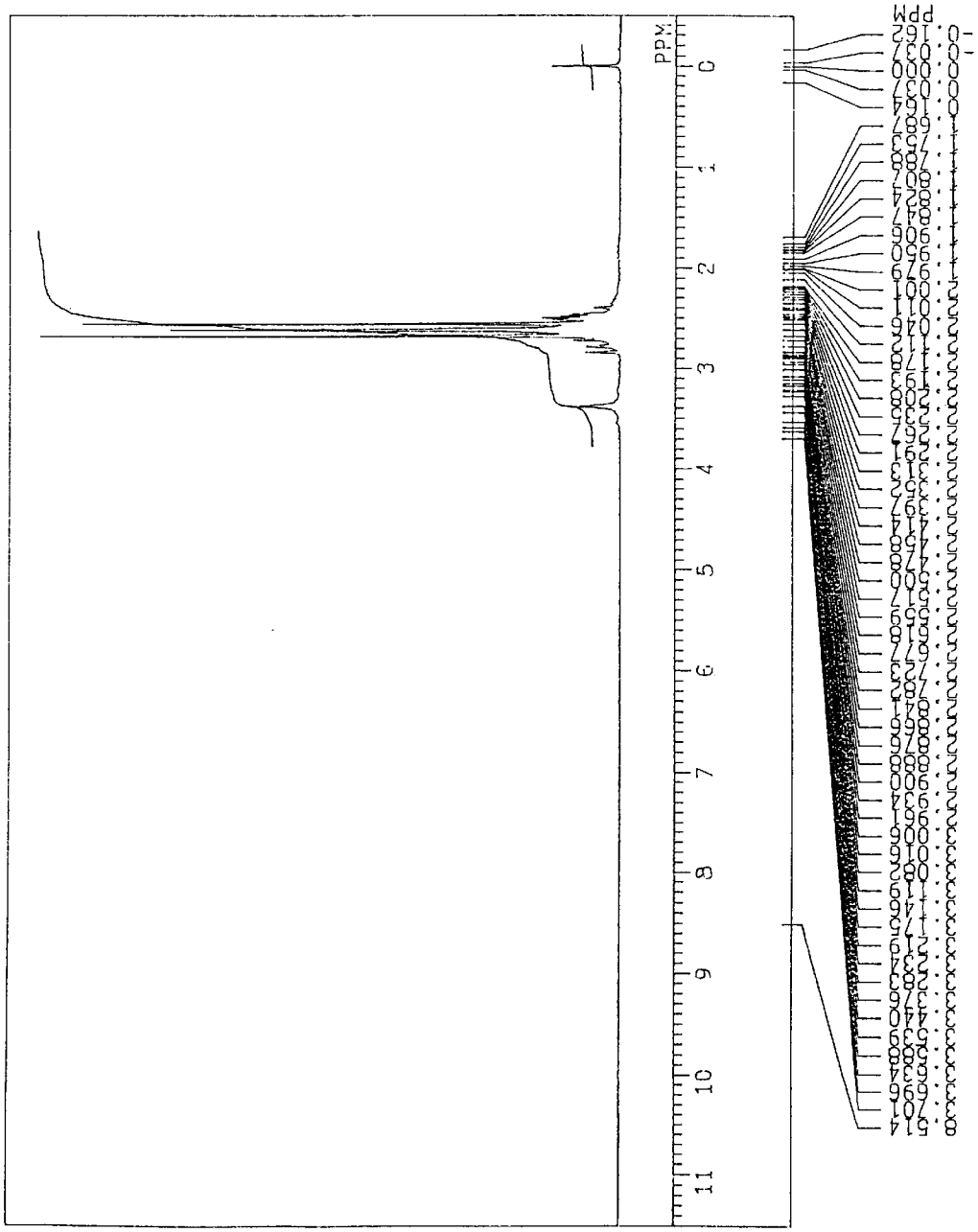
FIG. 21 is a ¹H-NMR (solvent: DMSO-d₆) spectrum of the mono{tris(dimethylamino)[tris(dimethylamino) phosphoranilideneamino]phosphonium} salt of ethylene glycol.
Figure 22:
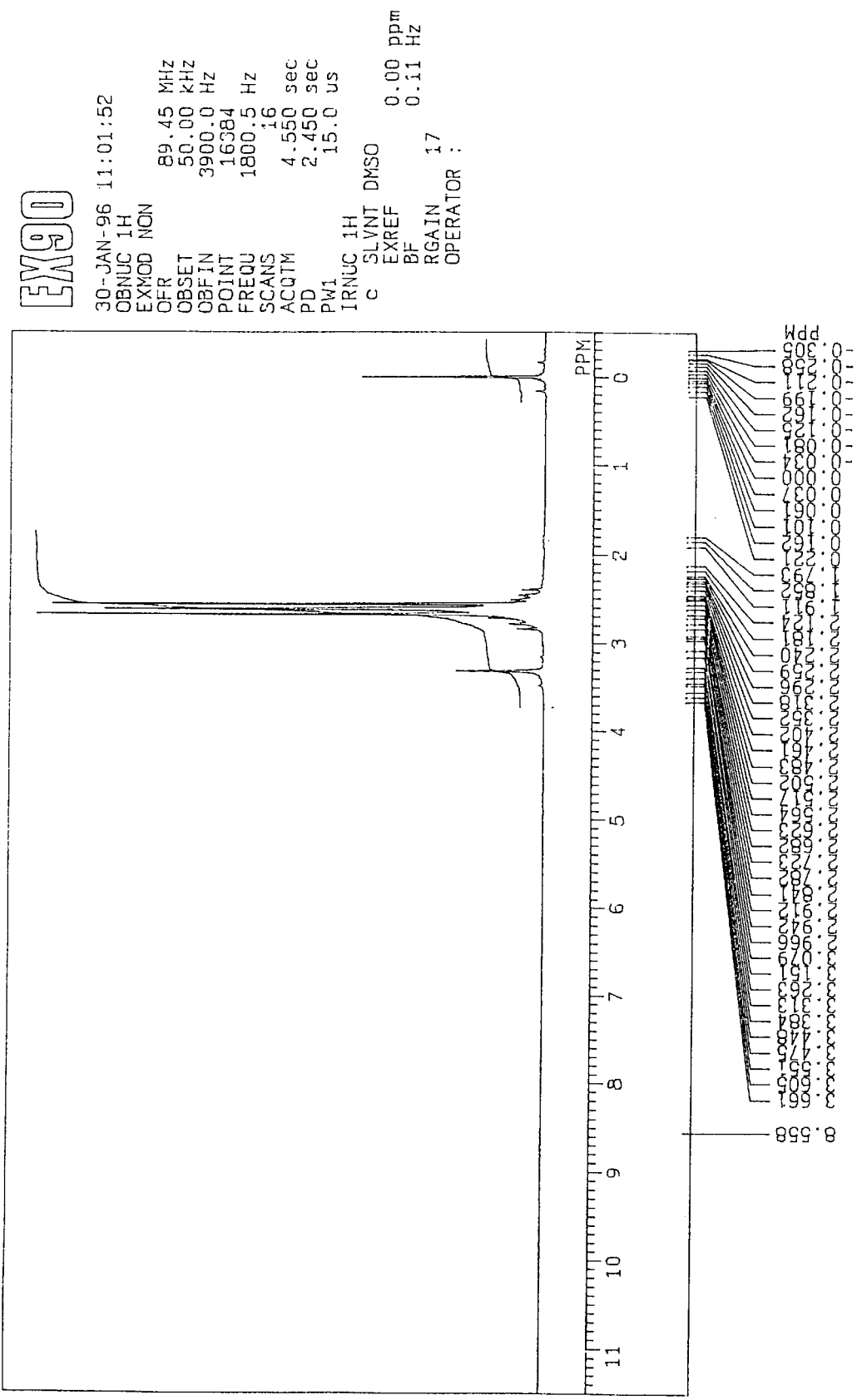
FIG. 22 is a ¹H-NMR (solvent: DMSO-d₆) spectrum of the mono{tris(dimethylamino)[tris(dimethylamino) phosphoranilideneamino]phosphonium} salt of glycerol.
Figure 23:
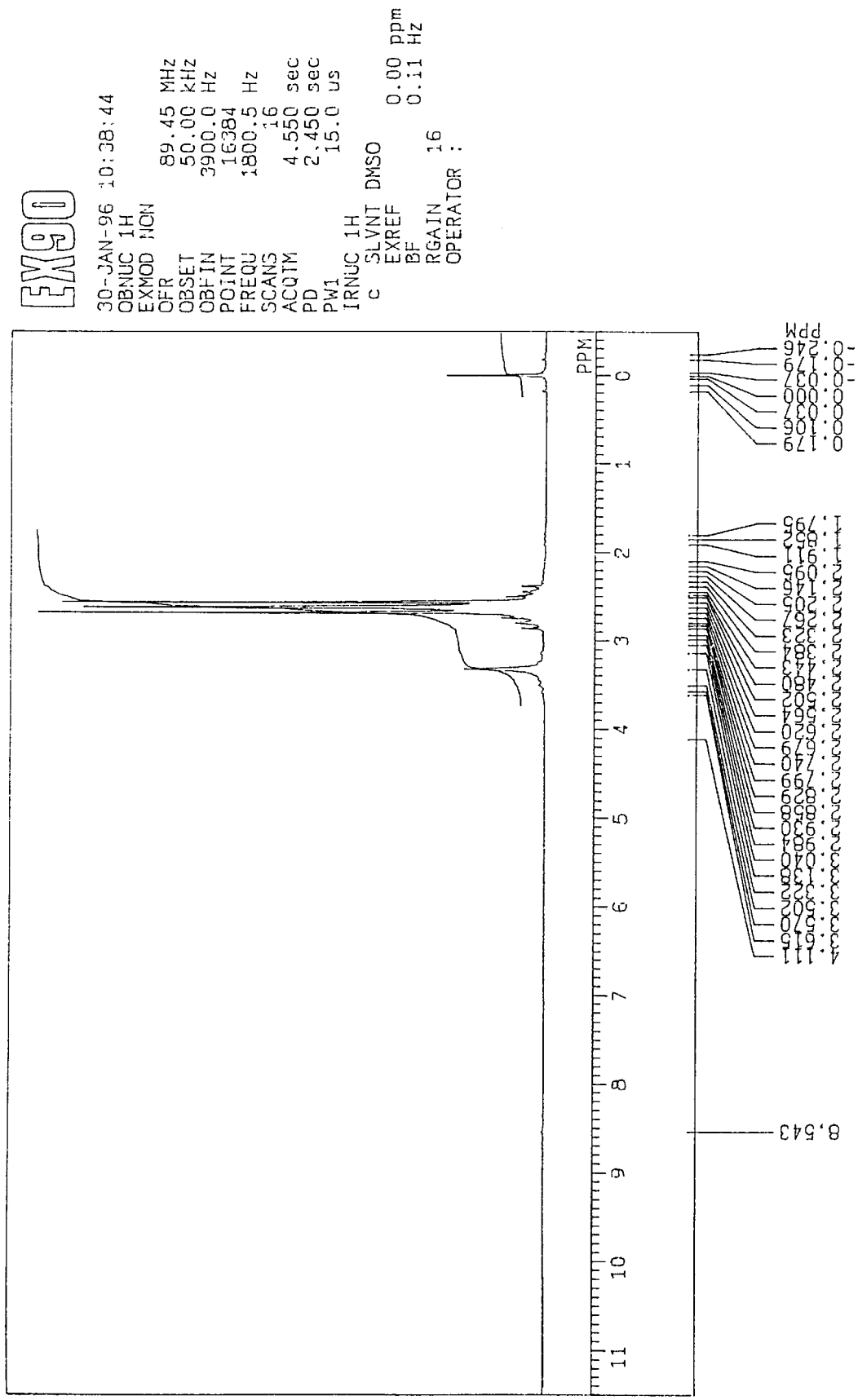
FIG. 23 is a ¹H-NMR (solvent: DMSO-d₆) spectrum of the di{tris(dimethylamino)[tris(dimethylamino) phosphoranilideneamino]phosphonium} salt of glycerol.

| Ex. | Active hydrogen compound Rational formula of product* | Yield (%) | Elemental analysis (wt. %) Found: Calculated: | $^1$H-NMR*** |
|---|---|---|---|---|
| 12 | t-C$_4$H$_9$OH (Me$_2$N)$_3$[(Me$_2$)$_3$P=N]P$^+$(t-C$_4$H$_9$O)$^-$ | 91 | C 46.91, H 10.81, N 22.98, P 15.68 C 46.47, H 10.97, N 23.71, P 14.98 | FIG. 19 |
| 13 | C$_6$H$_5$CH$_2$OH (Me$_2$N)$_3$[(Me$_2$)$_3$P=N]P$^+$(C$_6$H$_5$CH$_2$O)$^-$ | 85 | C 51.61, H 9.21, N 21.48, P 15.02 C 50.99, H 9.68, N 21.91, P 13.84 | FIG. 20 |
| 14 | HOCH$_2$CH$_2$OH (Me$_2$N)$_3$[(Me$_2$)$_3$P=N]P$^+$(HOCH$_2$CH$_2$O)$^-$ | 95 | C 40.98, H 10.81, N 25.11, P 15.21 C 41.88, H 10.29, N 24.43, P 15.43 | FIG. 21 |
| 15 | Glycerol (Me$_2$N)$_3$[(Me$_2$)$_3$P=N]P$^+$Gly$^-$ | 96 | C 42.01, H 10.97, N 22.15, P 15.02 C 41.75, H 10.04, N 22.73, P 14.36 | FIG. 22 |
| 16 | Glycerol {(Me$_2$N)$_3$[(Me$_2$)$_3$P=N]P$^+$}$_2$Gly$^{2-}$ | 98 | C 42.43, H 10.85, N 25.11, P 15.61 C 42.07, H 10.20, N 25.44, P 16.07 | FIG. 23 |

TABLE 1-continued

Figure 24:
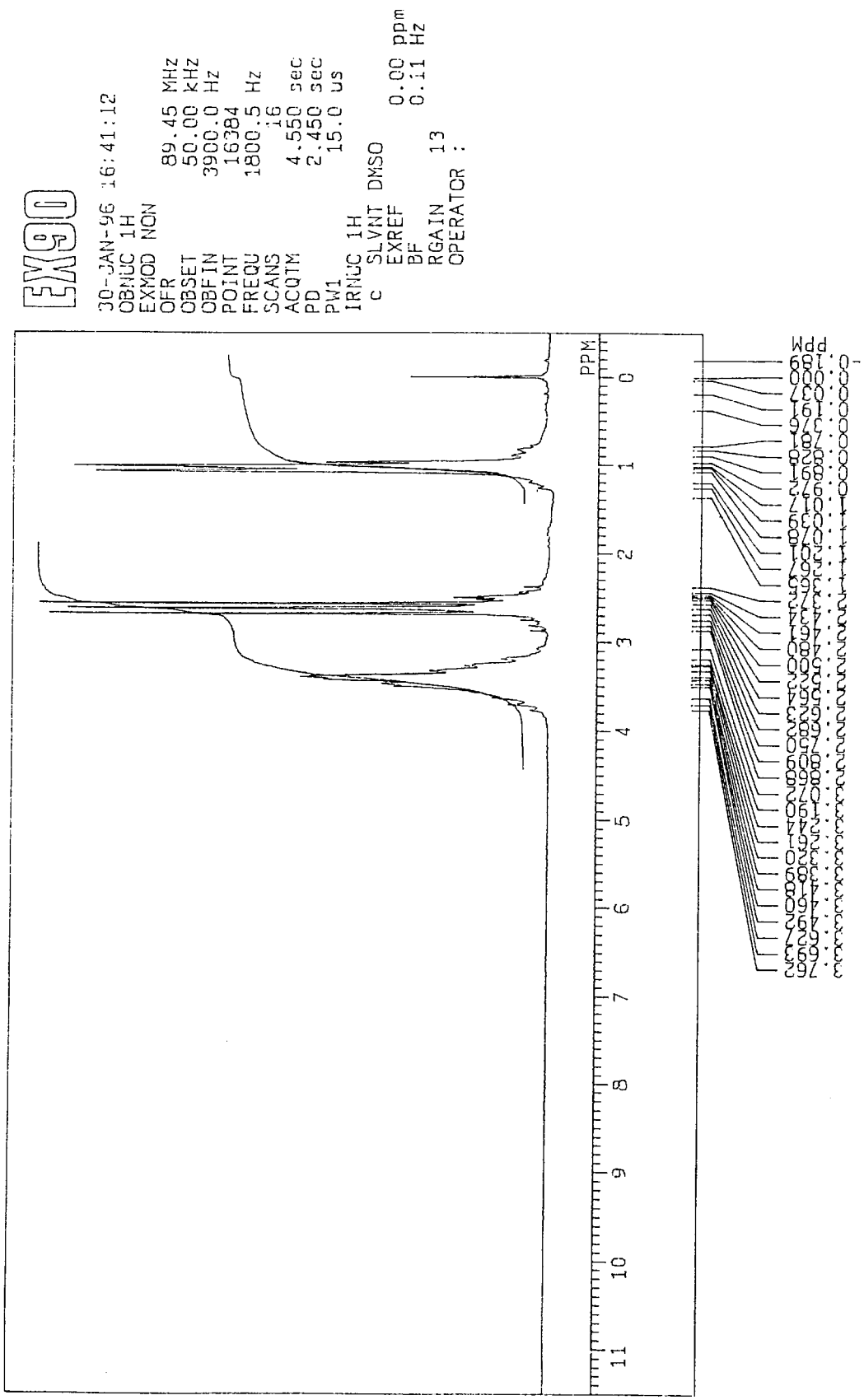
FIG. 24 is a ¹H-NMR (solvent: DMSO-d₆) spectrum of the mono{tris(dimethylamino)[tris(dimethylamino) phosphoranilideneamino]phosphonium} salt of polyoxypropylenetriol.

| Ex. | Active hydrogen compound Rational formula of product* | Yield (%) | Elemental analysis (wt. %) Found: Calculated: | $^1$H-NMR*** |
|---|---|---|---|---|
| 17 | Polyoxypropylenetriol** $(Me_2N)_3[(Me_2)_3P=N]P^+POPT^-$ | 98 | C 55.98, H 10.06, N 7.98, P 4.18 C 55.27, H 10.25, N 7.28, P 4.61 | FIG. 24 |

*Gly$^-$, Gly$^{2-}$ and POPT$^-$ represent a monovalent glycerol anion, a divalent glycerol anion and a monovalent polyoxypropylenetriol anion, respectively.
**"MN1000", trade name; product of Mitsui-Toatsu Chemicals Inc.
***All $^1$H-NMR measurements were conducted using DMSO-d$_6$ as a solvent.

EXAMPLE 18–23

In a similar manner as in Example 1 except for the use of various phosphazenium salts and various basic alkali metal compounds shown in Table 2 instead of tetrakis[tris(dimethylamino)phosphoranilideneamino]phosphonium chloride and sodium hydride, six samples of the tris(dimethylamino)[tris(dimethylamino) phosphoranilideneamino]phosphonium salt of methanol were synthesized. All the six samples had melting points in a range of 265–268° C. (with decomposition), and their $^1$-NMR spectra were identical to that obtained in Example 1. The results are presented in Table 2.

TABLE 2

| Ex. | Phosphazenium salt | Alkali metal compound | Yield (%) |
|---|---|---|---|
| 18 | $(Me_2N)_3[(Me_2N)_3P=N]P^+Cl^-$ | KH | 88 |
| 19 | $(Me_2N)_3[(Me_2N)_3P=N]P^+PF_6^-$ | NaH | 95 |
| 20 | $(Me_2N)_3[(Me_2N)_3P=N]P^+ClO_4^-$ | t-BuLi | 96 |
| 21 | $(Me_2N)_3[(Me_2N)_3P=N]P^+H_2PO_4^-$ | NaH | 56 |
| 22 | $\{(Me_2N)_3[(Me_2N)_3P=N]P^+\}_2HPO_4^{2-}$ | NaH | 61 |
| 23 | $\{(Me_2N)_3[(Me_2N)_3P=N]P^+\}_3PO_4^{3-}$ | NaH | 81 |

The various phosphazenium salts employed in Examples 18–23 were synthesized by the following procedures:

(Synthesis of tris(dimethylamino)[tris (dimethylamino)phosphoranilideneamino] phosphonium chloride, $(Me_2N)_3[(Me_2)_3P=N]P^+$ Cl$^-$, employed in Example 18)

In 100 ml of methanol, 15.75 g of a Cl$^-$-form ion-exchange resin ("Amberlite IRA-400, Cl-form", trade name; product of Organo Corporation) were suspended, followed by the addition of 5.0 (11.7 mmol) of tris(dimethylamino)[tris(dimethylamino)phosphoranilideneamino]phosphonium tetrafluoroborate. After the resultant mixture was stirred at room temperature for 2 hours, the resin was collected by filtration and then washed twice with 50-ml portions of methanol. The filtrate and washings were combined and concentrated to dryness, whereby 4.22 g of tris(dimethylamino)[tris(dimethylamino) phosphoranilideneamino phosphonium chloride were obtained as a colorless solid (yield: 92%).

(Synthesis of tris(dimethylamino)[tris (dimethylamino)phosphoranilideneamino] phosphonium hexafluorophosphate, $(Me_2N)_3[(Me_2)$ $_3P=N]P^+PF_6^-$, employed in Example 19)

In 10 ml of water, 600 mg (1.60 mmol) of the tris(dimethylamino)[tris(dimethylamino) phosphoranilideneamino]phosphonium chloride prepared in Example 18 were dissolved, followed by the addition of an aqueous solution of 330 mg (1.96 mmol) of sodium hexafluorophosphate in 2 ml of water. The thus-obtained mixture was stirred for 1 hour. The resultant crystals were collected by filtration, washed twice with 5-ml portions of water, and then dried under reduced pressure, whereby 714 mg of tris(dimethylamino)[tris(dimethylamino) phosphoranilideneamino]phosphonium hexafluorophosphate were obtained as colorless crystals (yield: 92%).

(Synthesis of tris(dimethylamino)[tris (dimethylamino)phosphoranilideneamino] phosphonium perchlorate, $(Me_2N)_3[(Me_2)_3P=N]P^+$ ClO$_4^-$, employed in Example 20)

In exactly the same manner as in Example 19 except for the use of sodium perchlorate instead of sodium hexafluorophosphate in the synthesis of tris(dimethylamino)[tris (dimethylamino)phosphoranilideneamino]phosphonium hexafluorophosphate, 676 mg of tris(dimethylamino)[tris (dimethylamino)phosphoranilideneamino]phosphonium perchlorate was obtained as colorless crystals (yield: 96%).

(Synthesis of tris(dimethylamino)[tris (dimethylamino)phosphoranilideneamino] phosphonium dihydrogenphosphate, $(Me_2N)_3[(Me_2)$ $_3P=N]P^+H_2PO_4^-$, employed in Example 21)

Using an OH-form ion-exchange resin "Amberlite IRA-400, OH-form" (trade name; product of Organo Corporation), tris(dimethylamino)[tris(dimethylamino) phosphoranilideneamino]phosphonium hydroxide was prepared in a similar manner as in the preparation of the phosphazenium salt in Example 18. To 10 ml methanol solution containing 572 mg (1.6 mmol) of the above phosphazenium hydroxide, 784 mg (1.6 mmol) of a 20% aqueous solution of phosphoric acid were added, followed by mixing. The resultant mixture was concentrated to dryness and the residue was heated and dried under reduced pressure, whereby 701 mg of tris(dimethylamino)[tris (dimethylamino)phosphoranilideneamino]phosphonium dihydrogenphosphate were obtained as a colorless solid (yield: app. 100%).

(Synthesis of bis{tris(dimethylamino)[tris (dimethylamino)phosphoranilideneamino] phosphonium} hydrogenphosphate, $(Me_2N)_3[(Me_2)_3$ $P=N]P^+\}_2HPO_4^{2-}$, employed in Example 22)

The procedures in the above-described synthesis of tris(dimethylamino)[tris(dimethylamino) phosphoranilideneamino]phosphonium dihydrogenphosphate were repeated in exactly the same manner except that the amount of phosphoric acid was reduced to ½, whereby 621 mg of bis{tris(dimethylamino)[tris(dimethylamino) phosphoranilideneamino]phosphonium hydrogenphosphate were obtained as a colorless solid (yield: app. 100%).

(Synthesis of tris{tris(dimethylamino)[tris(dimethylamino)phosphoranilideneamino]phosphonium} phosphate, $(Me_2N)_3[(Me_2)_3P=N]P^+\}_3PO_4^{3-}$, employed in Example 23)

The procedures in the above-described synthesis of tris(dimethylamino)[tris(dimethylamino)phosphoranilideneamino]phosphonium dihydrogenphosphate were repeated in exactly the same manner except that the amount of phosphoric acid was reduced to ⅓, whereby 598 mg of tris{tris(dimethylamino)[tris(dimethylamino)phosphoranilideneamino]phosphonium phosphate were obtained as a colorless solid (yield: app. 100%).

REFERENCE 1

(Example showing the usefulness of the phosphazenium salt of the active hydrogen compound according to the present invention: Synthesis of benzyl methyl ether)

To a solution of 1.57 g (10 mmol) of benzyl chloride in 40 ml of benzene, 5.57 g (15 mmol) of the tris(dimethylamino)[tris(dimethylamino)phosphoranilideneamino]phosphonium salt of methanol, said salt having had been synthesized in a similar manner as in Example 1, were added at 0° C., followed by a reaction at room temperature for 3 hours. Water (50 ml) was then added to the reaction mixture to terminate the reaction. An organic layer was separated, washed successively with 20 ml of water and 20 ml of a saturated aqueous solution of sodium chloride, and then concentrated to dryness. The resulting liquid compound was distilled, whereby benzyl methyl ether, the target compound, was obtained as a colorless liquid compound in an amount of 1.13 g. Its yield was 93%.

EXAMPLE 24

Figure 25:
FIG. 25 is a ³¹P-NMR (solvent: DMSO-d₆) spectrum of tetrakis[tris(dimethylamino)phosphoranilideneamino] phosphonium hydroxide.
Figure 26:
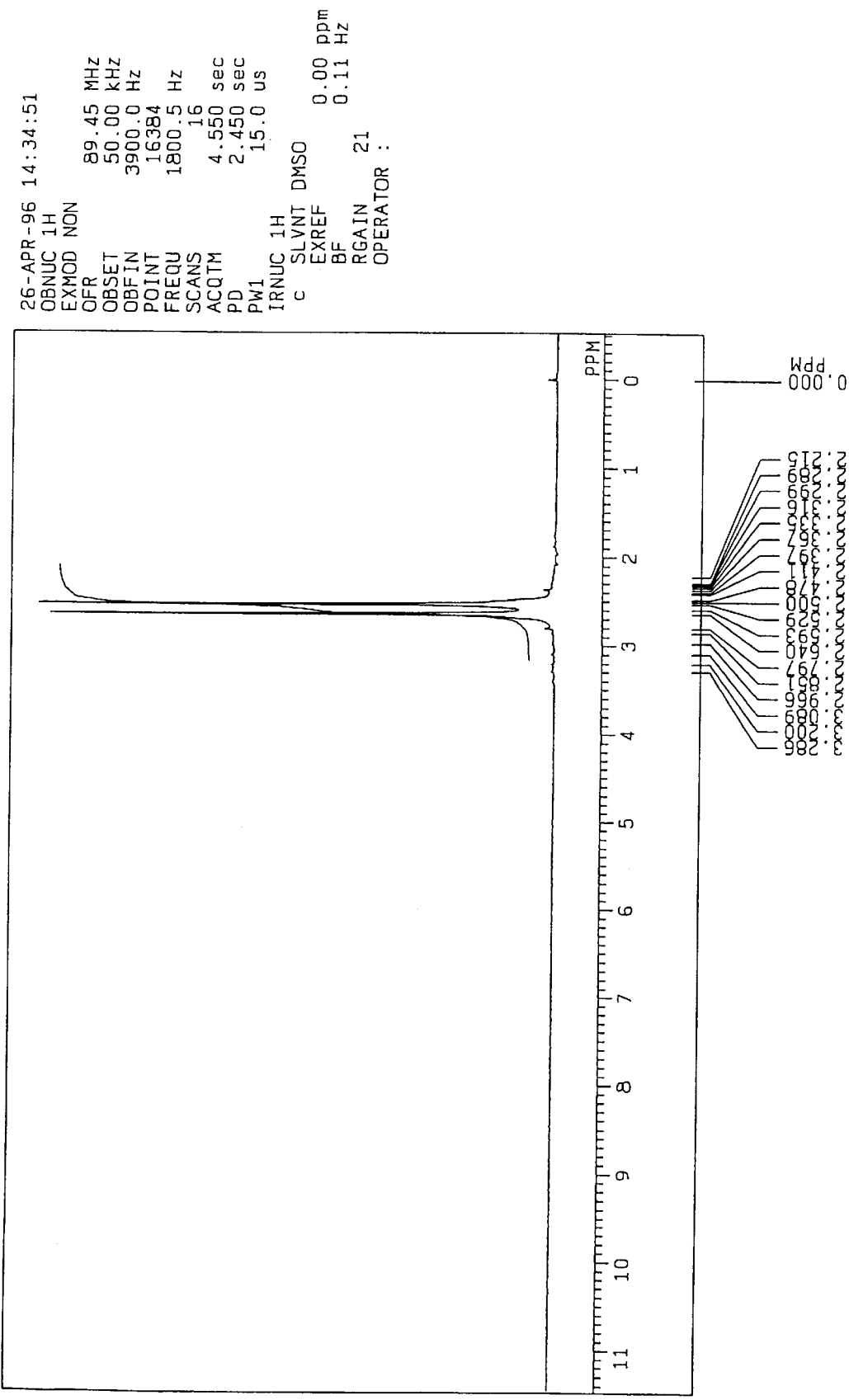
FIG. 26 is a ¹H-NMR (solvent: DMSO-d₆) spectrum of tetrakis[tris(dimethylamino)phosphoranilideneamino] phosphonium hydroxide.

Tetrakis[tris(dimethylamino)phosphoranilideneamino]phosphonium chloride (31.02 g, 40 mmol) was dissolved in 200 ml of a mixed solvent of 50% (wt. %, this will hereinafter apply equally) methanol-water so that a 0.2 M solution was prepared. That solution was caused to flow at a flow rate of 140 ml/hr and room temperature through a column (diameter: 20 mm, height: 450 mm) which was packed with 140 ml of an OH⁻-form anion-exchange resin ("Levatit MP500", trade name; product of Bayer AG), and 450 ml of a mixed solvent of 50% methanol-water were then caused to flow at the same flow rate. After an effluent was concentrated, the concentrate was dried at 80° C. and 1 mmHg. The residue was recrystallized form a 1:15 mixed solvent of THF and diethyl ether, whereby 28.76 g of tetrakis[tris(dimethylamino)phosphoranilideneamino]phosphonium hydroxide $\{[(Me_2N)_3P=N]_4P^+OH^-\}$ were obtained as colorless crystals. Its yield was 95%. Its melting point was 300° C. or higher. A $^{31}$P-NMR spectrum of its MDSO-$d_6$ solution is shown in FIG. 25. Further, a chemical shift by $^1$H-NMR, in which TMS was used as an internal reference, was observed at 2.59 (d,J=9.9 Hz, 72H) ppm (FIG. 26). Its elemental analysis data were: C, 38.28; H, 9.82; N, 29.43; P, 19.94; (calculated: C, 38.09; H, 9.72; N, 29.61; P, 20.46).

COMPARATIVE EXAMPLE 1

An attempt was made to prepare a 0.2 M aqueous solution of the same tetrakis[tris(dimethylamino)phosphoranilideneamino]phosphonium chloride as that used in Example 24 by dissolving 31.02 g (40 mmol) of the salt in 200 ml of water. Some of the salt however remained undissolved.

COMPARATIVE EXAMPLE 2

By repeating the procedures of Example 24 in exactly the same manner except for the use of methanol instead of the mixed solvent of 50% methanol-water, colorless crystals were obtained. By a silver nitrate titration and an ion-selective electrode analysis, substantial chlorine ions were detected in the crystals.

EXAMPLE 25–28

In each example, the procedures of Example 24 were repeated in exactly the same manner except that instead of tetrakis[tris(dimethylamino)phosphoranilideneamino]phosphonium chloride, the salt of the phosphazenium cation and the monovalent inorganic anion shown in Table 3 was used in the same amount (40 mmol) and that the mixed solvent shown in Table 3 was employed in place of the mixed solvent of 50% methanol-water. All the four samples so obtained had melting points of 300° C. or higher, and their $^1$H-NMR and $^{31}$P-NMR spectra were equivalent to those obtained in Example 24. The results are presented in Table 3.

TABLE 3

| Ex. | Salt of phosphazenium cation and monovalent inorganic anion | Mixed solvent (wt. ratio) | Yield (%) |
|---|---|---|---|
| 25 | $[(Me_2N)_3P=N]_4P^+BF^-$ | Acetonitrile:water (80:20) | 93 |
| 26 | $[(Me_2N)_3P=N]_4P^+ClO_4^-$ | Propanol:water (80:20) | 94 |
| 27 | $[(Me_2N)_3P=N]_4P^+PF_6^-$ | Methanol:water (85:15) | 96 |
| 28 | $[(Me_2N)_3P=N]_4P^+Cl^-$ | Tetrahydrofuran:water (70:30) | 94 |

EXAMPLE 29

Figure 27:
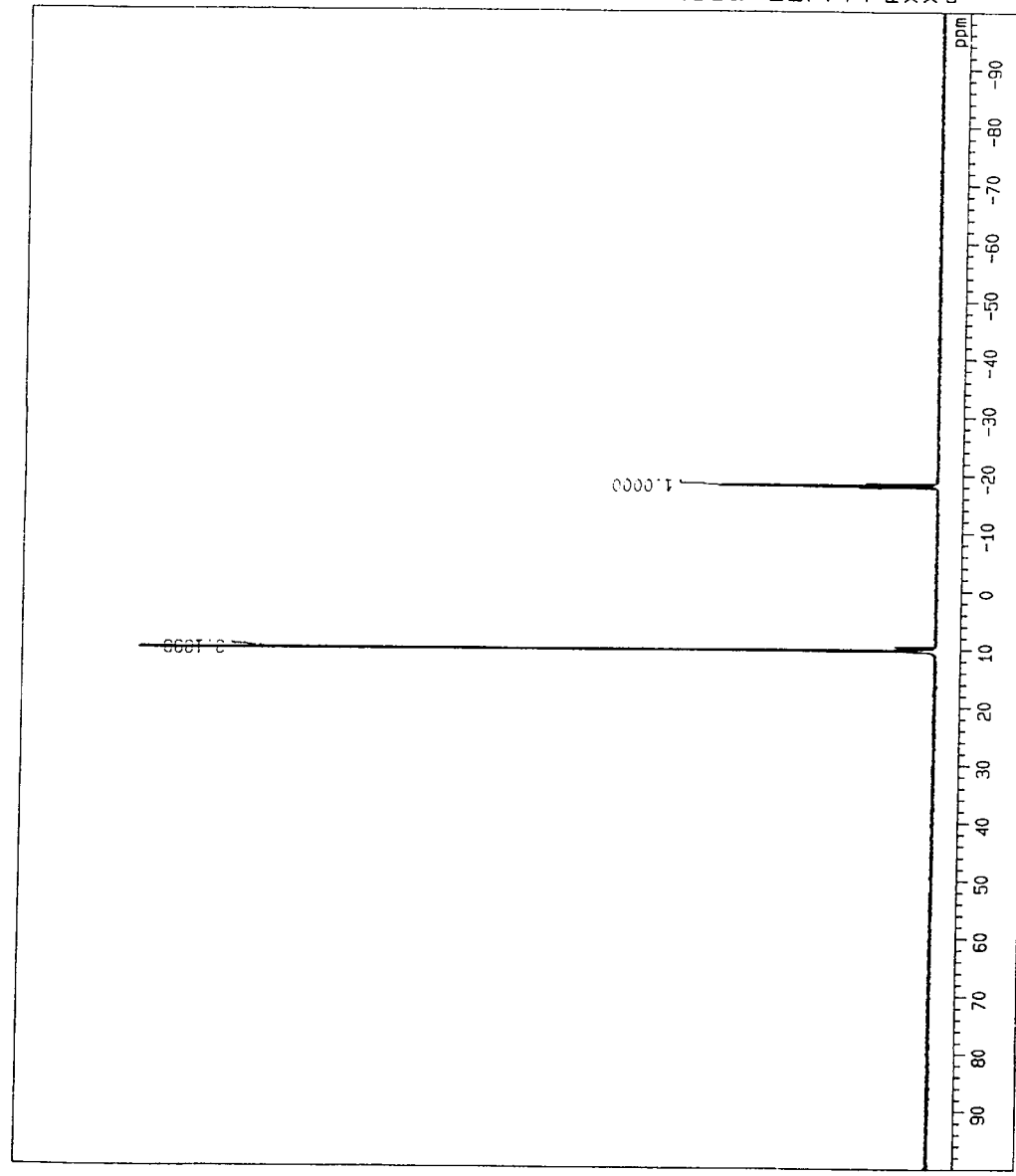
FIG. 27 is a ³¹P-NMR (solvent: DMSO-d₆) spectrum of dimethylaminotris[tris(dimethylamino) phosphoranilideneamino]phosphonium hydroxide.
Figure 28:
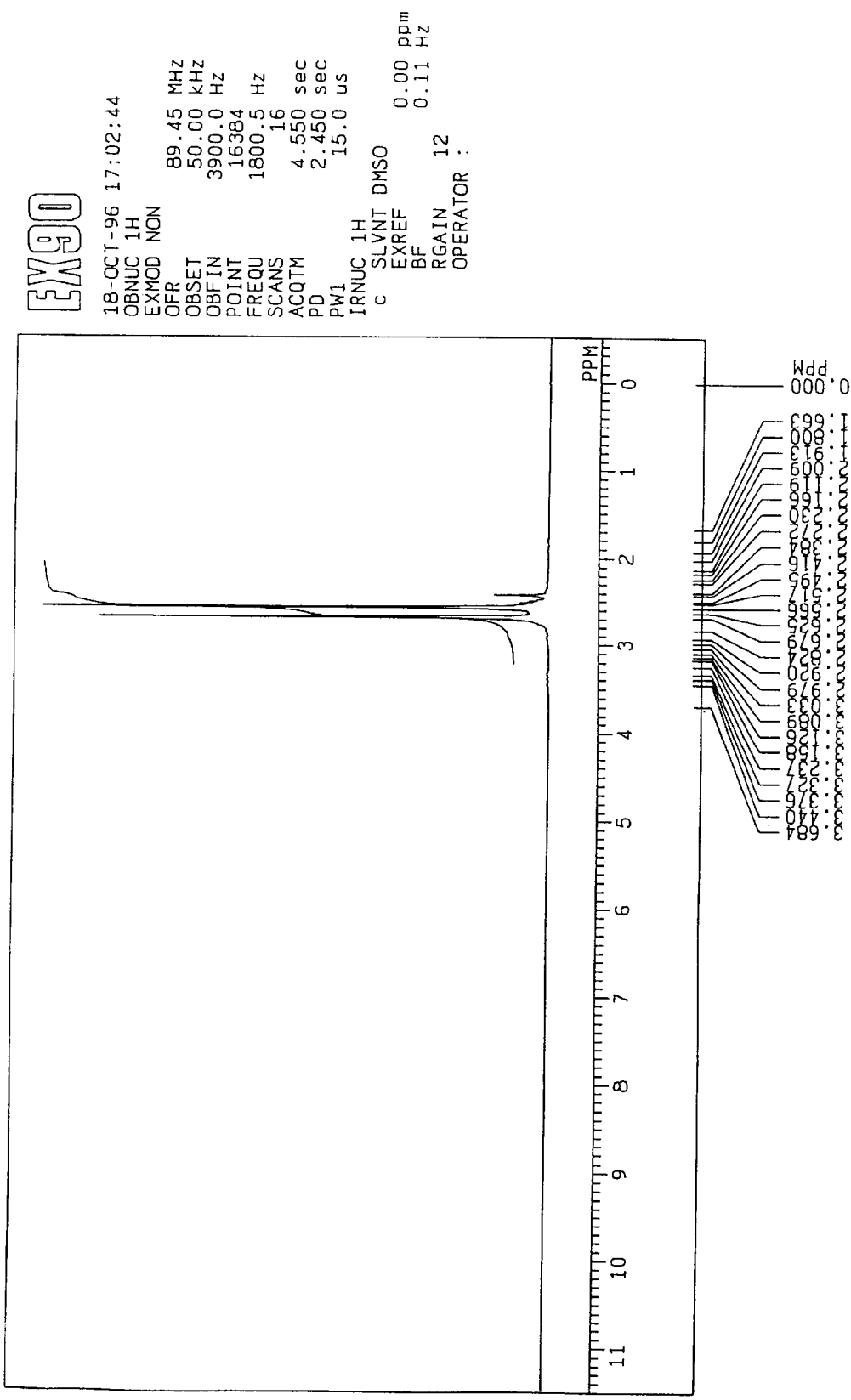
FIG. 28 is a ¹H-NMR (solvent: DMSO-d₆) spectrum of dimethylaminotris[tris(dimethylamino) phosphoranilideneamino]phosphonium hydroxide.

By repeating the procedures of Example 24 in exactly the same manner except that instead of tetrakis[tris(dimethylamino)phosphoranilideneamino]phosphonium chloride, dimethylaminotris[tris(dimethylamino)phosphoranilideneamino]phosphonium tetrafluoroborate synthesized in a similar manner as in Example 10 was used in the same amount (40 mmol, 27.74 g) and that recrystallization was not conducted, 24.60 g of dimethylaminotris[tris(dimethylamino)phosphoranilideneamino]phosphonium hydroxide, $\{Me_2N[(Me_2N)_3P=N]_3P^+OH^-\}$, were obtained as a pale yellow oily substance. Its yield was 91%. A $^{31}$P-NMR and $^1$H-NMR spectra of its DMSO-$d_6$ solution are shown in FIG. 27 and FIG. 28, respectively. Its elemental analysis data were: C, 38.12; H, 10.21; N, 29.01; P, 20.22; (calculated: C, 38.52; H, 9.86; N, 29.20; P, 19.86).

EXAMPLE 30

Figure 29:
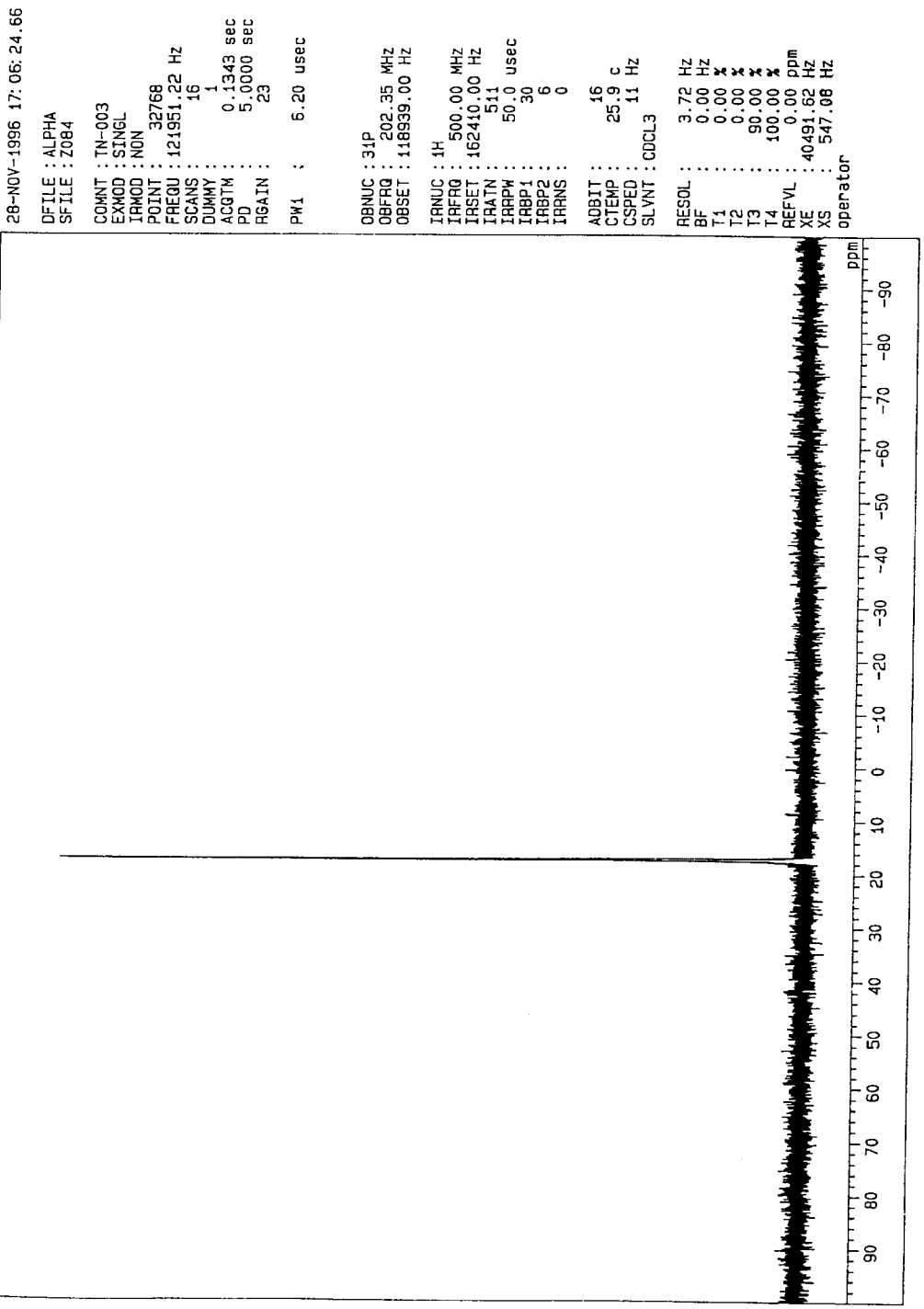
FIG. 29 is a ³¹P-NMR (solvent: DMSO-d₆) spectrum of tris(dimethylamino)[tris(dimethylamino) phosphoranilideneamino]phosphonium hydroxide.
Figure 30:
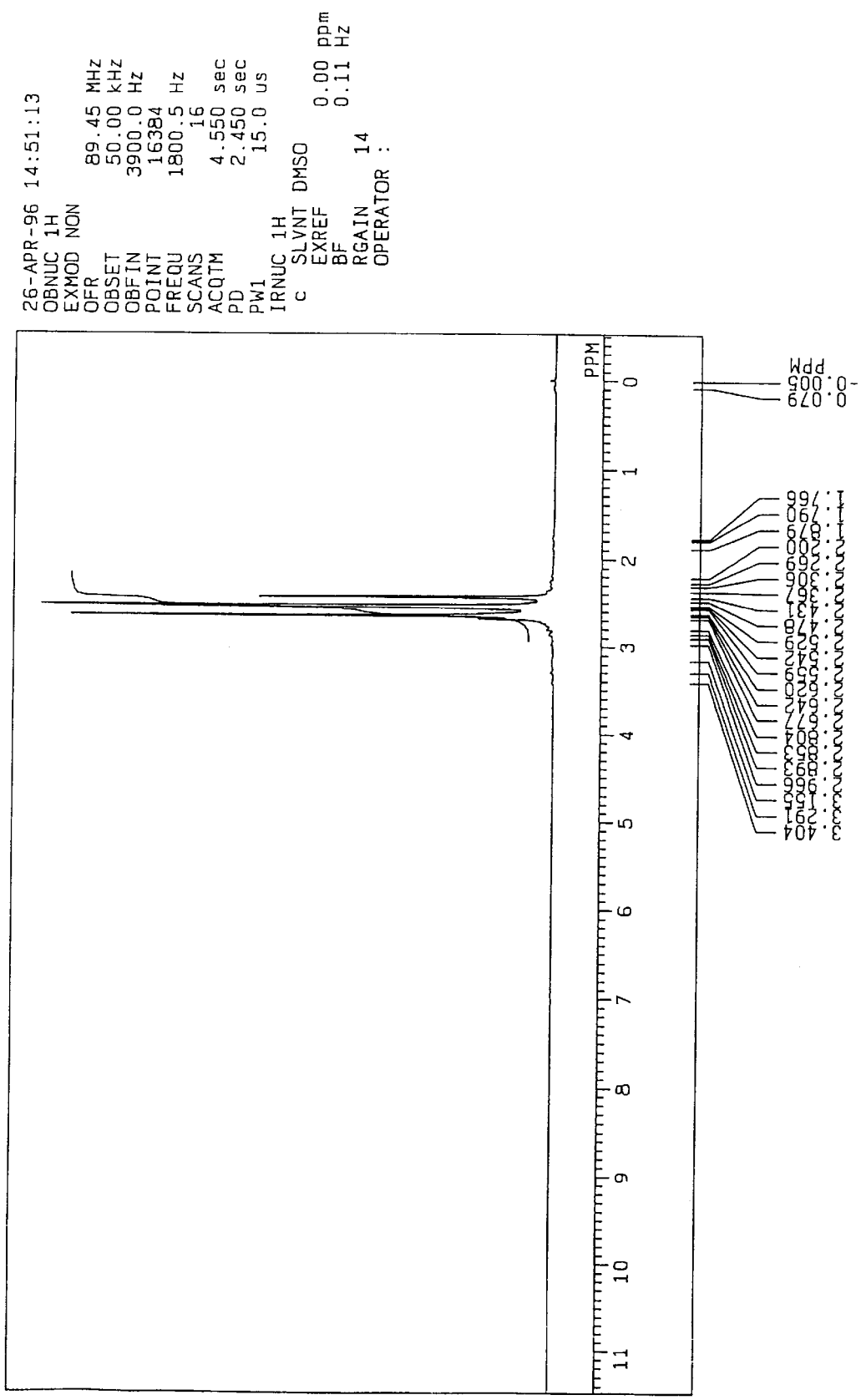
FIG. 30 is a ¹H-NMR (solvent: DMSO-d₆) spectrum of tris(dimethylamino)[tris(dimethylamino) phosphoranilideneamino]phosphonium hydroxide.

By repeating the procedures of Example 24 in exactly the same manner except that instead of tetrakis[tris(dimethylamino)phosphoranilideneamino]phosphonium chloride, tris(dimethylamino)[tris(dimethylamino)phosphoranilideneamino]phosphonium tetrafluoroborate was used in the same amount (40 mmol, 17.09 g) and that recrystallization was not conducted, 13.87 g of tris(dimethylamino)[tris(dimethylamino)phosphoranilideneamino]phosphonium hydroxide, $\{(Me_2)_3N[(Me_2N)_3P=N]P^+OH^-\}$, were obtained as a colorless oily substance. Its yield was 97%. A $^{31}$P-NMR spectrum of its DMSO-$d_6$ solution is shown in FIG. 29. Further, a chemical shift by $^1$H-NMR, in which TMS was used as an internal reference, was observed at 2.40–2.70 (m,36H) ppm (FIG. 30). Its elemental analysis data were: C, 40.71; H, 10.15; N, 27.04; P, 17.81; (calculated: C, 40.33; H, 10.43; N, 27.43; P, 17.33).

REFERENCE 2

In a 200-ml eggplant-type flask, 5.3 g (37.0 mmol) of 4-chlorobenzyl alcohol were weighed. After 80 ml of o-xylene, a nonpolar solvent, were added to form a solution, 28.0 g (37.0 mmol) of tetrakis[tris(dimethylamino)phosphoranilideneamino]phosphonium hydroxide was added to form a homogeneous solution. The solution was heated to 80° C., at which it was then maintained at 5 mmHg for 1 hour. Its pressure was allowed to rise back to normal pressure by nitrogen, followed by cooling to room temperature. Further, 50 ml of o-xylene and 5.20 g (37.0 mmol) of 4-chlorobenzaldehyde were added, followed by heating at 130° C. for 96 hours. The reaction mixture was washed four times with 100-ml portions of 1 N hydrochloric acid. The organic layer was separated and then concentrated to dryness. The residue was recrystallized from ethanol, whereby 5.6 g of 4-(4-chlorobenzyloxy)benzaldehyde were obtained as colorless crystals. Its isolation yield was 61%.

A description will next be made about production examples of poly(alkylene oxides).

EXAMPLE 31

Glycerol (460 mg, 5.0 mmol) was weighed in a 50-ml eggplant-type flask, to which 5.0 ml (5.0 mmol) of a 1.0 N aqueous solution of potassium hydroxide were added at room temperature to form a homogeneous solution. Under reduced pressure, the solution was concentrated to dryness so that colorless crystals were obtained. The crystals were heated and dried further at 100° C. under reduced pressure, whereby the monopotassium salt of glycerol was synthesized. To the salt, a solution of 3.78 g (5.0 mmol) of tetrakis[tris(dimethylamino)phosphoranilideneamino]phosphonium chloride in 20 ml of THF was added, followed by stirring at room temperature for 24 hours. After precipitated KCl was filtered off under a nitrogen gas atmosphere, the filtrate was concentrated to dryness under reduced pressure so that the mono{tetrakis[tris(dimethylamino)phosphoranilideneamino]phosphonium} salt of glycerol, namely, [(Me$_2$N)$_3$P=N]$_4$P$^+$(Gly)$^-$ ("Gly$^-$" represents a monovalent anion of glycerol; this will hereinafter apply equally) was synthesized.

In an autoclave having an actual capacity of 600 ml and equipped with a temperature measuring tube, a pressure gauge, a stirrer and an alkylene oxide inlet tube, charged was a solution of 4.05 g (5.0 mmol) of the phosphazenium salt or the active hydrogen compound synthesized by the above-described procedures, i.e., mono{tetrakis[tris(dimethylamino)phosphoranilideneamino]phosphonium salt of glycerol in 20 ml of THF, followed by the addition of 20.0 g (217 mmol) of fresh glycerol. The resulting mixture was heated with stirring under reduced pressure so that the THF was distilled off. After that, the reactor was purged with dry nitrogen gas and its contents were heated to 100° C. While intermittently feeding propylene oxide so that the pressure during the reaction remained around 3.0 kg/cm$^2$ (absolute pressure; this will hereinafter apply equally), the contents were reacted at 100° C. for 6 hours. The contents were then allowed to cool down to room temperature, and the remaining unreacted propylene oxide was distilled off under reduced pressure. Colorless, odorless, liquid polyoxypropylenetriol was obtained in an amount of 324 g. Its hydroxyl number (KOH-mg/g-polymer; this will hereinafter apply equally) was 115.

COMPARATIVE EXAMPLE 3

A polymerization reaction was conducted in exactly the same manner as the polymerization reaction of Example 31 except that the THF solution of the mono{tetrakis[tris(dimethylamino)phosphoranilideneamino]phosphonium salt of glycerol was not used and that the distillation operation of THF was hence omitted. Propylene oxide was not consumed at all and the weight of the contents of the autoclave was 20.1 g. This weight was substantially the same as the weight of the glycerol itself charged in the autoclave, and no polyoxypropylenetriol was obtained.

EXAMPLE 32

A polymerization reaction was conducted in exactly the same manner as the polymerization reaction of Example 31 except that fresh glycerol was not used and that the reaction time was changed to 20 hours. Colorless, odorless, liquid polyoxypropylenetriol of high viscosity was obtained in an amount of 161 g. Its hydroxyl number was 5.4. A polymer of high molecular weight was obtained.

EXAMPLE 33

Glycerol (20.5 g, 222 mmol) was weighed in a 100-ml eggplant-type flask, to which 5.0 ml (5.0 mmol) of a 1.0 N aqueous solution of potassium hydroxide were added to form a homogeneous solution. Dry nitrogen gas was then bubbled at 110° C. under reduced pressure to remove water, whereby the monopotassium salt of glycerol was prepared in a form contained in excess glycerol. To the salt, a solution of 3.78 g (5.0 mmol) of tetrakis[tris(dimethylamino)phosphoranilideneamino]phosphonium chloride in 20 ml of THF was added, followed by stirring to obtain a suspension.

In an autoclave similar to that employed in Example 31, the suspension obtained by the above-described procedures was charged. The suspension was heated with stirring under reduced pressure so that the THF was distilled off. After that, the reactor was purged with dry nitrogen gas and its contents were heated to 100° C. While intermittently feeding propylene oxide so that the pressure during the reaction remained around 3.0 kg/cm$^2$, the contents were reacted at 100° C. for 6 hours. The contents were then allowed to cool down to room temperature, and the remaining unreacted propylene oxide was distilled off under reduced pressure. Colorless, odorless polyoxypropylenetriol was obtained in an amount of 330 g. Its hydroxyl number was 114.

COMPARATIVE EXAMPLE 4

In a similar manner as the former stage of Example 33, the monopotassium salt of glycerol was prepared in a form contained in excess glycerol. Without addition of tetrakis[tris(dimethylamino)phosphoranilideneamino]phosphonium chloride to the salt, 20 ml of THF were added so that a suspension was obtained. A polymerization reaction was conducted in exactly the same manner as the polymerization reaction of Example 33 except that the above-prepared suspension was used in place of the suspension employed in Example 33. The reaction was extremely slow and propylene oxide was consumed only slightly. The contents of the autoclave was 23 g, which was only slightly greater than the weight of the charged glycerol itself.

EXAMPLE 34–37

In each example, the procedures of Example 33 were repeated likewise except that instead of glycerol, the active hydrogen compound shown in Table 4 was used in the amount also indicated in the same table. The results are presented together with the results of Example 33 in Table 4.

TABLE 4

| Ex. | Active hydrogen compound | mmol | Yield(g) | Hydroxyl number |
|---|---|---|---|---|
| 33 | Glycerol | 222 | 330 | 114 |
| 34 | Ethylene glycol | 220 | 294 | 86 |
| 35 | Trimethylolpropane | 220 | 357 | 106 |
| 36 | 1,4-butanediol | 220 | 289 | 88 |
| 37 | Propylene glycol and 1,6-hexanediol | 110 110 | 315 | 80 |

Note: Two kinds of active hydrogen compounds were used in Example 37.

EXAMPLE 38

In exactly the same manner as in the former stage of Example 33, a suspension was obtained. In an autoclave similar to that employed in Example 33, the above-obtained suspension was charged. Without distilling off THF, it was employed as a solvent for a polymerization reaction. The reactor was purged with dry nitrogen gas and its contents were heated to 100° C. under stirring. While intermittently feeding propylene oxide so that the pressure during the reaction remained around 3.0 kg/cm², the contents were reacted at 100° C. for 6 hours. The remaining unreacted propylene oxide and the solvent were distilled off under reduced pressure. Colorless, odorless polyoxypropylenetriol was obtained in an amount of 390 g. Its hydroxyl number was 97.

EXAMPLE 39–41

In each example, the procedures of Example 38, namely, Example 33 were repeated in exactly the same manner except that instead of glycerol, the active hydrogen compound shown in Table 5 was used in the same amount (222 mmol) and that in place of THF, the solvent shown in Table 5 was used in the same amount (20.0 ml). The results are presented together with the results of Example 38 in Table 5.

TABLE 5

| Ex. | Active hydrogen compound | Solvent | Yield(g) | Hydroxyl number |
|---|---|---|---|---|
| 38 | Glycerol | THF | 390 | 97 |
| 39 | Pentaerythritol | DMSO | 386 | 132 |
| 40 | Glucose | DMF | 419 | 151 |
| 41 | 2-Naphthol | Benzene | 264 | 48 |

Note: "DMSO" and "DMF" represent "dimethyl sulfoxide" and "N,N-dimethylformamide", respectively.

EXAMPLE 42

In a 100-ml eggplant-type flask, weighed were 20.0 g (20.0 mmol) of polyoxypropylenetriol which had a hydroxyl number of 168 and had been industrially produced using glycerol and potassium hydroxide as initiators (product of Mitsui-Toatsu Chemicals Inc.). A 0.1 N aqueous solution of potassium hydroxide (4.6 ml, 0.46 mmol) was added, followed by stirring to obtain a suspension. The suspension was heated to 110° C., at which dry nitrogen gas was bubbled under reduced pressure to remove water, whereby the monopotassium salt of polyoxypropylenetriol was formed. To the salt, a solution of 347 mg (0.46 mmol) of tetrakis[tris(dimethylamino)phosphoranilideneamino]phosphonium chloride in 20 ml of THF was added, followed by stirring to obtain a suspension.

A polymerization reaction was conducted in exactly the same manner as the polymerization reaction of Example 33 except that instead of the THF suspension obtained from the monopotassium salt of glycerol and tetrakis[tris(dimethylamino)phosphoranilideneamino]phosphonium chloride, the suspension obtained from the monopotassium salt of polyoxypropylenetriol and tetrakis[tris(dimethylamino)phosphoranilideneamino]phosphonium chloride by the above-described procedures was used. Colorless, odorless, liquid polyoxypropylenetriol was obtained in an amount of 231 g. Its hydroxyl number was 15.

EXAMPLE 43

Ethylenediamine (13.3 g, 222 mmol) was weighed in a 100-ml eggplant-type flask. Subsequent to dilution with 20 ml of THF, the resultant solution was cooled to −70° C., followed by the addition of 5.0 ml of a 1.0 M solution of n-butyl lithium in hexane (5.0 mmol in terms of n-butyl lithium). After the resultant mixture was stirred at the same temperature for 10 minutes, its temperature was allowed to rise back to room temperature over about 30 minutes, and the mixture was stirred for further 30 minutes so that the monolithium salt of ethylenediamine was obtained. A solution of 3.78 g (5.0 mmol) of tetrakis[tris(dimethylamino)phosphoranilideneamino]phosphonium chloride in 20 ml of THF was added to the salt, followed by stirring for 2 hours to obtain a homogeneous solution.

A polymerization reaction was conducted in exactly the same manner as the polymerization reaction of Example 33 except that instead of the THF suspension, the THF solution obtained above from the monolithium salt of ethylenediamine and tetrakis[tris(dimethylamino)phosphoranilideneamino]phosphonium chloride was used. Slightly brownish, odorless, liquid polyoxypropylenetetraol was obtained in an amount of 204 g. Its hydroxyl number was 250.

EXAMPLE 44–46

In each example, the procedures of Example 43 were repeated in exactly the same manner except that instead of ethylenediamine, the amine compound shown in Table 6 was used in the same amount (222 mmol). The results are presented together with the results of Example 43 in Table 6.

TABLE 6

| Ex. | Active hydrogen compound | Yield(g) | Hydroxyl number |
|---|---|---|---|
| 43 | Ethylenediamine | 204 | 250 |
| 44 | N,N'-Dimethylethylenediamine | 227 | 112 |
| 45 | Piperazine | 214 | 119 |
| 46 | Piperidine | 201 | 64 |

EXAMPLE 47–60

In each example, the procedures of Example 33 were repeated in exactly the same manner except that instead of tetrakis[tris(dimethylamino)phosphoranilideneamino] phosphonium chloride, the phosphazenium chloride shown in Table 7 was used in the same amount (5.0 mmol). The results are presented in Table 7. The phosphazenium chlorides employed in Example 47–52 were synthesized by the process of Example 2, 3, 9 or 10 or a similar process, while the phosphazenium chlorides used in Example 53–60 were each synthesized by reacting hydrogen chloride with a corresponding phosphazene base obtained on the market or synthesized by a conventional process.

glycerol (and hence the amount of potassium hydroxide) were changed as shown in Table 9. The results are presented together with the results of Example 33 in Table 9.

TABLE 7

| Ex. | Phosphazenium salt | Yield(%) | Hydroxyl number |
|---|---|---|---|
| 47 | $(Py_3P=N)_4P^+Cl^-$ | 346 | 110 |
| 48 | $[(Me_2N)_3P=N]_3(Me_2N)P^+Cl^-$ | 328 | 116 |
| 49 | $[(Et_2N)_3P=N]_3(Et_2N)P^+Cl^-$ | 296 | 129 |
| 50 | $(Py_3P=N)_2(Py)_2P^+Cl^-$ | 191 | 199 |
| 51 | $[(Et_2N)_3P=N]_2(Et_2N)_2P^+Cl^-$ | 220 | 174 |
| 52 | $[(Me_2N)_3P=N](Me_2N)_3P^+Cl^-$ | 115 | 329 |
| 53 | $\{Py[Py_2P=N]_2\}[(Me_2N)_3P=N]_2(t-BuNH)P^+Cl^-$ | 340 | 112 |
| 54 | $\{Me_2N[(Me_2N)_2P=N]_2\}[(Me_2N)_3P=N]_2(t-OctNH)P^+Cl^-$ | 349 | 109 |
| 55 | $(Py_3P=N)_3(t-BuNH)P^+Cl^-$ | 305 | 125 |
| 56 | $[(Me_2N)_3P=N]_3(t-OctNH)P^+Cl^-$ | 339 | 112 |
| 57 | $[(Me_2N)_3P=N]_3(t-BuNH)P^+Cl^-$ | 328 | 116 |
| 58 | $[(Me_2N)_3P=N]_2(Me_2N)(t-BuNH)P^+Cl^-$ | 181 | 211 |
| 59 | $[(Me_2N)_3P=N](Me_2N)(EtNH)P^+Cl^-$ | 104 | 365 |
| 60 | $[(Me_2N)_3P=N](Me_2N)(t-BuNH)P^+Cl^-$ | 114 | 330 |

Note: In the table, "n-Oct", "t-Bu", "t-Oct" and "Py" represent "n-octyl", "tert-butyl", "tert-octyl" and "pyrrolidin-1-yl", respectively.

EXAMPLE 61–73

In each example, the procedures of Example 33 were repeated in exactly the same manner except that instead of tetrakis[tris(dimethylamino)phosphoranilideneamino] phosphonium chloride, the inorganic anion salt of phosphazenium shown in Table 8 was used. The various phosphazenium salts employed in these examples were each synthesized from the corresponding phosphazenium chloride by a conventional ion-exchange process or by a reaction between the corresponding phosphazene base or phosphazenium hydroxide and the corresponding acid. The results are presented together with the results of Example 33 in Table 8.

TABLE 8

| Ex. | Phosphazenium salt | Yield (g) | Hydroxyl number |
|---|---|---|---|
| 33 | $[(Me_2N)_3P=N]_4P^+Cl^-$ | 330 | 114 |
| 61 | $[(Me_2N)_3P=N]_4P^+BF_4^-$ | 341 | 111 |
| 62 | $[(Me_2N)_3P=N]_4P^+ClO_4^-$ | 335 | 113 |
| 63 | $[(Me_2N)_3P=N]_4P^+PF_6^-$ | 321 | 118 |
| 64 | $[(Me_2N)_3P=N]_4P^+H_2PO_4^-$ | 338 | 112 |
| 65 | $\{[(Me_2N)_3P=N]_4P^+\}_2HPO_4^{2-}$ | 325 | 116 |
| 66 | $\{[(Me_2N)_3P=N]_4P^+\}_3PO_4^{3-}$ | 320 | 118 |
| 67 | $[(Me_2N)_3P=N]_3(t-OctNH)P^+Cl^-$ | 302 | 126 |
| 68 | $[(Me_2N)_3P=N]_3(t-OctNH)P^+BF_4^-$ | 291 | 130 |
| 69 | $[(Me_2N)_3P=N]_3(t-OctNH)P^+ClO_4^-$ | 285 | 133 |
| 70 | $[(Me_2N)_3P=N]_3(t-OctNH)P^+PF_6^-$ | 296 | 128 |
| 71 | $[(Me_2N)_3P=N]_3(t-OctNH)P^+H_2PO_4^-$ | 309 | 123 |
| 72 | $\{[(Me_2N)_3P=N]_3(t-OctNH)P^+\}_2HPO_4^{2-}$ | 311 | 122 |
| 73 | $\{[(Me_2N)_3P=N]_3(t-OctNH)P^+\}_3PO_4^{3-}$ | 286 | 133 |

Note: In the table, "t-Oct" represents "tert-octyl".

EXAMPLE 74–80

In each example, the procedures of Example 33 were repeated in exactly the same manner except that instead of tetrakis[tris(dimethylamino)phosphoranilideneamino] phosphonium chloride, the kind and amount of the phosphazenium salt and the amount of the monopotassium salt of

EXAMPLE 81–86

In each example, the procedures of Example 33 were repeated in exactly the same manner except that the corresponding alkylene oxide shown in Table 10 was used instead of propylene oxide and that the corresponding phosphazenium salt shown in Table 10 was employed. The results are presented in Table 10.

EXAMPLE 87–89

In each example, the procedures of Example 33 were repeated in exactly the same manner except that the reaction temperature and the pressure during the reaction were changed as shown in Table 11. The results are presented together with the results of Example 33 in Table 11.

TABLE 9

| Ex. | Phosphazenium salt | mmol | $K^+Gly^-$ (mmol) | Yield (g) | Hydroxyl number |
|---|---|---|---|---|---|
| 74 | $[(Me_2N)_3P=N]_4P^+Cl^-$ | 24.9 | 25.0 | 421 | 94 |
| 33 | $[(Me_2N)_3P=N]_4P^+Cl^-$ | 5.0 | 5.0 | 330 | 114 |
| 75 | $[(Me_2N)_3P=N]_4P^+Cl^-$ | 2.5 | 2.5 | 296 | 127 |
| 76 | $[(Me_2N)_3P=N]_3(t-OctNH)P^+Cl^-$ | 25.1 | 24.8 | 418 | 95 |
| 77 | $[(Me_2N)_3P=N]_3(t-OctNH)P^+Cl^-$ | 7.5 | 5.0 | 295 | 130 |
| 78 | $[(Me_2N)_3P=N]_3(t-OctNH)P^+Cl^-$ | 5.0 | 5.0 | 302 | 126 |
| 79 | $[(Me_2N)_3P=N]_3(t-OctNH)P^+Cl^-$ | 3.5 | 5.0 | 291 | 130 |
| 80 | $[(Me_2N)_3P=N]_3(t-OctNH)P^+Cl^-$ | 2.5 | 2.5 | 277 | 136 |

Note: In the table, "$K^+Gly^-$" represents the monopotassium salt of glycerol and "t-oct" stands for "tert-octyl".

TABLE 10

| Ex. | Phosphazenium salt | Alkylene oxide | Yield(g) | Hydroxyl number |
|---|---|---|---|---|
| 81 | [(Me$_2$N)$_3$P=N]$_4$P$^+$Cl$^-$ | Ethylene oxide | 414 | 91 |
| 82 | [(Me$_2$N)$_3$P=N]$_4$P$^+$Cl$^-$ | styrene oxide | 398 | 95 |
| 83 | [(Me$_2$N)$_3$P=N]$_4$P$^+$Cl$^-$ | 1,2-Butylene oxide | 310 | 122 |
| 84 | [(Me$_2$N)$_3$P=N]$_3$(t-Oct-NH)P$^+$Cl$^-$ | Ethylene oxide | 391 | 97 |
| 85 | [(Me$_2$N)$_3$P=N]$_3$(t-Oct-NH)P$^+$Cl$^-$ | Styrene oxide | 411 | 92 |
| 86 | [(Me$_2$N)$_3$P=N]$_3$(t-Oct-NH)P$^+$Cl$^-$ | 1,2-Butylene oxide | 296 | 129 |

Note: In the table, "t-oct" represents "tert-octyl".

TABLE 11

| Ex. | Pressure (Kg/cm$^2$) | Temperature (° C.) | Yield (g) | Hydroxyl number |
|---|---|---|---|---|
| 33 | 3 | 100 | 330 | 114 |
| 87 | 8 | 100 | 375 | 101 |
| 88 | 3 | 110 | 411 | 92 |
| 89 | 3 | 80 | 260 | 146 |

EXAMPLE 90

Glycerol (460 mg, 5.0 mmol) was weighed in a 100-ml eggplant-type flask, to which 50 ml of ethyl ether were added to form a homogeneous solution. Using a dry ice bath, the solution was then cooled to −70° C. After 987 mg (10.5 mmol) of amyl sodium synthesized from amyl chloride and metallic sodium were added at −70° C. to the thus-cooled solution, the resulting mixture was stirred at the same temperature for 30 minutes. The temperature of the mixture was allowed to rise back to room temperature over 1 hour, followed by stirring for 1 hour. To the mixture, 7.75 g (10.0 mmol) of tetrakis[tris(dimethylaminophosphoranilideneamino]phosphonium chloride were added at room temperature. Subsequent to stirring for 6 hours, precipitated NaCl was filtered off under a nitrogen gas atmosphere. The filtrate was concentrated to dryness under reduced pressure, whereby the bis{tetrakis[tris(dimethylaminophosphoranilideneamino]phosphonium} salt of glycerol, namely, {[(Me$_2$N)$_3$P=N]$_4$P$^+$}$_2$(Gly)$^{2-}$ ("(Gly)$^{2-}$" represents a divalent anion of glycerol), was synthesized.

A polymerization reaction was conducted in exactly the same manner as the polymerization reaction of Example 31 except that instead of the phosphazenium salt used in Example 31, the phosphazenium salt of glycerol synthesized by the above-described procedures was used in an amount of 7.64 g (5.0 mmol). Colorless, odorless, liquid polyoxypropylenetriol was obtained in an amount of 391 g. Its hydroxyl number was 97.

EXAMPLE 91

A suspension was obtained in a similar manner as in Example 33 except that instead of the aqueous solution of potassium hydroxide, 2.2 ml (2.2 mmol) of a 1.0 M aqueous solution of barium hydroxide were used. The procedures of Example 33 were repeated in exactly the same manner except that the polymerization reaction time was changed to 24 hours. Colorless, odorless, liquid polyoxypropylenetriol was obtained in an amount of 181 g. Its hydroxyl number was 213.

EXAMPLE 92

In a 100-ml eggplant-type flask, weighed was 35.0 g (11.4 mmol) of polyoxypropylenetriol which had a hydroxyl number of 55 and had been industrially produced using glycerol and potassium hydroxide as initiators (product of Mitsui-Toatsu Chemicals Inc.). A 0.1 M hexane solution of di(n-butyl) magnesium (1.7 ml, 0.17 mmol) was added at room temperature. The resultant mixture was heated at 100° C. under stirring for 3 hours and was then allowed to cool down to room temperature. To the mixture, a solution of 264 mg (0.34 mmol) of tetrakis[tris(dimethylamino)phosphoranilideneamino]phosphonium chloride in 20 ml of THF was added to obtain a homogeneous solution. A polymerization reaction was conducted in exactly the same manner as the polymerization reaction of Example 33 except that the above-prepared solution was used instead of the suspension used in Example 33 and that the polymerization reaction time was changed to 24 hours. Colorless, odorless, liquid polyoxypropylenetriol was obtained in an amount of 48 g. Its hydroxyl number was 42.

EXAMPLE 93

Potassium methoxide (0.42 g, 6.0 mmol) was weighed in a 50-ml eggplant-type flask, followed by the addition of 20 ml of acetonitrile to form a homogeneous solution. To the solution, 4.65 (6.0 mmol) of tetrakis[tris(dimethylamino)phosphoranilideneamino]phosphonium chloride were added and the resultant mixture was stirred for 2 hours. After the reaction mixture was concentrated under reduced pressure to dryness, 20 ml of THF were added. Undissolved KCl was filtered off under a nitrogen gas atmosphere, and the filtrate was concentrated to dryness under reduced pressure, whereby the tetrakis[tris(dimethylamino)phosphoranilideneamino]phosphonium salt of methanol was synthesized.

A polymerization reaction was conducted in exactly the same manner as the polymerization reaction of Example 31 except that 3.85 g (5.0 mmol) of the phosphazenium salt of methanol synthesized by the above-described procedures, were used in place of the mono{tetrakis[tris(dimethylamino)phosphoranilideneamino]phosphonium} salt of glycerol, that fresh glycerol was not used and that the reaction time was changed to 20 hours. Colorless, odorless, liquid polyoxypropylenemonool of high viscosity was obtained in an amount of 177 g. Its hydroxyl number was 1.9. A polymer of high molecular weight was obtained.

EXAMPLE 94

A polymerization reaction was conducted in exactly the same manner as the polymerization reaction of Example 31 except that instead of the mono{tetrakis[tris(dimethylamino)phosphoranilideneamino]phosphonium} salt of glycerol, 4.12 g (5.0 mmol) of the phosphazenium salt of piperazine, said salt having had been synthesized in Example 17, namely, the tetrakis[tris(dimethylamino)phosphoranilideneamino]phosphonium salt of piperazine were used. Colorless, odorless polyoxypropylenetriol was obtained in an amount of 261 g. Its hydroxyl number was 145.

EXAMPLE 95

In an autoclave having an actual capacity of 600 ml and equipped with a temperature measuring tube, a pressure gauge, a stirrer and an alkylene oxide inlet tube, charged were 3.78 g (5.0 mmol) of a phosphazenium compound synthesized in a similar manner as in Example 24, namely, tetrakis[tris(dimethylamino)phosphoranilideneamino] phosphonium hydroxide $\{[(Me_2N)_3P=N]_4P^+OH^-\}$ and 20.0 g (217.4 mmol) of glycerol. After that, the autoclave was purged with dry nitrogen gas and its contents were heated to 80° C. While intermittently feeding propylene oxide so that the pressure during the reaction remained around 3.0 kg/cm$^2$, the contents were reacted at 80° C. for 6 hours. After the contents was maintained under 10 mmHg for 30 minutes, the pressure was allowed to return to normal pressure with nitrogen gas and the contents were allowed to cool down to room temperature. Colorless, odorless, liquid polyoxypropylenetriol was obtained in an amount of 264 g. Its hydroxyl number 142.

COMPARATIVE EXAMPLE 5

A polymerization reaction was conducted in exactly the same manner as the polymerization reaction of Example 95 except that tetrakis[tris(dimethylamino) phosphoranilideneamino]phosphonium hydroxide was not used. Propylene oxide was not consumed at all and the weight of the contents of the autoclave was 20.1 g. This weight was substantially the same as the weight of the glycerol itself charged in the autoclave, and no polyoxypropylenetriol was obtained.

EXAMPLE 96

Tetrakis[tris(dimethylamino)phosphoranilideneamino] phosphonium hydroxide (3.78 g, 5.0 mmol) was weighed in a 100-ml eggplant-type flask, to which 20.0 g (217.4 mmol) of glycerol were added. The resultant mixture was heated under stirring into a homogeneous mixture. Dry nitrogen gas was then bubbled at 100° C. and 5 mmHg to remove byproduced water, whereby a mixture of excess glycerol and the phosphazenium salt of glycerol contained therein, namely, the mono{tetrakis[tris(dimethylamino) phosphoranilideneamino]phosphonium salt of glycerol $\{[(Me_2N)_3P=N]_4P^+Gly^-\}$ was obtained.

In an autoclave similar to that employed in Example 95, the mixture obtained by the above-described procedures was charged in its entirety. The autoclave was purged with dry nitrogen gas and its contents were heated to 80° C. While intermittently feeding propylene oxide so that the pressure during the reaction remained around 3.0 kg/cm$^2$, the contents were reacted at 80° C. for 6 hours. After the contents were maintained under 10 mmHg for 30 minutes, the pressure was allowed to rise back to normal pressure with nitrogen gas and the contents were allowed to cooled down to room temperature. Colorless, odorless polyoxypropylenetriol was obtained in an amount of 289 g. Its hydroxyl number was 129.

EXAMPLE 97

A polymerization reaction was conducted in exactly the same manner as the polymerization reaction of Example 95 except that 3.85 (5.0 mmol) of tetrakis[tris(dimethylamino) phosphoranilideneamino]phosphonium methoxide $\{[(Me_2N)_3P=N]_4P^+CH_3O^-\}$, a phosphazenium compound synthesized in a similar manner as in Example 1, were used instead of tetrakis[tris(dimethylamino) phosphoranilideneamino]phosphonium hydroxide and that the polymerization reaction temperature was changed to 100° C. Colorless, odorless polyoxypropylenetriol was obtained in an amount of 324 g. Its hydroxyl number was 116.

EXAMPLE 98

Tetrakis[tris(dimethylamino)phosphoranilideneamino] phosphonium methoxide (2.01 g, 2.6 mmol) was weighed in a 100-ml eggplant-type flask, to which 20.0 g (217.4 mmol) of glycerol were added. The resultant mixture was heated under stirring into a homogeneous mixture. Dry nitrogen gas was then bubbled at 100° C. and 5 mmHg to remove by-produced methanol, whereby a mixture of excess glycerol and the phosphazenium salt of glycerol contained therein, namely, the mono{tetrakis[tris(dimethylamino) phosphoranilideneamino]phosphonium} salt of glycerol was obtained.

In an autoclave similar to that employed in Example 95, the mixture obtained by the above-described procedures was charged in its entirety. The autoclave was purged with dry nitrogen gas and its contents were heated to 100° C. While intermittently feeding propylene oxide so that the pressure during the reaction remained around 3.0 kg/cm$^2$, the contents were reacted at 100° C. for 6 hours. After the contents were maintained under 10 mmHg for 30 minutes, the pressure was allowed to rise back to normal pressure with nitrogen gas and the contents were allowed to cool down to room temperature. Colorless, odorless polyoxypropylenetriol was obtained in an amount of 267 g. Its hydroxyl number was 138.

EXAMPLE 99

A polymerization reaction was conducted in exactly the same manner as the polymerization reaction of Example 95 except that 5.63 g (5.0 mmol) of tetrakis[tri(pyrrolidine-1-yl)phosphoranilideneamino]phosphonium tert-butoxide $\{[Py_3P=N]_4P^+tert-C_4H_9O^-\}$, a phosphazenium compound synthesized in a similar manner as in Example 3, was used instead of tetrakis[tris(dimethylamino) phosphoranilideneamino]phosphonium hydroxide. Colorless, odorless polyoxypropylenetriol was obtained in an amount of 281 g. Its hydroxyl number was 133.

EXAMPLE 100

Tetrakis[tris(dimethylamino)phosphoranilideneamino] phosphonium hydroxide (9.08 g, 12 mmol) was weighed in a 300-ml eggplant-type flask, to which 92.0 g (1.0 mol) of glycerol were added. The resultant mixture was heated under stirring into a homogeneous mixture. Dry nitrogen gas was then bubbled at 100° C. and 5 mmHg to remove byproduced water, whereby a mixture of excess glycerol and the phosphazenium salt of glycerol contained therein, namely, the mono{tetrakis[tris(dimethylamino) phosphoranilideneamino]phosphonium} salt of glycerol was obtained.

In an autoclave similar to that employed in Example 95, 21.92 g of the mixture obtained by the above-described procedures were charged. The autoclave was purged with dry nitrogen gas and its contents were heated to 100° C. While intermittently feeding styrene oxide so that the pressure during the reaction remained around 1.5 kg/cm$^2$, the contents were reacted at 100° C. for 6 hours. After the contents were maintained under 5 mmHg for 2 hours, the pressure was allowed to rise back to normal pressure with nitrogen gas and the contents were allowed to cool down to room temperature. Colorless, odorless polyoxystyrenetriol was obtained in an amount of 374 g. Its hydroxyl number was 99.

EXAMPLE 101

By reacting dimethylaminotris[tris(dimethylamino) phosphoranilideneamino]phosphonium tetrafluoroborate $\{[Me_2N)_3P=N]_3(Me_2N)P^+BF_4^-\}$ and potassium tert-butoxide, dimethylaminotris[tris(dimethylamino) phosphoranilideneamino]phosphonium tert-butoxide $\{[Me_2N)_3P=N]_3(Me_2N)P^+tert-C_4H_9O^-\}$ was obtained as a phosphazenium compound. In a 100-ml eggplant-type flask, 163 mg (0.24 mmol) of the above phosphazenium compound were weighed, followed by the addition of 20.0 g (20.0 mmol) of polyoxypropylenetriol which had a hydroxyl number of 168 and had been industrially produced using glycerol and potassium hydroxide as initiators (product of Mitsui-Toatsu Chemicals Inc.). The resultant mixture was heated under stirring into a homogeneous mixture. Dry nitrogen gas was then bubbled at 100° C. and 5 mmHg to remove by-produced t-butanol, whereby a mixture of excess polyoxypropylenetriol and the phosphazenium salt of polyoxypropylenetriol contained therein, namely, the mono{dimethylaminotris[tris(dimethylamino) phosphoranilideneamino]phosphonium} salt of polyoxypropylenetriol was obtained.

In an autoclave similar to that employed in Example 95, the mixture obtained by the above-described procedures was charged in its entirety. The autoclave was purged with dry nitrogen gas and its contents were heated to 100° C. While intermittently feeding propylene oxide so that the pressure during the reaction remained around 3.0 kg/cm², the contents were reacted at 100° C. for 6 hours. After the contents were maintained under 10 mmHg for 30 minutes, the pressure was allowed to rise back to normal pressure with nitrogen gas and the contents were allowed to cool down to room temperature. Colorless, odorless polyoxypropylenetriol was obtained in an amount of 204 g. Its hydroxyl number was 18.

EXAMPLE 102

In an autoclave similar to that employed in Example 95, 21.92 g of the mixture of glycerol and the phosphazenium compound of glycerol, said mixture having had been obtained in Example 100, were charged. While intermittently feeding propylene oxide and ethylene oxide so that their molar ratio became 7 to 3 and the pressure during the reaction remained around 3.0 kg/cm², the contents were reacted at 80° C. for 6 hours. After the contents were maintained under 10 mmHg for 30 minutes, the pressure was allowed to rise back to normal pressure with nitrogen gas and the contents were allowed to cool down to room temperature. Colorless, odorless polyoxyethylenepolyoxypropylenetriol was obtained as a random copolymer in an amount of 267 g. Its hydroxyl number was 139.

EXAMPLE 103

A polymerization reaction was conducted in exactly the same manner as the polymerization reaction of Example 95 except that 4.16 g (5.0 mmol) of tetrakis[tris (dimethylamino)phosphoranilideneamino]phosphonium phenoxide $\{(Me_2N)_3P=N]_4P^+C_6H_5O^-\}$, a phosphazenium compound synthesized in a similar manner as in Example 4, were used instead of tetrakis[tris(dimethylamino) phosphoranilideneamino]phosphonium hydroxide, that instead of glycerol, ethylene glycol was used in the same amount (217.4 mmol, 13.5 g) and that the polymerization reaction temperature was changed to 100° C. Colorless, odorless polyoxypropylenediol was obtained in an amount of 342 g. Its hydroxyl number was 72.

EXAMPLE 104

A polymerization reaction was conducted in exactly the same manner as the polymerization reaction of Example 95 except that 4.16 (5.0 mmol) of the phosphazenium compound synthesized in Example 103 were used instead of tetrakis[tris(dimethylamino)phosphoranilideneamino] phosphonium hydroxide, that instead of glycerol, propylene glycol was used in the same amount (217.4 mmol, 18.3 g) and that the polymerization reaction temperature was changed to 100° C. Colorless, odorless polyoxypropylenediol was obtained in an amount of 332 g. Its hydroxyl number was 74.

EXAMPLE 105

By reacting tetrakis[tris(dimethylamino) phosphoranilideneamino]phosphonium chloride and sodium 4-methylphenoxide, tetrakis[tris(dimethylamino) phosphoranilideneamino]phosphonium 4-methylphenoxide $\{[Me_2N)_3-P=N]_4P^+4-CH_3C_6H_4O^-\}$ was synthesized as a phosphazenium compound.

In an autoclave similar to that employed in Example 95, 4.23 g (5.0 mmol) of the above phosphazenium compound and 19.6 g (217.4 mmol) of 1,4-butanediol were charged. The autoclave was then purged with dry nitrogen gas and the contents were heated to 110° C. While intermittently feeding 1,2-butylene oxide so that the pressure during the reaction remained around 2.5 kg/cm², the contents were reacted at 110° C. for 6 hours. After the contents were maintained under 10 mmHg for 30 minutes, the pressure was allowed to rise back to normal pressure with nitrogen gas and the contents were allowed to cool down to room temperature. Colorless, odorless polyoxy-1,2-butylenediol was obtained in an amount of 389 g. Its hydroxyl number was 65.

EXAMPLE 106

A polymerization reaction was conducted in exactly the same manner as the polymerization reaction of Example 95 except that 3.99 g (5.0 mmol) of tetrakis[tris (dimethylamino)phosphoranilideneamino]phosphonium acetate $\{(Me_2N)_3P=N]_4P^+CH_3COO^-\}$, a phosphazenium compound synthesized in a similar manner as in Example 5, were used instead of tetrakis[tris(dimethylamino) phosphoranilideneamino]phosphonium hydroxide, that instead of glycerol, pentaerythritol was used in the same amount (217.4 mmol, 29.6 g) and that the polymerization reaction temperature was changed to 100° C. Colorless, odorless polyoxypropylenetetraol was obtained in an amount of 324 g. Its hydroxyl number was 153.

EXAMPLE 107

By reacting tetrakis[tris(dimethylamino) phosphoranilideneamino]phosphonium chloride and sodium propionate, tetrakis[tris(dimethylamino) phosphoranilideneamino]phosphonium propionate $\{[Me_2N)_3-P=N]_4P^+C_2H_5COO^-\}$ was synthesized as a phosphazenium compound.

A polymerization reaction was conducted in exactly the same manner as the polymerization reaction of Example 95 except that 4.06 (5.0 mmol) of the above phosphazenium compound were used instead of tetrakis[tris(dimethylamino)

phosphoranilideneamino]phosphonium hydroxide, that instead of glycerol, glucose was used in the same amount (217.4 mmol, 39.1 g) and that the polymerization reaction temperature was changed to 100° C. Colorless, odorless polyoxypropylenepentaol was obtained in an amount of 298 g. Its hydroxyl number was 237.

EXAMPLE 108

By reacting bis[tris(diethylamino) phosphoranilideneamino]bis(diethylamino)phosphonium tetrafluoroborate $\{[(Et_2N)_3P=N]_2(Et_2N)_2P^+BF_4^-\}$ and sodium phenoxide, bis[tris(diethylamino) phosphoranilideneamino]bis(diethylamino]phosphonium phenoxide $\{[Et_2N)_3-P=N]_2(Et_2N)_2P^+C_6H_5O^-\}$ was synthesized as a phosphazenium compound.

In an autoclave similar to that employed in Example 95, 3.76 g (17.4 mmol) of the above phosphazenium compound and 13.0 g (217.4 mmol) of ethylenediamine were charged. The autoclave was then purged with dry nitrogen gas and the contents were heated to 100° C. While intermittently feeding propylene oxide so that the pressure during the reaction. the pressure during the reaction remained around 3.0 kg/cm², the contents were reacted at 100° C. for 6 hours. After the contents were maintained under 10 mmHg for 30 minutes, the pressure was allowed to rise back to normal pressure with nitrogen gas and the contents were allowed to cool down to room temperature. Slightly brownish, odorless polyoxypropylenetetraol was obtained in an amount of 219 g. Its hydroxyl number was 240.

EXAMPLE 109

Procedures of Example 108 were repeated likewise except that 3.78 g (5.0 mmol) of tetrakis[tris(dimethylamino) phosphoranilideneamino]phosphonium hydroxide were used instead of bis[tris(diethylamino) phosphoranilideneamino]bis(diethylamino)phosphonium phenoxide and that instead of ethylenediamine, N,N'-dimethylethylenediamine was used in the same amount (217.4 mmol, 19.1 g). Slightly brownish, odorless polyoxypropylenediol was obtained in an amount of 318 g. Its hydroxyl number was 78.

EXAMPLE 110

Procedures of Example 108 were repeated likewise except that 3.78 g (5.0 mmol) of tetrakis[tris(dimethylamino) phosphoranilideneamino]phosphonium hydroxide were used instead of bis[tris(diethylamino) phosphoranilideneamino]bis(diethylamino)phosphonium phenoxide and that instead of ethylenediamine, piperazine was used in the same amount (217.4 mmol, 18.7 g). Colorless, odorless polyoxypropylenediol was obtained in an amount of 307 g. Its hydroxyl number was 81.

EXAMPLE 111

Procedures of Example 108 were repeated likewise except that 3.78 g (5.0 mmol) of tetrakis[tris(dimethylamino) phosphoranilideneamino]phosphonium hydroxide were used instead of bis[tris(diethylamino) phosphoranilideneamino]bis(diethylamino)phosphonium phenoxide and that instead of ethylenediamine, piperidine was used in the same amount (217.4 mmol, 18.5 g). Colorless, odorless polyoxypropylenemonool was obtained in an amount of 342 g. Its hydroxyl number was 36.

EXAMPLE 112

In an autoclave having an actual capacity of 600 ml and equipped with a temperature measuring tube, a pressure gauge, a stirrer and an alkylene oxide inlet tube, charged was 3.78 g (5.0 mmol) of tetrakis[tris(dimethylamino) phosphoranilideneamino]phosphonium hydroxide $\{[Me_2N)_3P=N]_4P^+OH^-\}$, a phosphazenium compound, and 20.0 g (217.4 mmol) of glycerol. After that, the reactor was purged with dry nitrogen gas and its contents were heated to 80° C. While intermittently feeding 400 g (6.90 mol) of propylene oxide as a first alkylenoxide so that pressure during the reaction remained around 3.0 kg/cm², the contents were reacted at 80° C. for 12 hours (first step). After the contents were maintained under 10 mmHg for 30 minutes, the pressure was allowed to rise back to normal pressure with dry nitrogen gas and the contents were allowed to cool down to room temperature. To further increase the molecular weight of the resultant polyoxypropylenetriol, the contents were transferred into an autoclave having an actual capacity of 2,300 ml and equipped with a temperature measuring tube, a pressure gauge, a stirrer and an alkylene oxide inlet tube. The reactor was purged with dry nitrogen gas and its contents were heated to 80° C. While intermittently feeding 930 g (16.03 mmol) of propylene oxide so that the pressure during the reaction remained around 3.0 kg/cm², the contents were reacted at 80° C. for 24 hours (second step). The contents were then maintained under 10 mmHg for 30 minutes. After that, the internal pressure of the reactor was allowed to rise back to normal pressure with dry nitrogen gas. By the 2-step reaction described above, polyoxypropylenetriol was obtained as a polymer of the first alkylene oxide compound. The contents were heated to 100° C., and were then reacted with 200 g (4.55 mol) of ethylene oxide as a second alkylene oxide at 100° C. for 12 hours while intermittently feeding the ethylene oxide so that the pressure during the reaction remained around 4.0 kg/cm². A colorless, odorless block copolymer was obtained in an amount of 1,504 g. Its hydroxyl number was 24. This block copolymer is polyoxypropylenepolyoxyethylenetriol, which has blocks in the order of poly(propylene oxide)-poly(ethylene oxide), and contains poly(propylene oxide) blocks and polyethylene oxide blocks at a ratio of about 5:1 (molar ratio; this will hereinafter apply equally).

COMPARATIVE EXAMPLE 6

A polymerization reaction was conducted in exactly the same manner as the polymerization reaction in the first step of Example 112 except that tetrakis[tris(dimethylamino) phosphoranilideneamino]phosphonium hydroxide was not used. Propylene oxide was not consumed at all. The weight of the contents of the reactor was 20.1 g, which was substantially equal to the weight of the glycerol itself charged in the reactor. No polyoxypropylenetriol was obtained.

EXAMPLE 113–116

In each example, a polymer of a first alkylene oxide was obtained in two steps as in Example 112 except that the phosphazenium compound and active hydrogen compound shown in Table 12 were used in the same molar amounts, respectively, that the first alkylene oxide shown in Table 12 was used and that the temperature conditions shown in Table 12 were employed. Further, polymerization of ethylene oxide as a second alkylene oxide compound was conducted in a similar manner as in Example 112. The results are presented together with the results of Example 112 in Table 12. The phosphazenium compound employed in each example had been synthesized by reacting the corresponding phosphazenium chloride with potassium methoxide, potassium ethoxide, potassium acetate or sodium phenoxide.

TABLE 12

| Ex. | Phosphazenium compound | Active hydrogen compound | First alkylene oxide compound | Polymerization temperature of first alkylene oxide compound (° C.) | Yield(g) | Hydroxyl number of copolymer |
|---|---|---|---|---|---|---|
| 112 | [(Me$_2$N)$_3$P=N]$_4$P$^+$OH$^-$ | Glycerol | Propylene oxide | 80 | 1504 | 24 |
| 113 | [(Me$_2$N)$_3$P=N]$_3$(Me$_2$N)P$^+$MeO$^-$ | Ethylene glycol | Propylene oxide | 80 | 1386 | 18 |
| 114 | [(Me$_2$N)$_3$P=N]$_2$(Me$_2$N)$_2$P$^+$EtO$^-$ | Propylene glycol | Propylene oxide | 110 | 910 | 29 |
| 115 | [(Me$_2$N)$_3$P=N]$_4$P$^+$CH$_3$COO$^-$ | Glucose | Butylene oxide | 80 | 1320 | 52 |
| 116 | [(Me$_2$N)$_3$P=N]$_3$(Me$_2$N)P$^+$C$_6$H$_5$O$^-$ | Pentaerythritol | Styrene oxide | 80 | 1222 | 40 |

Note: In the table, "Me" and "Et" represent a methyl group and an ethyl group, respectively.

EXAMPLE 117

Tetrakis[tris(dimethylamino)phosphoranilideneamino] phosphonium hydroxide (3.78 g, 5.0 mmol) was weighed in a 100-ml eggplant-type flask, to which 20.0 g (217.4 mmol) of glycerol were added. The resultant mixture was heated under stirring into a homogeneous mixture. Dry nitrogen gas was then bubbled at 100° C. and 5 mmHg to remove byproduced water, whereby a mixture of excess glycerol and the phosphazenium salt of glycerol contained therein, namely, the mono{tetrakis[tris(dimethylamino) phosphoranilideneamino]-phosphonium} salt of glycerol {[Me$_2$N)$_3$P=N]$_4$P$^+$Gly$^-$ (Gly$^-$ represents an anion formed by deprotonizing one of the hydroxyl groups of glycerol; this will hereinafter apply equally) was obtained.

The procedures of Example 112 were repeated in exactly the same manner except that the above-obtained mixture was charged in its entirety instead of the phosphazenium compound and glycerol employed in the polymerization reaction. A colorless, odorless block copolymer was obtained in an amount of 1,532 g. Its hydroxyl number was 24. This block copolymer is polyoxypropylenepolyoxyethylenetriol, which has blocks in the order of poly(propylene oxide)-poly(ethylene oxide), and contains poly(propylene oxide) blocks and poly (ethylene oxide) blocks at a ratio of about 5:1.

EXAMPLE 118

In exactly the same manner as in Example 2, dimethylaminotris[tris(dimethylamino) phosphoranilideneamino]phosphonium methoxide {[(Me$_2$N)$_3$P=N]$_3$(Me$_2$N)P$^+$CH$_3$O$^-$} was obtained.

In a 200-ml eggplant-type flask, weighed was 0.59 g (0.92 mmol) of the phosphazenium compound obtained by the above-described procedures. Added to this phosphazenium compound were 40.0 g (40 mmol) of polyoxypropylenetriol which had a hydroxyl number of 168 and had been industrially produced using glycerol and potassium hydroxide as initiators (product of Mitsui-Toatsu Chemicals Inc.). The resultant mixture was heated under stirring into a homogeneous mixture. Dry nitrogen gas was then bubbled at 100° C. and 5 mmHg to remove by-produced methanol, whereby a mixture of excess polyoxypropylenetriol and the phosphazenium salt of polyoxypropylenetriol contained therein, namely, the mono{dimethylaminotris[tris(dimethylamino) phosphoranilideneamino]phosphonium} salt of polyoxypropylenetriol was obtained.

In a 600-ml autoclave similar to that employed in Example 112, the mixture obtained by the above-described procedures was charged in its entirety. The autoclave was purged with dry nitrogen gas and its contents were heated to 100° C. While intermittently feeding 400 g (6.90 mol) of propylene oxide so that the pressure during the reaction remained around 3.0 kg/cm$^2$, the contents were reacted at 100° C. for 12 hours. After the contents were maintained under 10 mmHg for 30 minutes, the pressure was allowed to rise back to normal pressure with nitrogen gas. While intermittently feeding 130 g (2.95 mol) of ethylene oxide as a second alkylene oxide compound so that the pressure during the reaction remained around 4.0 kg/cm$^2$, the contents were reacted at 100° C. for 6 hours. A colorless, odorless block copolymer was obtained in an amount of 551 g. Its hydroxyl number was 14. This block copolymer is polyoxypropylenepolyloxyethylenetriol, which has blocks in the order of poly(propylene oxide)-poly(ethylene oxide), and contains poly(propylene oxide) blocks and poly (ethylene oxide) blocks at a ratio of about 2.5:1.

EXAMPLE 119

Glycerol (20.0 g, 217.4 mmol) was weighed in a 100-ml eggplant-type flask, to which 5.0 ml (5.0 mmol) of a 1.0 N aqueous solution of potassium hydroxide were added to form a homogeneous solution. Dry nitrogen gas was then bubbled at 110° C. under reduced pressure to remove water, whereby the monopotassium salt of glycerol was prepared in a form contained in excess glycerol. To the salt, a solution of 3.87 g (5.0 mmol) of tetrakis[tris(dimethylamino) phosphoranilideneamino]-phosphonium chloride in 20 ml of THF (tetrahydrofuran; this will hereinafter apply equally) was added, followed by stirring to obtain a suspension.

In a 600-ml autoclave similar to that employed in Example 112, the suspension obtained by the above-described procedures was charged. The suspension was heated with stirring under reduced pressure so that the THF was distilled off. After that, the reactor was purged with dry nitrogen gas and its contents were heated to 80° C. While intermittently feeding 400 g (6.90 mol) of propylene oxide as a first alkylenoxide so that the pressure during the reaction remained around 3.0 kg/cm$^2$, the contents were reacted at 80° C. for 12 hours. After the contents were maintained under 10 mmHg for 30 minutes, the pressure was allowed to rise back to normal pressure with dry nitrogen gas and the contents were allowed to cool down to room temperature. The resulting polyoxypropylenetriol including the catalysts was charged in its entirely in a 2,300-ml autoclave similar to that employed in Example 112. The reactor was then purged with dry nitrogen gas and its contents were heated to 100° C. While intermittently feeding 200 g (4.55 mol) of ethylene oxide as a second alkylene oxide compound so that the pressure during the reaction remained around 4.0 kg/cm$^2$, the contents were reacted at 100° C. for 12 hours. A colorless, odorless block copolymer was obtained in an amount of 549 g. Its hydroxyl number was 68. This block copolymer is polyoxypropylenepolyoxyethylenetriol, which has blocks in the order of poly(propylene oxide)-poly (ethylene oxide), and contains poly(propylene oxide) blocks and poly(ethylene oxide) blocks at a ratio of about 1.5:1.

COMPARATIVE EXAMPLE 7

In a similar manner as the former stage of Example 119, the monopotassium salt of glycerol was prepared in a form contained in excess glycerol. Without addition of tetrakis [tris(dimethylamino)phosphoranilideneamino]phosphonium chloride to the salt, 20 ml of THF were added so that a suspension was obtained. Using this suspension, polymerization of propylene oxide was conducted as in Example 119. The reaction was extremely slow and propylene oxide was consumed only slightly. The weight of the contents of the autoclave was 25 g, which was only slightly greater than the weight of the charged glycerol itself.

EXAMPLE 120–123

In each example, the procedures of Example 119 were repeated likewise except that the phosphazenium compound and basic metal compound shown in Table 13 were used in the same moles, respectively, that the first and second alkylene oxide compounds shown in Table 13 were used in the same weights, respectively, and that the polymerization temperature conditions for the first alkylene oxide compound, said conditions being shown in Table 12, were employed. The results are presented together with the results of Example 121 in Table 13. The phosphazenium compounds employed in Example 121 and Example 122 had been synthesized by reacting the corresponding phosphazenium chlorides with sodium tetrafluoroborate and sodium perchlorate, respectively, and the phosphazenium compound employed in Example 123 had been synthesized by a reaction between 1-tert-butyl-4,4,6,6,6-penta(pyrrolidin-1-yl)-2,2-bis[tri(pyrrolidin-1-yl)phosphoranilideneamino]-$2\lambda^5$, $4\lambda^5$, $6\lambda^5$-catenatri(phosphazene) and hydrochloric acid.

A polymerization reaction was conducted in a similar manner as the polymerization reaction of Example 119 except for the use of the homogeneous solution obtained by the above-described procedures, ethylene oxide and styrene oxide in place of the suspension, propylene oxide and ethylene oxide, respectively. A colorless, odorless block copolymer was obtained in an amount of 492 g. Its hydroxyl number was 100. This block copolymer is polyoxyethylenepolyoxystyrenediol, which has blocks in the order of poly(ethylene oxide)-poly(styrene oxide), and contains poly(ethylene oxide) blocks and poly(styrene oxide) blocks at a ratio of about 12.5:1.

EXAMPLE 125

By reacting 1-(1,1,3,3-tetramethylbutyl)-2-dimethylamino-2-tris(dimethylamino)phosphoranilideneamino-4,4,4-tris(diethylamino)-$2\lambda^5$, $4\lambda^5$-catenadi-(phosphazene) $\{[(Me_2N)_3P=N]_2(Me_2N)_2P=N$-tert-$C_8H_{17}\}$ and ⅓ equivalent of phosphoric acid, tris{1,1,3,3-tetramethylbutylaminodimethylamino-bis[tris(dimethylamino)phosphoranilideneamino]phosphonium phosphate $\{\{[(Me_2N)_3P=N]_2(Me_2N)(tert-C_8H_{17}NH)P^+\}_3PO_4^{3-}\}$ was synthesized as a phosphazenium compound.

Weighed in a 200-ml eggplant-type flask were 40.0 g (40.0 mmol) of polyoxyethylenediol, which had a hydroxyl number of 112 and had been produced using ethylene glycol and cesium hydroxide as initiators. THF (40 ml) was added to obtain a homogeneous solution. After addition of 4.60 ml (0.46 mmol) of a 0.10 M (mol/l) hexane solution of di(n-butyl) magnesium to the homogeneous solution at room temperature, the resultant mixture was heated for 2 hours under reflux. The mixture was then allowed to cool down to room temperature, to which 0.49 g (0.31 mmol) of the phosphazenium compound obtained by the above-described procedures was added to obtain a suspension.

In a 600-ml autoclave similar to that employed in Example 112, the suspension obtained by the above-

TABLE 13

| Ex. | Phosphazenium compound | Basic metal compound | First alkylene oxide compound | Polymerization temperature of first alkylene oxide compound (° C.) | Second alkylene oxide compound | Yield (g) | Hydroxyl number of copolymer |
|---|---|---|---|---|---|---|---|
| 119 | [(Me$_2$N)$_3$P=N]$_4$P$^+$Cl$^-$ | KOH | Propylene oxide | 80 | Ethylene oxide | 549 | 66 |
| 120 | [(Me$_2$N)$_3$P=N]$_4$P$^+$Cl$^-$ | LiOH | Propylene oxide | 80 | Ethylene oxide | 547 | 68 |
| 121 | [(Me$_2$N)$_3$P=N]$_3$(Me$_2$N)P$^+$BF$_4^-$ | NaOH | Propylene oxide | 80 | Ethylene oxide | 583 | 63 |
| 122 | [(Me$_2$N)$_3$P=N]$_2$(Me$_2$N)$_2$P$^+$ClO$_4^-$ | KOH | Propylene oxide | 110 | Ethylene oxide | 358 | 103 |
| 123 | {Py[Py$_2$P=N]$_2$}(Py$_3$P=N)$_2$(t-BuNH)P$^+$Cl$^-$ | Ba(OH)$_2$ | Butylene oxide | 110 | Propylene oxide | 206 | 182 |

Note: In the table, "Me" and "Py" represent a methyl group and a pyrrolidin-1-yl, respectively.

EXAMPLE 124

N,N'-Dimethylethylenediamine (19.1 g, 217.4 mmol) was weighed in a 100-ml eggplant-type flask. Subsequent to dilution with 20 ml of THF, the resulant solution was cooled to −70° C., followed by the addition of 5.0 ml of a 1.0 M hexane solution of n-butyl lithium (5.0 mmol in terms of n-butyl lithium). After the thus-obtained mixture was stirred at the same temperature for 10 minutes, the temperature of the mixture was allowed to rise back to room temperature over about 30 minutes. The mixture was stirred further for 30 minutes, whereby the monolithium salt of N,N'-dimethylethyleneamine was obtained in a form contained in excess N,N'-dimethylethylenediamine. Added to the salt was a solution of 3.63 g (5.0 mmol) of 1,1,3,3-tetramethylbutylaminotris[tris(dimethylamino)phosphoranilideneamino]phosphonium chloride in 20 ml of THF. The resulting mixture was stirred for 2 hours, whereby a homogeneous solution was obtained.

described procedures was charged. The suspension was heated with stirring under reduced pressure so that the THF was distilled off. After that, the reactor was purged with dry nitrogen gas and its contents were heated to 80° C. While intermittently feeding 400 g (6.90 mol) of propylene oxide as a first alkylenoxide so that the pressure during the reaction remained around 3.0 kg/cm$^2$, the contents were reacted at 110° C. for 12 hours. After the contents were maintained under 10 mmHg for 30 minutes, the pressure was allowed to rise back to normal pressure with dry nitrogen gas and the contents were cooled down to 100° C. While intermittently feeding 100 g (2.27 mol) of ethylene oxide as a second alkylene oxide compound so that the pressure during the reaction remained around 4.0 kg/cm$^2$, the contents were reacted at 100° C. for 12 hours. A colorless, odorless block copolymer was obtained in an amount of 171 g. Its hydroxyl number was 71. This block copolymer is polyoxyethylenepolyoxypropylenepolyoxyethylenediol, which has blocks in the order of poly(ethylene oxide)-poly(propylene oxide)-poly(ethylene oxide), and contains poly(ethylene oxide) blocks and poly(propylene oxide) blocks at a ratio of about 1:1.

EXAMPLE 126

A suspension which had been obtained in exactly the same manner as in Example 119 was filtered to remove the byproduced salt. After the salt was washed with THF, the filtrate and the washing were combined together.

A polymerization reaction was conducted in exactly the same manner as the polymerization reaction of Example 119 except that the combined solution, which had been obtained by the above-described procedures, was used instead of the suspension. A colorless, odorless block copolymer was obtained in an amount of 584 g. Its hydroxyl number was 64. This block copolymer is polyoxypropylenepolyoxyethylenetriol, which has blocks in the order of poly(propylene oxide)-poly(ethylene oxide), and contains poly(propylene oxide) blocks and poly(ethylene oxide) blocks at a ratio of about 1.5:1.

EXAMPLE 127

Charged in a 2,300-ml autoclave similar to that employed in Example 112 were 215 g of polyoxypropylenepolyoxyethylenetriol, which had been obtained in Example 112 after polymerization of ethylene oxide as a second alkylene oxide compound and which still contained the catalysts. The reactor was purged with dry nitrogen gas and its contents were heated to 90° C. While intermittently feeding 195 g (3.36 mol) of propylene oxide so that the pressure during the reaction remained around 3.0 kg/cm$^2$, the contents were reacted at 80° C. for 12 hours. After the contents were maintained under 10 mmHg for 30 minutes, the pressure was allowed to rise back to normal pressure with dry nitrogen gas and the contents were allowed to cool down to room temperature. A colorless, odorless block copolymer was obtained in an amount of 405 g. Its hydroxyl number was 15. This block copolymer is polyoxypropylenepolyoxyethylenepolyoxypropylenetriol, which has blocks in the order of polypropylene oxide-poly(ethylene oxide)-poly(propylene oxide), and contains poly(propylene oxide) blocks and poly(ethylene oxide) blocks at a ratio of about 10:1.

EXAMPLE 128

Charged in the 2,300-ml autoclave employed in Example 112 were 212 g of polyoxypropylenepolyoxyethylenepolyoxypropylenetriol, which had been obtained in Example 127 and which still contained the catalysts. The reactor was purged with dry nitrogen gas and its contents were heated to 100° C. While intermittently feeding 125 g (2.84 mol) of ethylene oxide so that the pressure during the reaction remained around 4.0 kg/cm$^2$, the contents were reacted at 100° C. for 24 hours. After the contents were maintained under 10 mmHg for 30 minutes, the pressure was allowed to rise back to normal pressure with dry nitrogen gas and the contents were allowed to cool down to room temperature. A colorless, odorless block copolymer was obtained in an amount of 328 g. Its hydroxyl number was 10. This block copolymer is polyoxypropylenepolyoxyethylenepolyoxypropylenepolyoxyethylenetriol, which has blocks in the order of poly(propylene oxide)-poly(ethylene oxide)-poly(propylene oxide)-poly(ethylene oxide), and contains poly(propylene oxide) blocks and poly(ethylene oxide) blocks at a ratio of about 1:1.

According to the present invention, the phosphazenium salts of the active hydrogen compounds, said salts being represented by the chemical formula (1), or the phosphazenium hydroxides represented by the chemical formula (2) do not contain any metal component and can provide cations of various sizes. They have high solubility in organic solvents and the anions of the active hydrogen compounds are provided with its essential reactivity. They are hence extremely useful, for example, as reaction reagents for organic reactions.

Further, according to the process of the present invention, poly(alkylene oxide)s free of remaining odor can be readily, conveniently and efficiently produced without using any unusual metal component. Compared with phosphazene bases which require utmost care for their high reactivity with moisture in air or the like, the phosphazenium compounds and other compounds which are usable in the process of the present invention are more stable and are hence more advantageous in handling.

We claim:

1. A phosphazenium salt of an active hydrogen compound, represented by the following chemical formula (1):

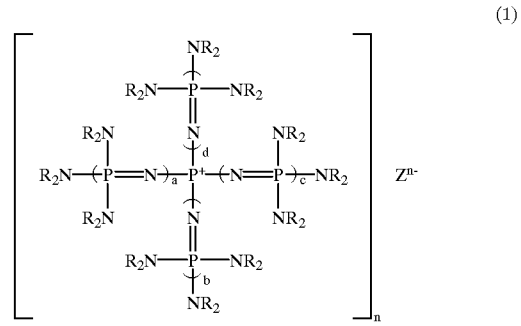

wherein:

n stands for an integer of from 1 to 8 and represents the number of phosphazenium cations, and $Z^{n-}$ represents an n-valent anion of an active hydrogen compound in a form derived by elimination of n protons from an active hydrogen compound having at most eight active hydrogen atoms on oxygen atoms or nitrogen atoms, said active hydrogen compound being selected from the group consisting of water, aliphatic or alicyclic alcohols having 1 to 20 carbons atoms, polyhydric aliphatic or alicyclic alcohols having 2 to 20 carbon atoms and 2 to 8 hydroxyl groups, saccharides and derivatives thereof, poly(alkylene oxides) having 2 to 8 terminals, 1 to 8 hydroxyl groups at said terminals and a molecular weight of from 100 to 50,000, polyamines having 2 to 20 carbon atoms and 2 to 3 primary or secondary amino groups, saturated cyclic secondary amines having 4 to 20 carbon atoms, and cyclic polyamines having 4 to 20 carbon atoms and 2 to 3 secondary amino groups, a, b, c and d each stands for a positive integer of 3 or smaller or 0 with the proviso that they are not all 0 at the same time, Rs represent the same or different hydrocarbon groups having 1 to 10 carbon atoms, and two Rs on each common nitrogen atom may be coupled together to form a ring structure.

2. The salt according to claim 1, wherein n is an integer of from 1 to 3.

3. The salt according to claim 1, wherein a, b, c and d are not all 0 at the same time and each stands for a positive integer of 2 or smaller or 0.

4. The salt according to claim 1, wherein Rs are the same or different and are aliphatic hydrocarbon groups having 1 to 10 carbon atoms.

5. The salt according to claim 1, wherein two Rs on each common nitrogen atom are coupled together to form a ring structure and the resultant divalent substituent on said nitrogen atom is a tetramethylene or pentamethylene group.

6. A phosphazenium hydroxide represented by the following chemical formula (2):

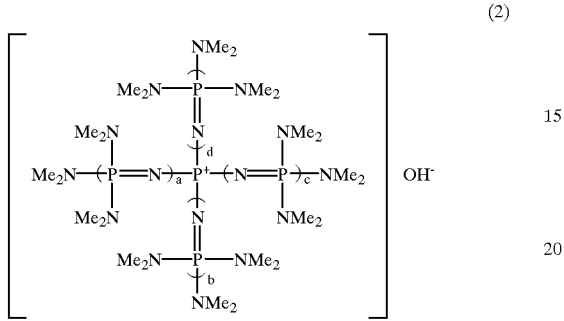

(2)

wherein each Me represents a methyl group, and a, b, c and d are each 0 or 1 with the proviso that they are not all 0 at the same time.

7. A process for the preparation of a phosphazenium salt of an active hydrogen compound, represented by the following chemical formula (1):

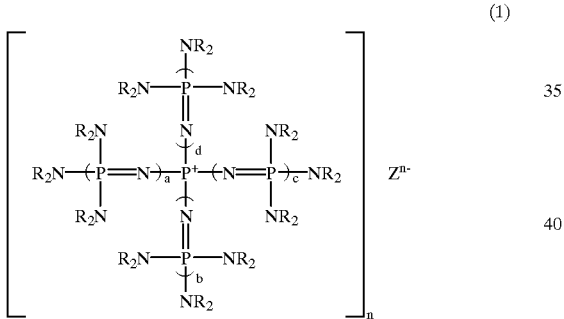

(1)

wherein:
   n stands for an integer of from 1 to 8 and represents the number of phosphazenium cations, and
   $Z^{n-}$ represents an n-valent anion of an active hydrogen compound in a form derived by elimination of n protons from an active hydrogen compound having at most eight active hydrogen atoms on oxygen atoms or nitrogen atoms, said active hydrogen compound being selected from the group consisting of water, aliphatic or alicyclic alcohols having 1 to 20 carbons atoms, polyhydric aliphatic or alicyclic alcohols having 2 to 20 carbon atoms and 2 to 8 hydroxyl groups, saccharides and derivatives thereof, poly(alkylene oxides) having 2 to 8 terminals, 1 to 8 hydroxyl groups at said terminals and a molecular weight of from 100 to 50,000, polyamines having 2 to 20 carbon atoms and 2 to 3 primary or secondary amino groups, saturated cyclic secondary amines having 4 to 20 carbon atoms, and cyclic polyamines having 4 to 20 carbon atoms and 2 to 3 secondary amino groups, a, b, c and d each stands for a positive integer of 3 or smaller or 0 with the proviso that they are not all 0 at the same time, Rs represent the same or different hydrocarbon groups having 1 to 10 carbon atoms, and two Rs on each common nitrogen atom may be coupled together to form a ring structure, which comprises reacting a salt of a phosphazenium cation and an inorganic anion, said salt being represented by the following formula (3):

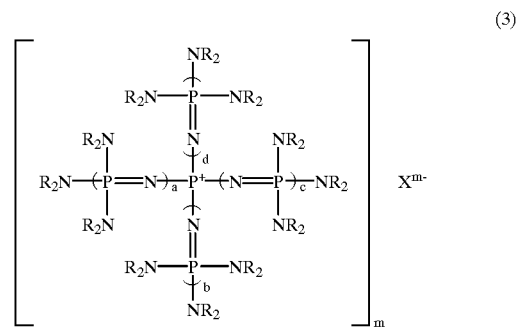

(3)

wherein m stands for an integer of from 1 to 3 and represents the number of said phosphazenium cation, $X^{m-}$ represents an m-valent inorganic anion, a, b, c, d and Rs have the same meanings as defined above, with an alkali metal salt of an active hydrogen compound represented by $M^+{}_n Z^{n-}$ wherein $M^+{}_n$ represents n alkali metal cations, and n and $Z^{n-}$ have the same meanings as defined above.

8. The process according to claim 7, wherein said inorganic anion is an anion of an acid selected from the group consisting of boric acid, tetrafluoroboric acid, hydrohalogenic acids, phosphoric acid, hexafluorophosphoric acid and perchloric acid.

9. A process for the preparation of a phosphazenium hydroxide represented by the following chemical formula (2):

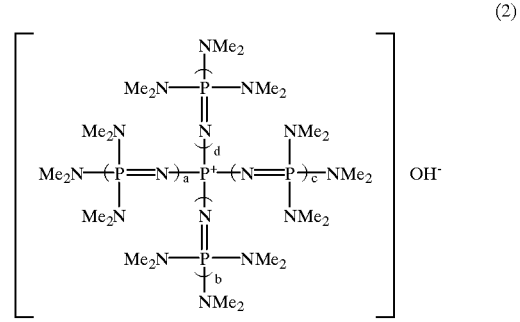

(2)

wherein each Me represents a methyl group, and a, b, c and d are each 0 or 1 with the proviso that they are not all 0 at the same time, which comprises bringing a solution of a salt of a phosphazenium cation and a monovalent inorganic anion, said salt being represented by the following formula (4):

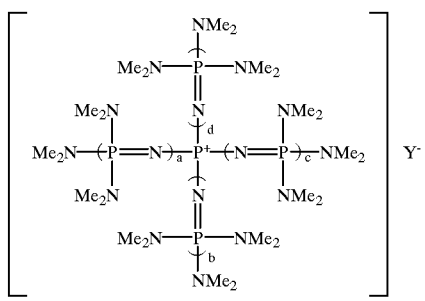

(4)

wherein each Me, a, b, c and d have the same meanings as defined above and Y⁻ represents said monovalent inorganic anion, in a mixed solvent of water and a water-miscible organic solvent into contact with a hydroxide form anion-exchange resin.

10. The process of claim 9, wherein said monovalent inorganic anion Y⁻ in the chemical formula (4) is an anion of a monovalent inorganic acid selected from the group consisting of hydrochloric acid, tetrafluoroboric acid, hexafluorophosphoric acid and perchloric acid.

11. The process according to claim 9, wherein said water-miscible organic solvent is selected from the group consisting of alcohols, ethers and nitriles.

* * * * *